US008436207B2

(12) United States Patent
Pellecchia

(10) Patent No.: US 8,436,207 B2
(45) Date of Patent: *May 7, 2013

(54) NAPHTHALENE-BASED INHIBITORS OF ANTI-APOPTOTIC PROTEINS

(75) Inventor: Maurizio Pellecchia, La Jolla, CA (US)

(73) Assignee: Burnham Institute for Medical Research, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/238,910

(22) Filed: Sep. 21, 2011

(65) Prior Publication Data

US 2012/0015992 A1 Jan. 19, 2012

Related U.S. Application Data

(63) Continuation of application No. 12/760,380, filed on Apr. 14, 2010, now Pat. No. 8,039,668, which is a continuation-in-part of application No. 12/253,918, filed on Oct. 17, 2008.

(60) Provisional application No. 61/254,172, filed on Oct. 22, 2009, provisional application No. 61/169,686, filed on Apr. 15, 2009, provisional application No. 61/097,171, filed on Sep. 15, 2008, provisional application No. 61/035,969, filed on Mar. 12, 2008, provisional application No. 60/981,400, filed on Oct. 19, 2007.

(51) Int. Cl.
C07C 233/65 (2006.01)
A61K 31/16 (2006.01)

(52) U.S. Cl.
USPC .......... 564/156; 562/467; 568/328; 568/441; 568/729; 514/367; 514/616; 514/617

(58) Field of Classification Search .................. 564/156; 568/328, 441, 729; 562/467; 514/367, 616, 514/700
See application file for complete search history.

(56) References Cited

U.S. PATENT DOCUMENTS

| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |
| 7,223,395 | B2 | 5/2007 | Muller et al. |
| 8,039,668 | B2 * | 10/2011 | Pellecchia ..................... 564/156 |
| 2004/0214902 | A1 | 10/2004 | Wang et al. |
| 2005/0027000 | A1 | 2/2005 | Reed et al. |
| 2006/0247305 | A1 | 11/2006 | Wang et al. |
| 2007/0037865 | A1 | 2/2007 | Nunes et al. |
| 2007/0149466 | A1 | 6/2007 | Milburn et al. |
| 2009/0105319 | A1 | 4/2009 | Pellecchia et al. |

FOREIGN PATENT DOCUMENTS

| WO | WO 02/40996 A2 | 5/2002 |
| WO | WO 2005/009434 | 6/2005 |
| WO | WO 2006/050447 A2 | 5/2006 |
| WO | WO 2009/052443 A1 | 4/2009 |

OTHER PUBLICATIONS

West, Anthony R., Solid State Chemistry and its Applications, Wiley, New York, 1988, pp. 358 & 365.*
Carter et al., Chemotherapy of Cancer, second edition, John Wiley & Sons, N.Y., N.Y., 1981, pp. 362-365.*
Carter et al., Chemotherapy of Cancer, second edition, John Wiley & Sons, N.Y., N.Y., pp. 362-365 (1981).
Pettinelli et al., "Adoptive transfer of experimental allergic encephalomyelitis in SJL/J mice after in vitro activation of lymph node cells by myelin basic protein: requirement for Lyt 1+ 2− T lymphocytes," Journal of Immunology 127:1420 (1981).
Rega et al., "Structure-based discovery of a new class of Bcl-xL antagonists", Bioorg. Chem., 35(4):344-53 (2007), Epub May 21, 2007.
West, A.R., Solid State Chemistry its Applications, Wiley, New York, pp. 358 & 365 (1988).
White et al., "Antibody-targeted Immunotherapy for Treatment of Malignancy," Annu. Rev. Med. 52:125 (2001). Yao et al., "Intra-articular injection of recombinant TRAIL induces synovial apoptosis and reduces inflammation in a rabbit knee model of arthritis", Arthritis Res. Ther., 8(1), pp. 1-2 (2005).
EP 10765133 Search Report dated Feb. 14, 2012.
PCT/US10/031113 International Search Report dated Jun. 17, 2010.
PCT/US10/031113 International Preliminary Report on Patentability and Written Opinion dated Oct. 18, 2011.
PCT/US08/080386 International Search Report dated Dec. 16, 2008.
PCT/US08/080386 International Preliminary Report on Patentability and Written Opinion dated Apr. 20, 2010.

* cited by examiner

Primary Examiner — Shailendra Kumar
(74) Attorney, Agent, or Firm — Wilson, Sonsini, Goodrich & Rosati

(57) ABSTRACT

Methods of using apogossypol and its derivatives for treating inflammation is disclosed. Also, there is described a group of compounds having structure A, or a pharmaceutically acceptable salt, hydrate, N-oxide, or solvate thereof are provided:

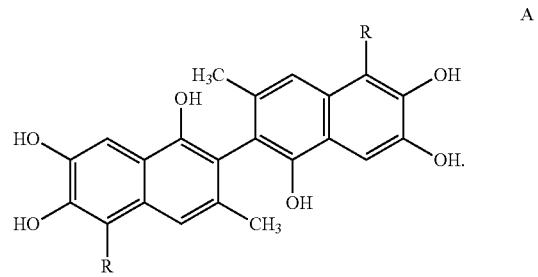

wherein each R is independently H, C(O)X, C(O)NHX, NH(CO)X, $SO_2NHX$, or $NHSO_2X$, wherein X is hydrogen, alkyl, substituted alkyl, aryl, substituted aryl, alkylaryl, substituted alkylaryl, heterocycle, or substituted heterocycle. Compounds of group A may be used for treating various diseases or disorders, such as cancer.

15 Claims, 25 Drawing Sheets

Reagents and conditions: (a) NaOH, $H_2O$, reflux; (b) $H_2SO_4$; (c) DMS, $K_2CO_3$; (d) $TiCl_4$, $Cl_2CHOCH_3$, rt; (e) HCl, $H_2O$ (f) $NaClO_2$, $H_2O_2$, $KH_2PO_4$, $CH_3CN$, rt; (g) HCl, $H_2O$; (h) EDCI, $NH_2R$, HOBT, rt; (i) $BBr_3$, $CH_2Cl_2$ (j) HCl, $H_2O$.

Reagents and conditions: (a) RMgBr or RLi, rt; (b) NH$_4$Cl, H$_2$O; (c) Pyridinium chlorochromate, CH$_2$Cl$_2$, rt; (d) Et$_3$SiH, TFA or Pd/C, H$_2$; (e) BBr$_3$; (f) HCl, H$_2$O.

Reagents and conditions: (a) $H_2SO_4$, rt; (b) $H_2O$; (c) $BBr_3$, $CH_2Cl_2$; (d) HCl, $H_2O$.

NAPHTHALENE-BASED INHIBITORS OF ANTI-APOPTOTIC PROTEINS

CROSS REFERENCE TO RELATED APPLICATIONS

This application is a continuation of U.S. patent application Ser. No. 12/760,380 filed on Apr. 14, 2010, now U.S. Pat. No. 8,039,668 which claims priority to U.S. Provisional Application No. 61/254,172 filed on Oct. 22, 2009, and U.S. Provisional Application No. 61/169,686, filed on Apr. 15, 2009, which is a continuation-in-part of U.S. patent application Ser. No. 12/253,918 filed on Oct. 17, 2008, which claims priority to U.S. Provisional Application No. 61/097,171 filed on Sep. 15, 2008, U.S. Provisional Application No. 61/035,969 filed Mar. 12, 2008 and U.S. Provisional Application No. 60/981,400 filed Oct. 19, 2007; the disclosures of which are hereby incorporated by reference in their entirety for all purposes.

GRANT INFORMATION

This invention was made in part with government support under NIH (Grant U01 AI061139 and Grant CA113318), and CSRA (Grant No. 08-02). The United States Government has certain rights in this invention.

FIELD OF THE DISCLOSURE

The disclosure relates generally to a class of compounds derived from naphthalene, such as apogossypol and derivatives thereof, for treating a variety of disorders, diseases and pathologic conditions, and more specifically, for treating cancer, autoimmune diseases, and/or inflammation.

BACKGROUND OF THE DISCLOSURE

The apoptotic cascade in cells is known to lead to cell death. When anti-apoptotic proteins, such as BCL-2 family proteins, are overproduced by the cells, uncontrollable cell growth may ensue, potentially leading to the development of various serious diseases, disorders, and pathologies, particularly cancer. Programmed cell-death (apoptosis) plays critical roles in the maintenance of normal tissue homeostasis, ensuring a proper balance of cell production and cell loss. Defects in the regulation of programmed cell death promote tumorgenesis, and also contribute significantly to chemoresistance. Bcl-2 (B-cell lymphoma/leukemia-2) family proteins are central regulators of apoptosis. In humans, six anti-apoptotic members of the Bcl-2 family have been identified and characterized thus far, including Bcl-2, Bcl-$X_L$, Mcl-1, Bfl-1, Bcl-W and Bcl-B. Over-expression of anti-apoptotic Bcl-2 family proteins occurs in many human cancers and leukemias, and therefore these proteins are very attractive targets for the development of novel anticancer agents. Members of the Bcl-2 family proteins also include pro-apoptotic effectors such as Bak, Bax, Bad, Bim and Bid. Anti-apoptotic and pro-apoptotic Bcl-2 family proteins dimerize and negate each other's functions. Structural studies have elucidated a hydrophobic crevice on the surface of anti-apoptotic Bcl-2 family proteins that binds the BH3 dimerization domain of pro-apoptotic family members. Thus, molecules that mimic the BH3 domain of pro-apoptotic proteins induce apoptosis and/or abrogate the ability of anti-apoptotic Bcl-2 proteins to inhibit cancer cell death.

Apoptosis plays a role in tissue homeostatis, for the physiological removal of unwanted cells during development and in host defense mechanism. The BCL-2 family of proteins are believed to be involved in regulating of apoptosis. Specifically, members of the BCL-2 gene family can act to inhibit programmed cell death (e.g., BCL-2, BCL-$X_L$, ced-9) or promote cell death (e.g., Bax, Bak, BCL-$X_S$). Pro-survival members of this family, such as BCL-$X_L$, contain, on the surface, a hydrophobic groove in which is believed to allow binding of the BH3 domain of the pro-apoptotic counterpart. This binding is believed to play role in apoptosis regulation, in fact pro- and anti-survival proteins can reverse each other function through dimerization.

Therefore, a need exists to inhibit anti-apoptotic proteins, such as the BCL-2 family proteins. Various potential BCL-2 antagonists have been previously identified. However, none of these compounds inhibits all six proteins in the BCL-2 family, i.e., all of the following proteins: BCL-$X_L$, BCL-2, BCL-W, BCL-B, BFL-1, and MCL-1. For example, none of the previously identified synthetic BCL-2 antagonists was effective at inhibiting the protein BFL-1. Therefore, the efficiency of such antagonists is not as high as desired. In addition, the existing antagonists are characterized by other drawbacks, such as insufficiency or safety issues.

Defects in the regulation of programmed cell death may promote tumorgenesis, and also contribute to chemoresistance. Over-expression of anti-apoptotic BCL-2 family proteins occurs in many human cancers and leukemias, and therefore these proteins may be used as targets for the development of novel anticancer agents. Structural studies have elucidated a hydrophobic crevice on the surface of anti-apoptotic BCL-2 family proteins that binds the BH3 dimerization domain of pro-apoptotic family members. Thus, molecules that mimic the BH3 domain of pro-apoptotic proteins induce apoptosis and/or abrogate the ability of anti-apoptotic BCL-2 proteins to inhibit cancer cell death.

It has been previously shown that the natural product gossypol shown on FIG. 1A is an inhibitor of BCL-2, BCL-$X_L$ and MCL-1, functioning as a BH3 mimic. (−) Gossypol is currently in clinical trails, displaying single-agent antitumor activity in patients with advanced malignancies. Given that gossypol has toxicity problems likely due to two reactive aldehyde groups, we prepared apogossypol, a compound that lacks these aldehydes, but retains activity against anti-apoptotic BCL-2 family proteins in vitro and in cells has been also evaluated previously. Recently, the efficacy and toxicity in mice of gossypol and apogossypol were compared. Preclinical in vivo data show that apogossypol has better efficacy and reduced toxicity compared to gossypol, as well as better single-dose pharmacokinetic characteristics, including, superior blood concentrations over time compared to gossypol, due to slower clearance. These observations indicate that apogossypol is a promising lead compound for cancer therapy.

BCL-2 family members are also believed to be involved in inflammatory disorders. For example, BCL-2 family members have been shown to play roles in neutrophil apoptosis and inflammatory accumulation. In several inflammatory diseases, the delay of neutrophil apoptosis is associated with reduced levels of the pro-apoptotic BCL-2 family member BAX. It has been also shown that eosinophils isolated from children with acute asthma had an increased expression of the anti-apoptotic protein BCL-2, which was inversely correlated with expiratory flow rate. BCL-2 family proteins are also associated with Crohn's disease. BAX expression is attenuated and BCL-$X_L$ expression is increased in T cells isolated from the lamina propria from patients with Crohn's disease. This shows that inflammatory cell survival, by means of pro-survival and anti-apoptotic signaling mechanisms, are involved in the pathogenesis of inflammatory diseases. Lupus is a complex systemic autoimmune disease, characterized by high levels of anti-DNA and anti-glomerular autoantibodies, activated B and T-cells, and glomerulonephritis. Neutrophils from lupus-susceptible mice display reduced rates of apoptosis. The decreased apoptosis is associated with the altered expression of BCL-2 family proteins contributing to the greater accumulation of neutrophils in the lupus-susceptible mice. Signaling studies using several different lupus strains indicate that multiple signaling pathways are upregulated in lymphocytes and non lymphocytes as disease evolves, including the activation of BCL-2 and BCL-$X_L$. These anti-apoptotic molecules are known to prolong the lifespan of all cells, including autoreactive B and T cells.

In view of these drawbacks and deficiencies of existing BCL-2 inhibitors, new antagonists of anti-apoptotic proteins, such as BCL-2 family proteins, are desired. It is desirable that such new antagonists be safer and more effective than the existing compounds.

SUMMARY OF THE DISCLOSURE

The disclosure addresses these needs by providing new antagonists of anti-apoptotic proteins, including the BCL-2 family of proteins. Thus, in one embodiment the disclosure provides compounds having structure A, or pharmaceutically acceptable salts, hydrates, N-oxides, or solvates thereof:

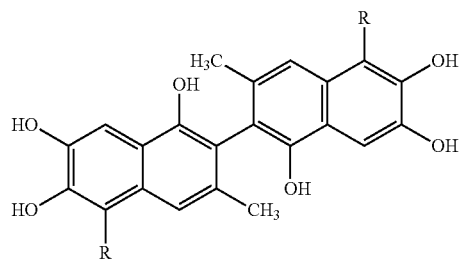

A wherein each R is independently H, C(O)X, C(O)NHX, NH(CO)X, $SO_2NHX$, and $NHSO_2X$, wherein X is an hydroxyl, alkyl, substituted alkyl, aryl, substituted aryl, alkylaryl, substituted alkylaryl, a heterocycle, or a substituted heterocycle.

According to another embodiment, the disclosure provides a compound that is a species of the compounds having structure A, the specific compound having the formula I:

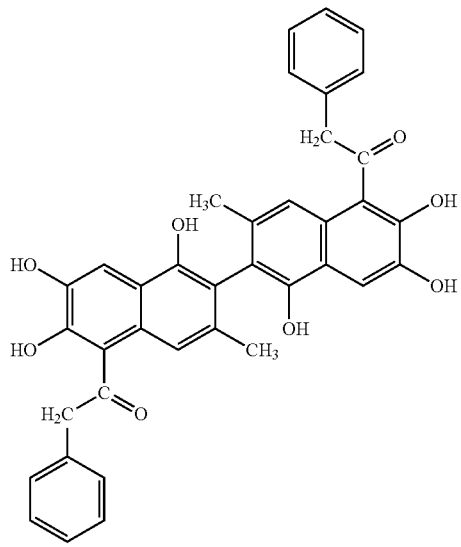

I

According to another embodiment, the disclosure provides a method for treating cancer or autoimmune diseases, by administering to a subject in need thereof a therapeutically effective amount of the compounds having structure A, including the species I, or pharmaceutically acceptable salts, hydrates, N-oxides, or solvates thereof.

The disclosure also provides a method for treating inflammation. In particular, the disclosure relates to the use of apogossypol for the treatment of inflammation. Accordingly, a method for treating inflammation is disclosed. The method includes administering to a mammal a compound, in an amount effective to reduce inflammation, the compound having structure B:

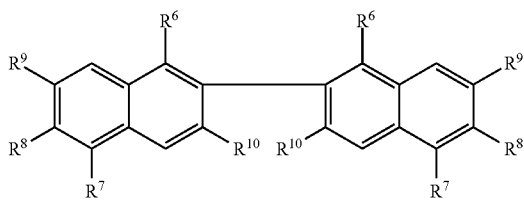

B wherein each of $R^6$, $R^8$, $R^9$ and $R^{10}$ is hydrogen, hydroxyl, —($C_1$-$C_6$)alkyl, —O($C_1$-$C_6$)alkyl, —($C_1$-$C_6$)alkylhalo, —OC(O)($C_1$-$C_6$)alkyl, and halo, and each $R^7$ is hydrogen, —($C_1$-$C_6$)alkyl, —($C_3$-$C_8$)cycloalkyl, —($C_6$-$C_{10}$)aryl, and —($C_1$-$C_6$)alkyl($C_6$-$C_{10}$)aryl, C(O)X, C(O)NHX, NH(CO)X, $SO_2NHX$, and $NHSO_2X$, wherein X is hydroxyl, alkyl, substituted alkyl, aryl, substituted aryl, alkylaryl, substituted alkylaryl, heterocycle, or substituted heterocycle or a pharmaceutically acceptable salt, hydrate, N-oxide, or solvate thereof. In some embodiments, the compound is used to treat inflammation is apogossypol, for example, (−) apogossypol that is substantially free of (+) apogossypol.

Also disclosed is a method of treating inflammation in a subject, by administering to the subject an anti-inflammatory agent selected from gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), derivatives of purpurogallin, and mixtures thereof.

In addition, the disclosure provides a method for inducing apoptosis, modulating caspase activity, or inducing cell death in a mammal suffering from an inflammatory disease inflammation is disclosed. The method comprises contacting the mammal with a compound in the amount effective to induce apoptosis, modulate caspase activity, or induce cell death the target cells, the compound to be used having structure B as described herein.

DETAILED DESCRIPTION OF THE DISCLOSURE

Figure 1:
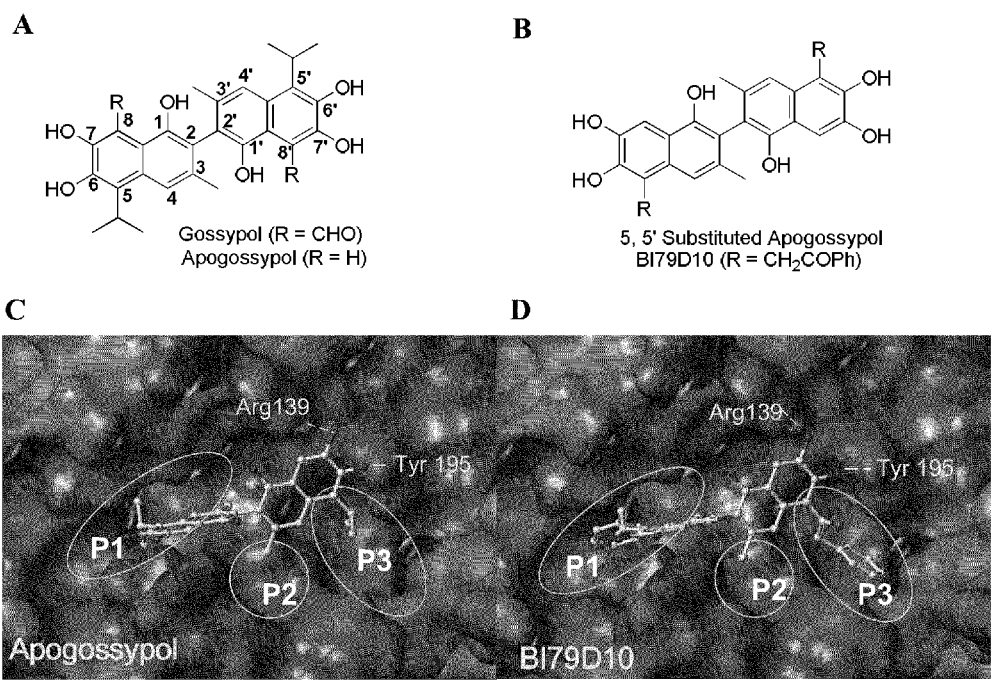
FIG. 1 demonstrates structures of gossypol and apogossypol (A); structure of a compound of the disclosure (B); and molecular docking studies (C, D).

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, definitions and abbreviations further apply:

The term "patient" refers to organisms to be treated by the methods of the disclosure. Such organisms include, but are not limited to, humans and other mammals. In the context of the disclosure, the term "subject" generally refers to an individual who will receive or who has received treatment described herein (e.g., administration of the compounds of the disclosure, and optionally one or more additional therapeutic agents).

The term "BCL-2 family of proteins" refers to the family of proteins that currently includes at least the following six proteins: BCL-$X_L$, BCL-2, BCL-W, BCL-B, BFL-1, and MCL-1.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

Specific values listed herein for groups, substituents, and ranges, are for illustration; they do not exclude other defined values or other values within defined ranges for the groups and substituents. For example, "alkyl" can be methyl, ethyl, propyl, isopropyl, butyl isobutyl, sec-butyl, pentyl, 3-pentyl, or hexyl; cycloalkyl can be cyclopropyl, cyclobutyl, cyclopentyl, or cyclohexyl; "—O($C_1$-$C_6$)alkyl (alkoxy)" can be methoxy, ethoxy, propoxy, isopropoxy, butoxy, iso-butoxy, sec-butoxy, pentoxy, 3-pentoxy, or hexyloxy.

The term "alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$.ident.$CCH_2$—, —$CH_2CH_2CH(CH_2CH_2CH_3)CH_2$—. Typically, an alkyl (or alkylene) group will have from 1 to 24 carbon atoms, which includes those groups having 10 or fewer carbon atoms. A "lower alkyl" or "lower alkylene" is a shorter chain alkyl or alkylene group, generally having eight or fewer carbon atoms.

The terms "alkyl, alkoxy, alkenyl, alkynyl," etc. denote both straight and branched groups; but reference to an individual group such as "propyl" embraces the straight chain group, a branched chain isomer such as "isopropyl" being specifically referred to.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— includes both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, re, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

More specifically, the term "alkyl" refers to a branched or unbranched saturated hydrocarbon group of 1 to 6 carbon atoms, such as methyl, ethyl, n-propyl, isopropyl, n-butyl, isobutyl, t-butyl, pentyl, and the like. Alkyl groups herein contain 1 to 6 carbon atoms, such as, for example, methyl, ethyl, and the like. As used herein the term "alkyl" also includes the term "cycloalkyl," which refers to a cyclic alkyl group of three to eight, including three, five or six, carbon atoms. The term "cycloalkylene" as used herein refers to a divalent cyclic alkylene group, typically a 3-, 5-, 6-, or 8-membered ring.

The term "alkoxy" as used herein refers to an alkyl group bound through a single, terminal ether linkage, i.e., an "alkoxy" group may be defined as —OR, where R is alkyl as defined herein. A "lower alkoxy" group refers to an alkoxy group containing 1 to 6, carbon atoms.

The term "aryl" means, unless otherwise stated, a polyunsaturated, aromatic, hydrocarbon substituent which can be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover aryls substituted with one or more halogens.

The term "aryl" as used herein refers to an aromatic carbocyclic ring, typically 6- or 10-membered, wherein at least one ring is aromatic. For example, "aryl" denotes a phenyl group or an ortho-fused bicyclic carbocyclic group having about nine to ten ring atoms in which at least one ring is aromatic.

"Heteroaryl" encompasses a group attached via a ring carbon of a monocyclic aromatic ring containing five or six ring atoms consisting of carbon and one to four heteroatoms each independently may be non-peroxide oxygen, sulfur, and N(X), where X is absent or is H, O, ($C_1$-$C_4$)alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

Where a heteroalkyl, heterocycloalkyl, or heteroaryl includes a specific number of members (e.g. "3 to 7 membered"), the term "member" referrers to a carbon or heteroatom.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. The term "halo" also refers to fluoro, chloro, bromo, or iodo.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is. When R' and R''' are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH—, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R' group, for example, each of the R groups is independently selected as are each R', R", R''' and R'''' groups when more than one of these groups is.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) -OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the disclosure may exist as salts. The disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, mono-hydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methane-sulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The neutral forms of the compounds are regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the compounds are within the scope of the disclosure.

Unless otherwise stated, structures depicted herein are also meant to include compounds which differ in the presence of one or more isotopically enriched atoms. For example, compounds having the structures except for the replacement of a hydrogen by a deuterium or tritium, or the replacement of a carbon by $^{13}$C- or $^{14}$C-enriched carbon are within the scope of this disclosure.

The compounds of the disclosure may also contain unnatural proportions of atomic isotopes at one or more of atoms that constitute such compounds. For example, the compounds may be radio labeled with radioactive isotopes, such as for example tritium (3H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt.

When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The term "prodrug" or "pro-drug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "apogossypol" is a broad term which includes, without limitation, L-apogossypol, D-apogossypol, racemic apogossypol, S-apogossypol, R-apogossypol, (−) apogossypol and (+) apogossypol, and includes (−)apogossypol that is substantially free of (+)apogossypol.

Throughout the disclosure, when a particular compound is mentioned by name, for example, apogossypol, it is understood that the scope of the disclosure encompasses pharmaceutically acceptable salts, esters, amides, metabolites, or prodrugs of the named compound.

It will be appreciated by those skilled in the art that compounds of the disclosure having a chiral center may exist in and be isolated in optically active and racemic forms. Some compounds may exhibit polymorphism. It is to be understood that the disclosure encompasses any racemic, optically active, polymorphic, or stereoisomeric form, or mixtures thereof, of a compound of the disclosure, which possesses the useful properties described herein. Also, if the named compound comprises a chiral center, the scope of the disclosure also includes compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or a composition comprising the R enantiomer substantially free of the S enantiomer.

By "substantially free" it is meant that the composition comprises less than 10%, or less than 8%, or less than 5%, or less than 3%, or less than 1% of the minor enantiomer. If the named compound comprises more than one chiral center, the scope of the disclosure also includes compositions comprising a mixture of the various diastereomers, as well as compositions comprising each diastereomer substantially free of the other diastereomers. Thus, for example, commercially available apogossypol is a racemic mixture comprising two separate enantiomers. The recitation of "apogossypol" throughout this disclosure includes compositions that comprise the racemic mixture of apogossypol, compositions that comprise the (+) enantiomer substantially free of the (−) enantiomer, and compositions that comprise the (−) enantiomer substantially free of the (+) enantiomer.

It is well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

The term "pharmaceutical composition" refers to a mixture of a compound with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the disclosure with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the disclosure with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

"Inflammation" as used herein is a general term for the local accumulation of fluid, plasma proteins, and white blood cells that is initiated by physical injury, infection, or a local immune response. Many different forms of inflammation are associated with different diseases. "Inflammation-associated" diseases include, for example, lupus, psoriasis, rheumatoid arthritis, and inflammatory bowel disease. Other inflammation-associated diseases are discussed herein.

As used herein, the terms "anti-inflammatory agent" refers to any anti-inflammatory compounds that are used in the treatment of inflammation.

"Treatment," as used herein, pertains to the therapeutic administration of the compounds of the disclosure for the prevention, amelioration, or cure of disease.

The term "pharmaceutical agent or drug" as used herein refers to a chemical compound or composition capable of inducing a desired therapeutic effect when properly administered to a patient.

As used herein, "substantially pure" means an object species is the predominant species (i.e., on a molar basis it is more abundant than any other individual species in the composition), and a substantially purified fraction is a composition wherein the object species comprises at least about 50 percent (on a molar basis) of all macromolecular species. Generally, a substantially pure composition will comprise more than about 80 percent of all macromolecular species in the composition, for example, more than about 85%, 90%, 95%, and 99%. The object species may be also purified to essential homogeneity (contaminant species cannot be detected in the composition by conventional detection methods), wherein the composition consists essentially of a single species.

In one aspect the disclosure provides a compound having structure A, or a pharmaceutically acceptable salt, hydrate, N-oxide, or solvate thereof:

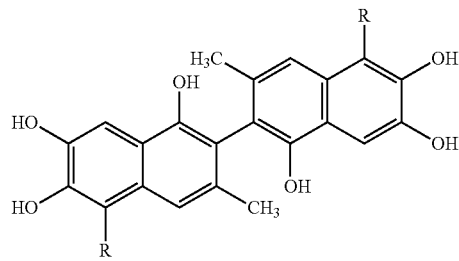

A wherein each R is independently H, C(O)X, C(O)NHX, NH(CO)X, SO$_2$NHX, or NHSO$_2$X; and X is hydroxyl, alkyl, substituted alkyl, aryl, substituted aryl, alkylaryl, substituted alkylaryl, heterocycle, or substituted heterocycle.

In another aspect the disclosure provides a compound having structure A, wherein each R is independently NH(CO)X; and X is alkyl, substituted alkyl, aryl, substituted aryl, alkylaryl, substituted alkylaryl, heterocycle, or substituted heterocycle.

In another aspect the disclosure provides a compound having structure A, wherein X is (C$_1$-C$_6$)alkyl, substituted (C$_1$-C$_6$)alkyl, (C$_3$-C$_8$)cycloalkyl, substituted (C$_3$-C$_8$)cycloalkyl, phenyl, substituted phenyl, (C$_1$-C$_6$)alkylaryl or substituted (C$_1$-C$_6$)alkylaryl, wherein each substitutent is (C$_1$-C$_6$)alkyl, trifluoromethyl, halogen, phenyl or phenoxy.

In another aspect the disclosure provides a compound having structure A, wherein each R is independently

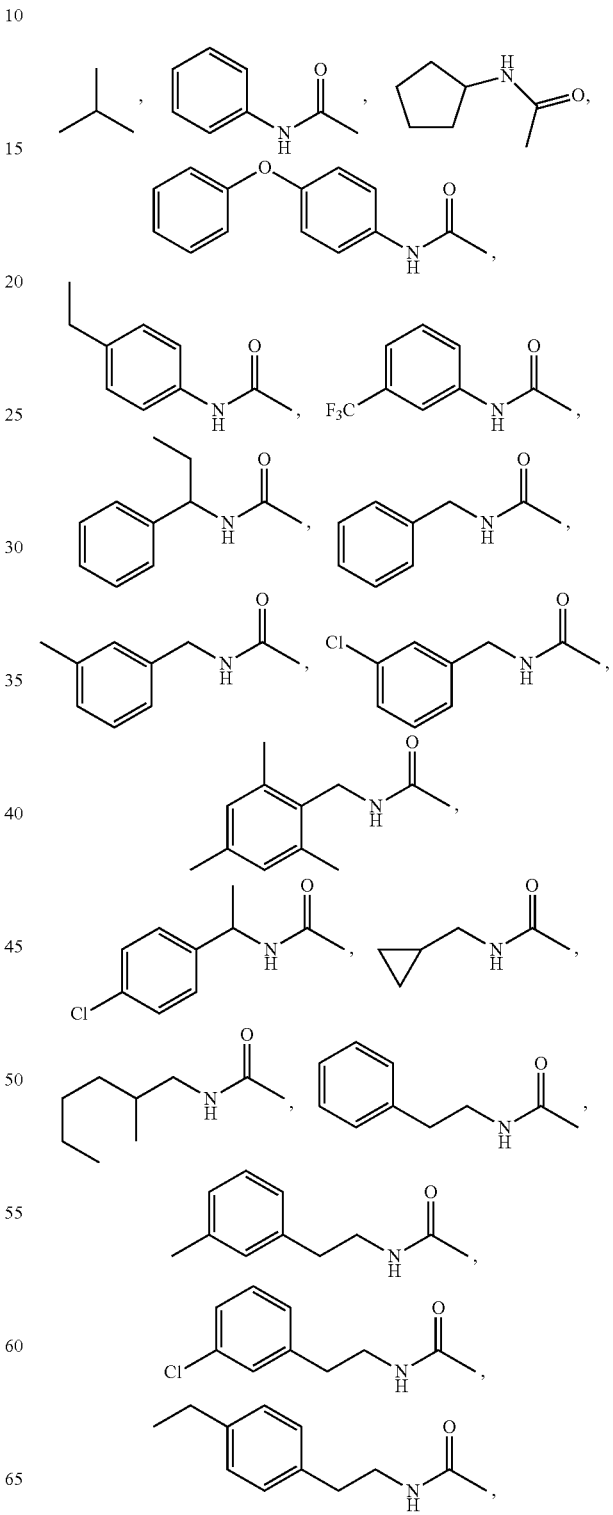

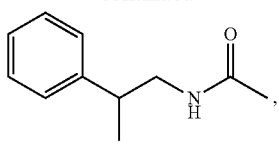

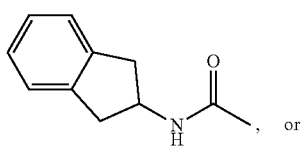

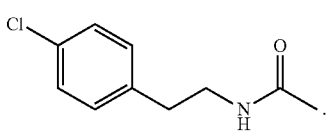

In another aspect the disclosure provides a compound having structure A, wherein each R is independently C(O)NHCH$_2$CH(CH$_3$)C$_6$H$_5$.

In another aspect the disclosure provides a compound having structure A, wherein X is an alkylaryl.

In another aspect the disclosure provides a compound having structure A, wherein X is benzyl.

In another aspect the disclosure provides a compound having structure A, wherein the compound is:

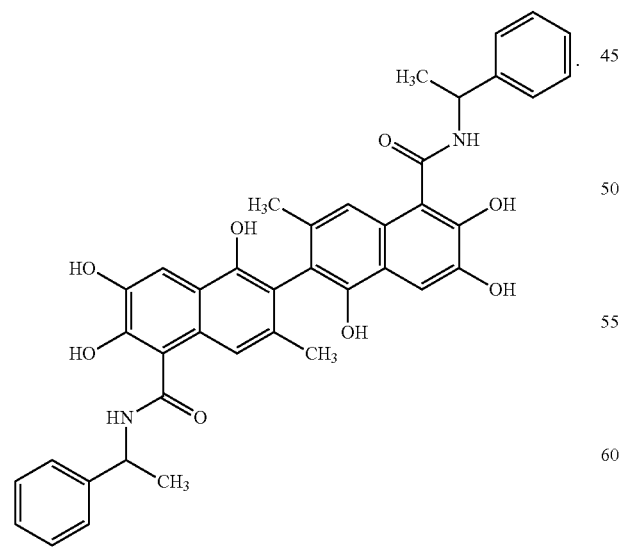

In another aspect the disclosure provides a compound having structure A, wherein the compound is compound I-XXII:

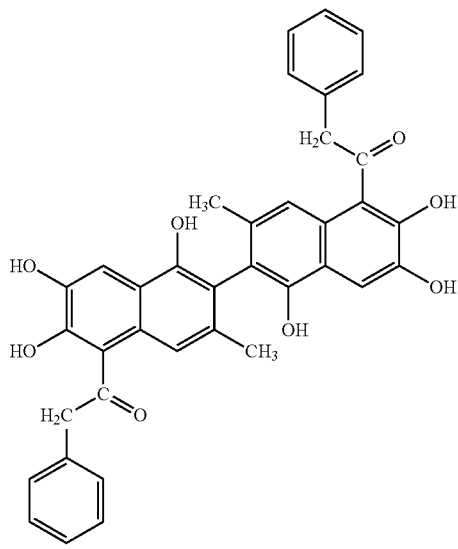

I

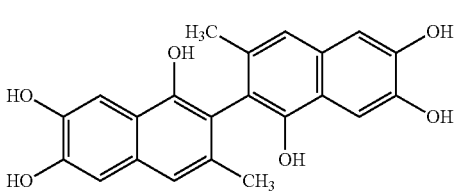

II

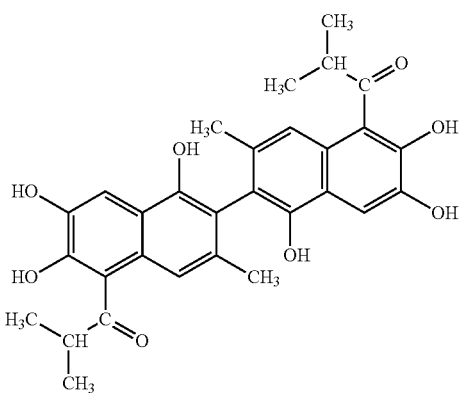

III

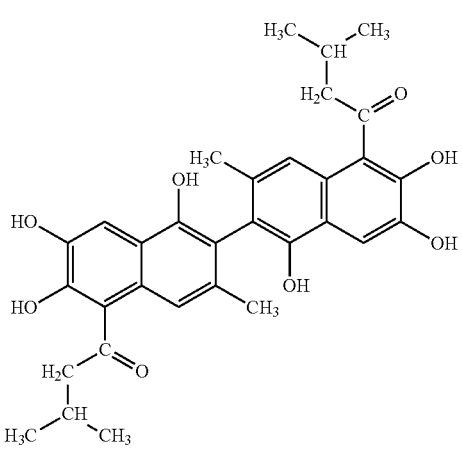

IV

-continued
V
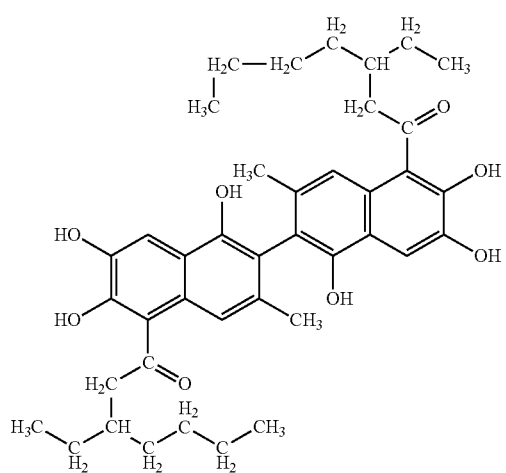
VI
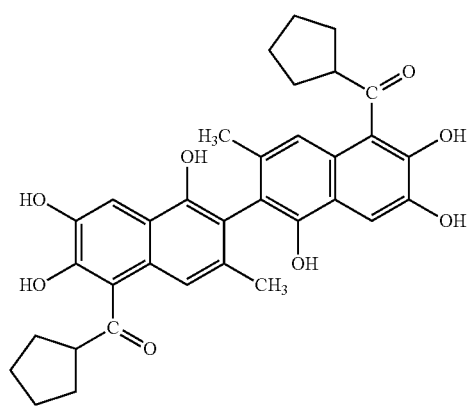
VII
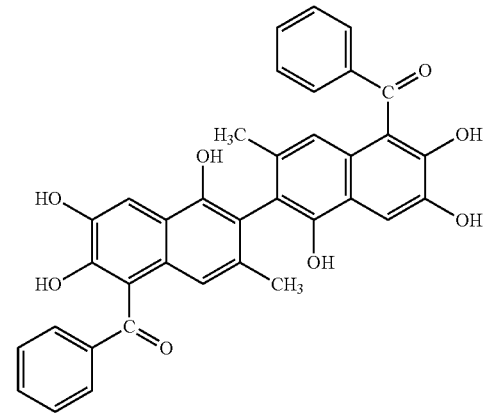
-continued
VIII
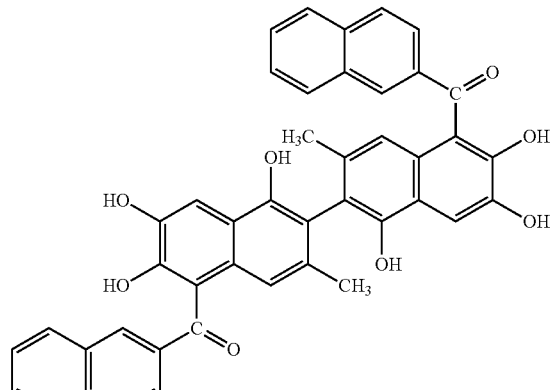
IX
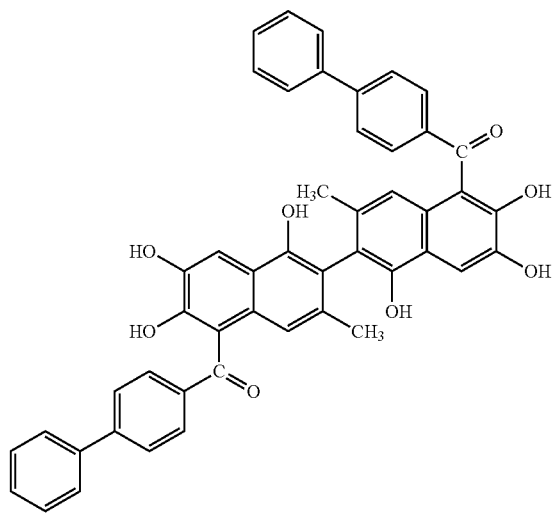
X
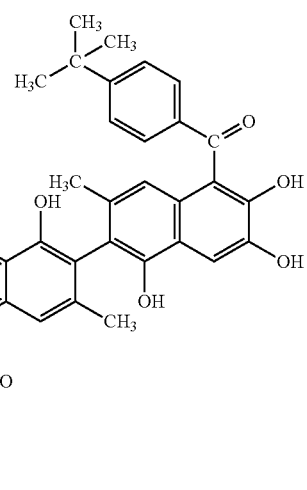

XI
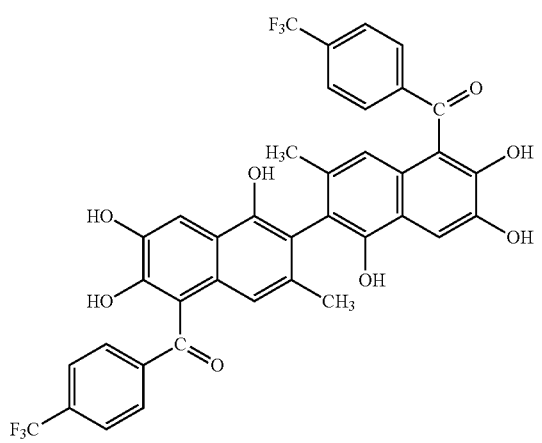
XII
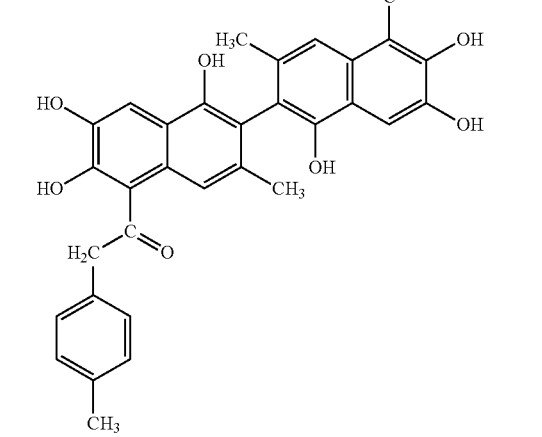
XIII
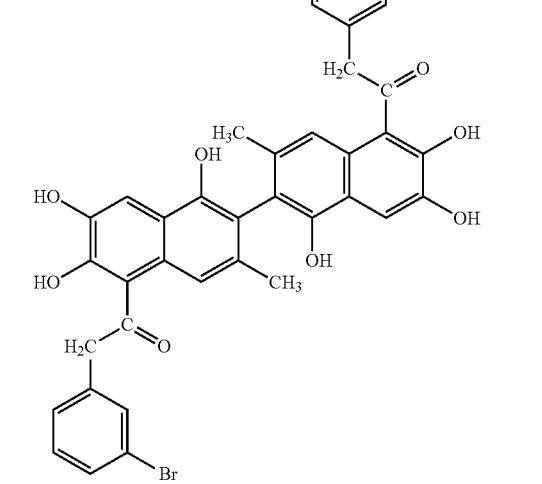
XIV
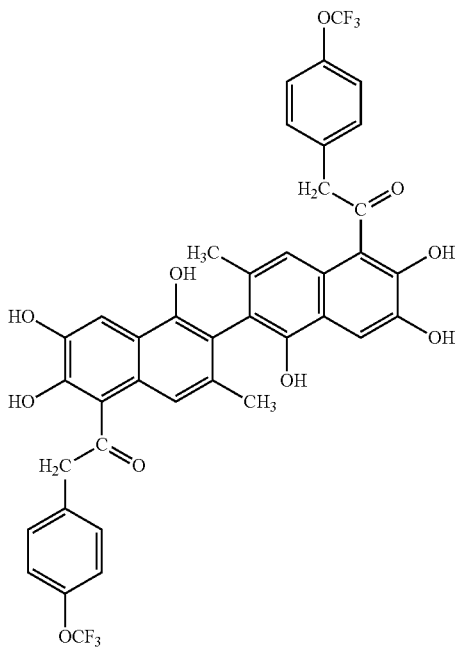
XV
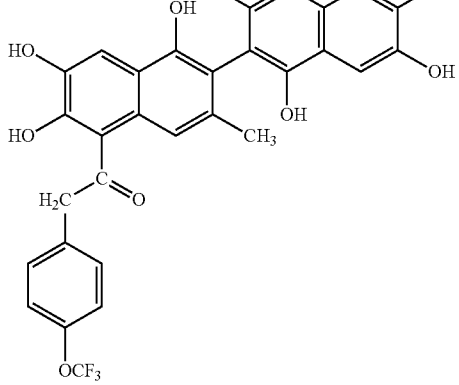

XVI
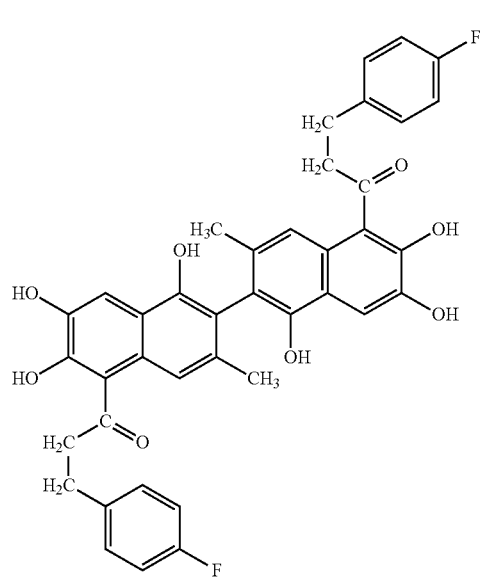
XVII
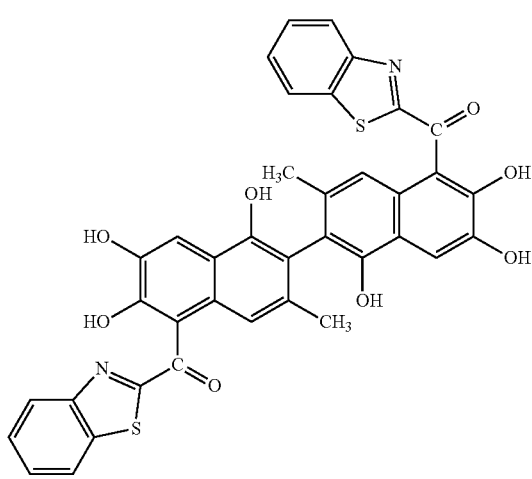
XVIII
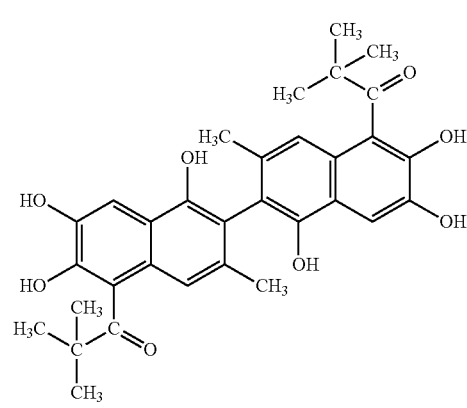
XIX
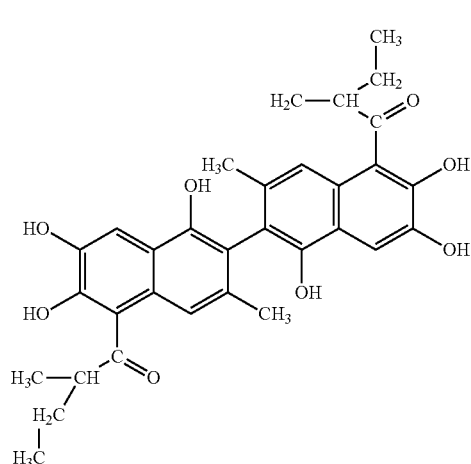
XX
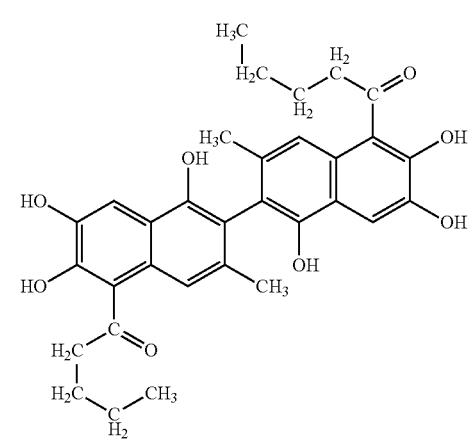
XXI
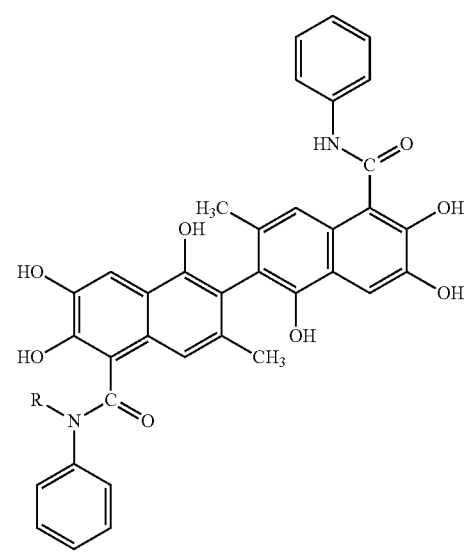

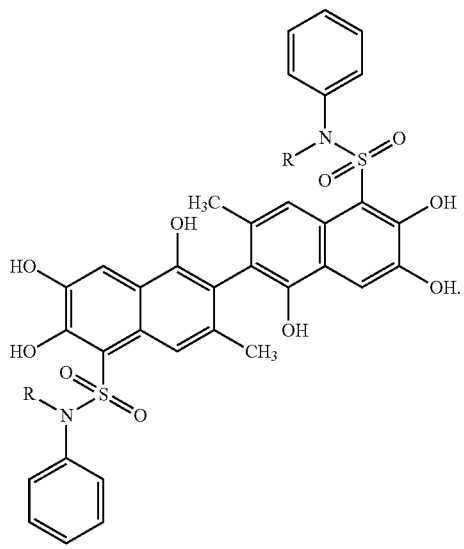

XXII

In another aspect the disclosure provides a compound having structure A, wherein the compound is compound I:

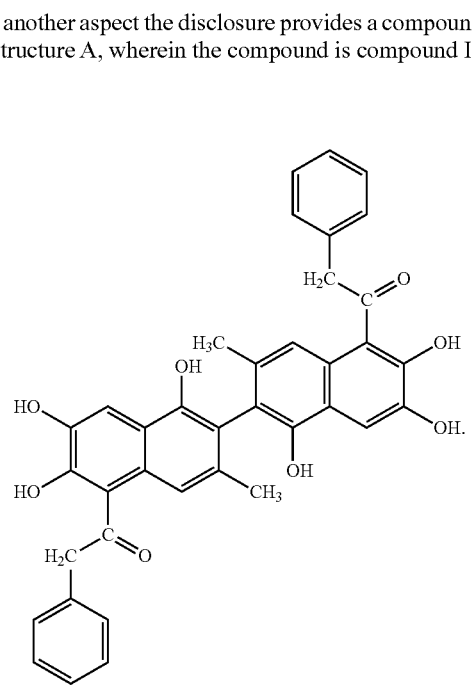

I

In another aspect the disclosure provides a compound having structure A, wherein the compound is compound XXI:

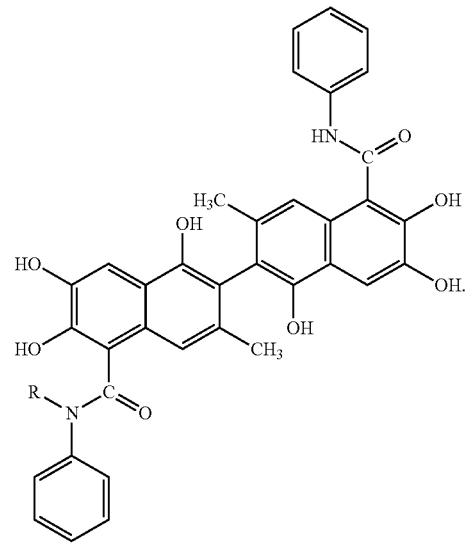

XXI

In another aspect the disclosure provides a compound having structure A, wherein the compound is compound XXII:

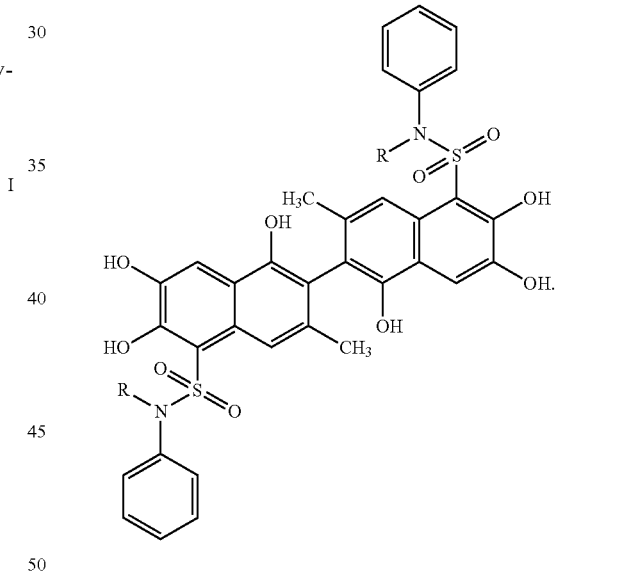

XXII

In another aspect the disclosure provides methods for treating a disease or a disorder, by administering to a subject in need thereof a therapeutically effective amount of a compound having structure A, or a combination thereof, or a pharmaceutically acceptable salt, hydrate, N-oxide, or solvate thereof, thereby treating the disease or the disorder.

In another aspect the disclosure provides methods for treating a disease or a disorder, by administering to a subject in need thereof a therapeutically effective amount of a compound having structure A, wherein the disease or the disorder is cancer.

In another aspect the disclosure provides methods for treating a disease or a disorder, by administering to a subject in need thereof a therapeutically effective amount of a compound having structure A, wherein the disease or the disorder is cancer, and wherein cancer is lung cancer, breast cancer, prostate cancer, or lymphomas.

In another aspect the disclosure provides methods for treating a disease or a disorder, by administering to a subject in need thereof a therapeutically effective amount of a compound having structure A, wherein the treatment includes inhibition of activity of at least one BCL-2 family protein.

In another aspect the disclosure provides methods for treating a disease or a disorder, by administering to a subject in need thereof a therapeutically effective amount of a compound having structure A, by administering the compound having structure A in combination with an anti-cancer agent.

In another aspect the disclosure provides methods for treating cancer or an autoimmune disease in a subject having at least one elevated BCL-2 family protein expression level by administering to the subject a therapeutically effective amount of a compound having structure A, or a combination thereof, or a pharmaceutically acceptable salt, hydrate, N-oxide, or solvate thereof.

In another aspect the disclosure provides methods for treating cancer or an autoimmune disease in a subject having at least one elevated BCL-2 family protein expression level by administering to the subject a therapeutically effective amount of a compound having structure A, by determining whether the subject is responsive to a therapy that utilizes the compound, and determining the level of at least one of the BCL-2 family protein in the subject and comparing to a normal control sample, wherein an elevated level is indicative of a subject responsive to the therapy that the compound, or a pharmaceutically acceptable salt, hydrate, N-oxide, or solvate thereof.

In another aspect the disclosure provides methods for treating cancer or an autoimmune disease in a subject having at least one elevated BCL-2 family protein expression level comprising administering to the subject a therapeutically effective amount of a compound having structure A, by determining whether the subject is responsive to a therapy that utilizes the compound, and determining the level of at least one of the BCL-2 family protein in the subject and comparing to a normal control sample, wherein an elevated level is indicative of a subject responsive to the therapy that the compound, or a pharmaceutically acceptable salt, hydrate, N-oxide, or solvate thereof, wherein the determination is made based on a sample from the subject.

In another aspect the disclosure provides methods for determining whether a subject is responsive to a therapy that utilizes of a compound having structure A, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof.

In another aspect the disclosure provides methods for determining whether a subject is responsive to a therapy that utilizes of a compound having structure A, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, and wherein the determination is made based on a sample from the subject.

In another aspect the disclosure provides methods for determining whether a subject is responsive to a therapy that utilizes of a compound having structure A, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, and wherein the sample is a biological fluid or tumor sample.

In another aspect the disclosure provides methods for determining whether a subject is responsive to a therapy that utilizes of a compound having structure A, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, and wherein the BCL-2 family polynucleotide or polypeptide is selected from BCL-2, BCL-XL, BCL-W, MCL-1, and BCL-A1.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cancer cell.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cancer cell, and wherein cancer is lung cancer, breast cancer, prostate cancer, or lymphomas.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cell of the immune system.

In another aspect the disclosure provides methods for determining the effectiveness of a therapeutic regimen including administration of the compound of a compound having structure A, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof.

In another aspect the disclosure provides methods for determining the effectiveness of a therapeutic regimen including administration of the compound of a compound having structure A, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has cancer.

In another aspect the disclosure provides methods for determining the effectiveness of a therapeutic regimen including administration of the compound of a compound having structure A, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has cancer, and wherein cancer is lung cancer, breast cancer, prostate cancer, or lymphomas.

In another aspect the disclosure provides methods for determining the effectiveness of a therapeutic regimen including administration of the compound of a compound having structure A, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has an autoimmune disorder.

In another aspect the disclosure provides methods for treating inflammation in a subject by administering to the subject in need of the treatment a pharmaceutically effective amount of a compound having structure B:

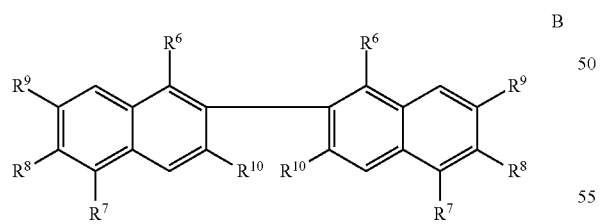

wherein each of $R^6$, $R^8$, $R^9$ and $R^{10}$ is hydrogen, hydroxyl, —$(C_1$-$C_6)$alkyl, —O$(C_1$-$C_6)$alkyl, —$(C_1$-$C_6)$alkylhalo, —OC(O)$(C_1$-$C_6)$alkyl, or halo; and each $R^7$ is independently hydrogen, —$(C_1$-$C_6)$alkyl, —$(C_3$-$C_8)$cycloalkyl, —$(C_6$-$C_{10})$aryl, and —$(C_1$-$C_6)$alkyl$(C_6$-$C_{10})$aryl, C(O)X, C(O)NHX, NH(CO)X, SO$_2$NHX, and NHSO$_2$X, wherein X is alkyl, substituted alkyl, aryl, substituted aryl, alkylaryl, substituted alkylaryl, heterocycle, or a substituted heterocycle, or a pharmaceutically acceptable salt, hydrate, N-oxide, or solvate thereof, to reduce the inflammation thereby.

In another aspect the disclosure provides methods for treating inflammation in a subject by administering to the subject in need of the treatment a pharmaceutically effective amount of a compound having structure B, wherein the compound is apogossypol.

In another aspect the disclosure provides methods for treating inflammation in a subject by administering to the subject in need of the treatment a pharmaceutically effective amount of a compound having structure B, wherein the compound is apogossypol, wherein the compound is (−) apogossypol substantially free of (+) apogossypol.

In another aspect the disclosure provides methods for treating inflammation in a subject by administering to the subject in need of the treatment a pharmaceutically effective amount of a compound having structure B, wherein each of $R^6$, $R^8$, $R^9$ and $R^{10}$ is independently hydrogen, —OH, —OCH$_3$, —CF$_3$, —CH$_3$, —OC$_2$H$_5$, —OC(O)CH$_3$, F, Cl, or Br.

In another aspect the disclosure provides methods for treating inflammation in a subject by administering to the subject in need of the treatment a pharmaceutically effective amount of a compound having structure B, wherein each R is independently hydrogen, ethyl, n-propyl, iso-propyl, n-butyl, tert-butyl, iso-butyl, sec-butyl, or cyclohexyl.

In another aspect the disclosure provides methods for treating inflammation in a subject by administering to the subject in need of the treatment a pharmaceutically effective amount of a compound having structure B, wherein each $R^{10}$ is independently hydrogen, —OH, —OCH$_3$, —CF$_3$, —CH$_3$, —OC$_2$H$_5$, —OC(O)CH$_3$, F, Cl, or Br.

In another aspect the disclosure provides methods for treating inflammation in a subject by administering to the subject in need of the treatment a pharmaceutically effective amount of a compound having structure B, wherein each $R^6$, $R^8$, and $R^9$ is —OC(O)CH$_3$, each $R^7$ is iso-propyl; and each $R^{10}$ is —CH$_3$.

In another aspect the disclosure provides methods for treating inflammation in a subject by administering to the subject in need of the treatment a pharmaceutically effective amount of a compound having structure B, wherein the compound is a pro-drug of apogossypol.

In another aspect the disclosure provides methods for treating inflammation in a subject by administering to the subject in need of the treatment a pharmaceutically effective amount of a compound having structure B, wherein the compound is compound XXI:

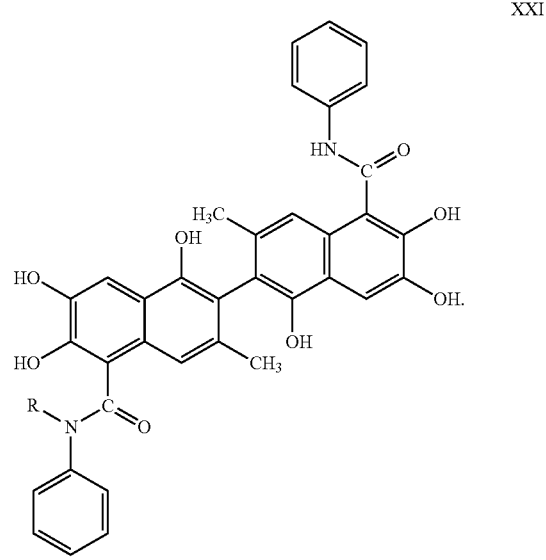

In another aspect the disclosure provides methods for treating inflammation in a subject by administering to the subject in need of the treatment a pharmaceutically effective amount of a compound having structure B, wherein the compound is compound XXII:

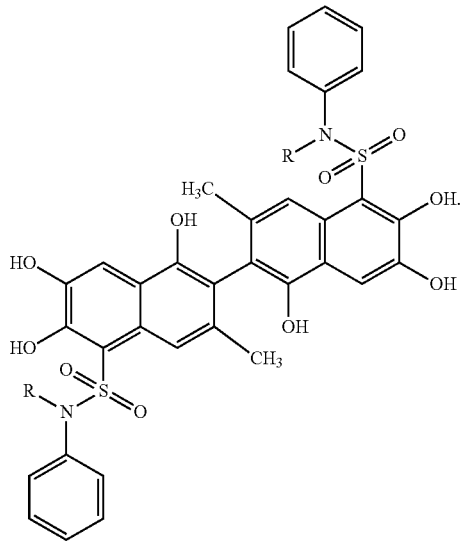

XXII

In another aspect the disclosure provides methods for treating inflammation in a subject by administering to the subject in need of the treatment a pharmaceutically effective amount of a compound having structure B, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating inflammation in a subject by administering to the subject in need of the treatment a pharmaceutically effective amount of a compound having structure B, wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for treating inflammation in a subject by administering to the subject in need of the treatment a pharmaceutically effective amount of a compound having structure B, and administering a selective serotonin reuptake inhibitor (SSRI).

In another aspect the disclosure provides methods for treating inflammation in a subject in need of such treatment by administering to the subject in need of the treatment an anti-inflammatory agent, wherein the anti-inflammatory agent is gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby.

In another aspect the disclosure provides methods for treating inflammation in a subject in need of such treatment by administering to the subject in need of the treatment an anti-inflammatory agent, wherein the anti-inflammatory agent is gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby, and administering a selective serotonin reuptake inhibitor (SSRI).

In another aspect the disclosure provides methods for treating inflammation in a subject in need of such treatment by administering to the subject in need of the treatment an anti-inflammatory agent, wherein the anti-inflammatory agent is apogossypol.

In another aspect the disclosure provides methods for treating inflammation in a subject in need of such treatment by administering to the subject in need of the treatment an anti-inflammatory agent, wherein the anti-inflammatory agent is (−) apogossypol substantially free of (+) apogossypol.

In another aspect the disclosure provides methods for treating inflammation in a subject in need of such treatment by administering to the subject in need of the treatment an anti-inflammatory agent, wherein the anti-inflammatory agent is a derivative of apogossypol, wherein the derivative of apogossypol is a compound having structure B, wherein the derivative a purpurogallin derivative is 5D1, 1163, or 1142.

In another aspect the disclosure provides methods for treating inflammation in a subject in need of such treatment by administering to the subject in need of the treatment an anti-inflammatory agent, wherein the anti-inflammatory agent is gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby, wherein the inflammation is inflammation associated with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating inflammation in a subject in need of such treatment by administering to the subject in need of the treatment an anti-inflammatory agent, wherein the anti-inflammatory agent is gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby, wherein the inflammation is inflammation associated with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor, wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, wherein the disease or the disorder is cancer.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, wherein the disease or the disorder is cancer, wherein cancer is lung cancer, breast cancer, prostate cancer, or lymphomas.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, and wherein the treatment includes inhibition of activity of at least one BCL-2 family protein.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, by administering the compound in combination with an anti-cancer agent.

In another aspect the disclosure provides methods for treating cancer or an autoimmune disease in a subject having at least one elevated BCL-2 family protein expression level by administering to the subject a therapeutically effective amount of a compound or stereoisomer thereof as described herein, or a combination thereof, or a pharmaceutically acceptable salt, hydrate, N-oxide, or solvate thereof.

In another aspect the disclosure provides methods for treating cancer or an autoimmune disease in a subject having at least one elevated BCL-2 family protein expression level by administering to the subject a therapeutically effective amount of a compound or stereoisomer thereof as described herein, or a combination thereof, or a pharmaceutically acceptable salt, hydrate, N-oxide, or solvate thereof, by determining whether the subject is responsive to a therapy that utilizes the compound, by determining the level of at least one of the BCL-2 family protein in the subject and comparing to a normal control sample, wherein an elevated level is indicative of a subject responsive to the therapy that the compound, or a pharmaceutically acceptable salt, hydrate, N-oxide, or solvate thereof.

In another aspect the disclosure provides methods for treating cancer or an autoimmune disease in a subject having at least one elevated BCL-2 family protein expression level by administering to the subject a therapeutically effective amount of a compound or stereoisomer thereof as described herein, or a combination thereof, or a pharmaceutically acceptable salt, hydrate, N-oxide, or solvate thereof, by determining whether the subject is responsive to a therapy that utilizes the compound, by determining the level of at least one of the BCL-2 family protein in the subject and comparing to a normal control sample, wherein an elevated level is indicative of a subject responsive to the therapy that the compound, or a pharmaceutically acceptable salt, hydrate, N-oxide, or solvate thereof, wherein the determination is made based on a sample from the subject.

In another aspect the disclosure provides methods for determining whether a subject is responsive to a therapy that utilizes a compound or stereoisomer thereof as described herein, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof.

In another aspect the disclosure provides methods for determining whether a subject is responsive to a therapy that utilizes a compound or stereoisomer thereof as described herein, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, wherein the determination is made based on a sample from the subject.

In another aspect the disclosure provides methods for determining whether a subject is responsive to a therapy that utilizes a compound or stereoisomer thereof as described herein, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, wherein the sample is a biological fluid or tumor sample.

In another aspect the disclosure provides methods for determining whether a subject is responsive to a therapy that utilizes a compound or stereoisomer thereof as described herein, or a combination thereof, or a pharmaceutically acceptable salt, hydrate, N-oxide, or solvate thereof, by determining the level of at least one of the BCL-2 family protein in the subject and comparing to a normal control sample, wherein an elevated level is indicative of a subject responsive to the therapy that utilizes the compound, or a pharmaceutically acceptable salt, hydrate, N-oxide, or solvate thereof, wherein the BCL-2 family polynucleotide or polypeptide is selected from BCL-2, BCL-XL, BCL-W, MCL-1, and BCL-A1.

In another aspect the disclosure provides methods for inducing apoptosis in a cell having a level of at least one of the BCL-2 family protein member greater than levels in a control cell, by administering to the cell an effective amount of a compound of structure A, or a combination thereof, or a pharmaceutically acceptable salt, hydrate, N-oxide, or solvate thereof, to reduce the level of BCL-2 family protein(s) and induce apoptosis in the cell.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cancer cell.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cancer cell, wherein cancer is lung cancer, breast cancer, prostate cancer, or lymphomas.

In another aspect the disclosure provides methods for inducing apoptosis in a cell having a level of at least one of the BCL-2 family protein member greater than levels in a control cell, by administering to the cell an effective amount of a compound having structure A, or a combination thereof, or a pharmaceutically acceptable salt, hydrate, N-oxide, or solvate thereof, to reduce the level of BCL-2 family protein(s) and induce apoptosis in the cell, wherein the cell is a cell of the immune system.

In another aspect the disclosure provides methods for determining the effectiveness of a therapeutic regimen including administration of a compound or stereoisomer thereof as described herein, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof.

In another aspect the disclosure provides methods for determining the effectiveness of a therapeutic regimen including administration of a compound or stereoisomer thereof as described herein, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has cancer.

In another aspect the disclosure provides methods for determining the effectiveness of a therapeutic regimen including administration of a compound or stereoisomer thereof as described herein, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has cancer, wherein cancer is lung cancer, breast cancer, prostate cancer, or lymphomas.

In another aspect the disclosure provides methods for determining the effectiveness of a therapeutic regimen including administration of a compound or stereoisomer thereof as described herein, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has an autoimmune disorder.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor.

In another aspect the disclosure provides methods for treating a disease or a disorder, by administering to a subject in need thereof a therapeutically effective amount of a compound or stereoisomer thereof as described herein, or a combination thereof, or a pharmaceutically acceptable salt, hydrate, N-oxide, or solvate thereof, thereby treating the disease or the disorder, wherein the subject is afflicted with a condition wherein the condition is lupus erythmatosus, psoriasis, psoriatic arthritis, lupus nephritis, rheumatoid arthritis, multiple sclerosis, ulcerative colitis, myasthenia gravis, ITP, TTP, Grave's disease, Hashimoto's thyroiditis, Crohn's disease, autoimmune hemolytic anemias, insulin dependent diabetes mellitus, glomerulonephritis, rheumatic fever, osteoarthritis, gouty arthritis, dermatitis, bronchitis, rhinitis, asthma, Sjogrens' syndrome, meningitis, adrenoleukodystrophy, CNS vasculitis, mitochondrial myopathies, Amyotrophic Lateral Sclerosis, Alzheimer's disease, or a tumor, wherein the mitochondrial myopathy is MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, or combined systems disease (B12 deficiency).

In another aspect the disclosure provides methods for determining the effectiveness of a therapeutic regimen including administration of a compound or stereoisomer thereof as described herein, or a combination thereof, or a pharmaceutically acceptable salt, hydrate, N-oxide, or solvate thereof, in a subject by comparing the level of a BCL-2 family protein in a cell of the subject prior to and during treatment with the compound, or a pharmaceutically acceptable salt, hydrate, N-oxide, or solvate thereof, wherein a decreased level of BCL-2 family protein is indicative of effectiveness of the therapy that utilizes the compound, or a pharmaceutically acceptable salt, hydrate, N-oxide, or solvate thereof, wherein the subject has an autoimmune disorder, and administering a selective serotonin reuptake inhibitor (SSRI).

In another aspect the disclosure provides methods for treating inflammation in a subject, by administering to the subject in need of such treatment an anti-inflammatory agent is gossypol, apogossypol, L-apogossypol, derivatives or stereoisomers of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby.

In another aspect the disclosure provides methods for treating inflammation in a subject, by administering to the subject in need of such treatment an anti-inflammatory agent is gossypol, apogossypol, L-apogossypol, derivatives or stereoisomers of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), or derivatives of purpurogallin, to treat the inflammation thereby, and administering a selective serotonin reuptake inhibitor (SSRI).

In another aspect the disclosure provides methods for treating inflammation in a subject, by administering to the subject in need of such treatment an anti-inflammatory agent is a stereoisomer of apogossypol.

As mentioned herein, inflammation disorders may involve the activity of apoptotic regulators. Thus, it is desirable to identify compounds that modulate the activity of apoptotic regulators, such as BCL-2 proteins. Such compounds are described herein. In some embodiments, the binding of these compounds prevents the interaction of anti-apoptotic BCL-2 family members with pro-apoptotic BCL-2 family members, and thereby reduces the biological activity of anti-apoptotic BCL-2 family members. As a result, the compounds can be used to treat or prevent inflammatory disorders involving anti-apoptotic BCL-2 protein activity. In various embodiments, the compounds of interest comprise apogossypol, including (−) apogossypol substantially free of (+) apogossypol, as well as various derivatives of apogossypol and other related compounds described herein. Such compounds can be administered to a patient with a high susceptibility to developing a condition associated with inflammation, for example, lupus erythematosus, to reduce the likelihood that the patient will develop such conditions.

As shown herein, apogossypol is more efficacious than gossypol, yet less toxic. The aldehydes in gossypol make it compound reactive, thus effectively reducing the available concentrations of active drug and causing toxicity. Apogossypol, a gossypol analog without the problematic aldehydes, retains full activity against anti-apoptotic BCL-2-family proteins. Daily dosing studies, described in more detail in the Examples portion of the application, show that mice tolerate doses of apogossypol about 2-4-times higher than gossypol. Furthermore, the studies show that apogossypol is superior to parent compound gossypol with respect to toxicology and efficacy.

In the general structure B shown herein, some specific $R^6$, $R^8$, $R^9$ and $R^{10}$ groups that may be used include, independently, hydrogen, —OH, —OCH$_3$, —CF$_3$, —CH$_3$, —OC$_2$H$_5$, —OC(O)CH$_3$, F, Cl, or Br. Some specific $R^7$ groups that may be used include, independently, hydrogen, —C$_2$H$_5$; -i-Pr, n-Pr, n-Bu, t-Bu, i-Bu, s-Bu, or cyclohexyl.

In some embodiments the compound of the general structure B shown herein is apogossypol. The use of apogossypol for treating cancer is described in PCT Publication No. WO 2005/009434, filed Jun. 25, 2005, which is hereby incorporated by reference in its entirety.

One specific compound of the disclosure described the general structure B shown herein has each of $R^6$, $R^8$, $R^9$ as the acetate moiety (—OC(O)CH$_3$), has $R^7$ as i-Pr, and $R^m$ as —CH$_3$ (apogossypol hexacetate). This compound can also be used as pro-drug for oral administration of apogossypol. In another embodiment the compounds of the disclosure include compounds of formula B, where one of the $R^6$ groups is a group other than hydrogen. In one embodiment, the compound can be (−) apogossypol. In other embodiments, the compound can be (−) apogossypol, (+) apogossypol, racemic apogossypol, S-apogossypol, R-apogossypol, or mixtures thereof. In another embodiment, the compound is substantially pure (−)apogossypol. In some embodiments, (−) apogossypol is at least 80 percent of all macromolecular species in the composition, such as more than about 85%, 90%, 95%, and 99%. For example, (−) apogossypol may be purified to essential homogeneity, where the composition consists essentially of solely (−) apogossypol. In various embodiments, the compound is (−) apogossypol is substantially free of (+) apogossypol. In some embodiments the compound of the general structure B shown herein is compound XXI or XXII shown herein.

In one embodiment, the compound the general structure B shown herein contains about 50% or more by weight of the (−) enantiomer of apogossypol and about 50% or less by weight of (+) enantiomer of apogossypol. In certain embodiments, the compound contains about 60% or more by weight of the (−) enantiomer of apogossypol and about 40% or less by weight of (+) enantiomer of apogossypol. In some embodiments, the compound contains about 70% or more by weight of the (−) enantiomer of apogossypol and about 30% or less by weight of (+) enantiomer of apogossypol. In some embodiments, the compound contains about 80% or more by weight of the (−) enantiomer of apogossypol and about 20% or less by weight of (+) enantiomer of apogossypol. In some embodiments, the compound contains about 90% or more by weight of the (−) enantiomer of apogossypol and about 10% or less by weight of the (+) enantiomer of apogossypol. In some embodiments, the compound contains about 95% or more by weight of the (−) enantiomer of apogossypol and about 5% or less by weight of (+) enantiomer of apogossypol. In some embodiments, apogossypol contains about 99% or more by weight of the (−) enantiomer of apogossypol and about 1% or less by weight of (+) enantiomer of apogossypol.

The natural product Gossypol (1) is a potent inhibitor of Bcl-2, Bcl-X$_L$ and Mcl-1, functioning as a BH3 mimic. (−) Gossypol is currently in phase clinical II trail, displaying single-agent antitumor activity in patients with advanced malignancies. Given that Gossypol has toxicity problems likely due to two reactive aldehyde groups, we designed Apogossypol (2), a compound that lacks these aldehydes, but retains activity against anti-apoptotic Bcl-2 family proteins in vitro and in cells. Recently, we also compared the efficacy and toxicity in mice of Gossypol and Apogossypol. Our preclinical in vivo data show that Apogossypol has superior efficacy and markedly reduced toxicity compared to Gossypol. We also evaluated the single-dose pharmacokinetic characteristics of Apogossypol in mice. Apogossypol displayed superior blood concentrations over time compared to Gossypol, due to slower clearance. These observations indicate that Apogossypol is a promising lead compound for cancer therapy. Recently, we reported the separation and characterization of Apogossypol atropoisomers. These studies revealed that the racemic Apogossypol is as effective as its individual isomers. We further reported the synthesis and evaluation of 5,5' ketone substituted Apogossypol derivatives and the best compound 3 (BI79D10) displayed improved in vitro and in vivo efficacy compared to Apogossypol. However, compound 3 displayed mild GI toxicity during the course of transgenic mice studies while Apogossypol show no significant sign of toxicity which is likely due to relatively active ketone groups in compound 3. In turn, we now place our attention on preparing and evaluating activities of novel 5,5' substituted Apogossypol derivatives which replace reactive ketone groups with more druggable amide and alkyl groups at 5,5' position.

Apogossypol is a promising inhibitor of Bcl-$X_L$ and Bcl-2 with improved in vivo efficacy and reduced toxicity compared to Gossypol. Molecular docking studies of Apogossypol into the BH3 binding groove in Bcl-2 suggest that Apogossypol forms two hydrogen bonds with residues Arg 143 and Tyr 105 in Bcl-2 through 1 and 1' hydroxyl group, respectively. Apogossypol also forms hydrogen bonds with Trp141 and Tyr 199 in Bcl-2 through 6' hydroxyl group on the right naphthalene ring. The isopropyl group on the left naphthalene ring inserts into the first hydrophobic pocket (P1) in Bcl-2, while the isopropyl group on the right naphthalene ring inserts into the hydrophobic pocket (P2). Analysis of the predicted binding models indicates that while the overall core structure of Apogossypol fits rather well into BH3 binding groove of Bcl-2, the two isopropyl groups do not apparently fully occupy the hydrophobic pockets P1 and P2. Therefore, a library of 5,5' substituted Apogossypol derivatives that replace the isopropyl groups with suitable substituents was designed with the aim of deriving novel molecules that could occupy the hydrophobic pockets on Bcl-2 more efficiently.

A synthetic route was developed to install variety of amide groups at 5,5' position. Compound 1 (Gossypol) was treated with NaOH solution at 90° C. to provide compound 2 (Apogossypol), which was readily methylated by dimethyl sulfate in the presence of potassium carbonate to afford compound 4. Reaction of compound 4 with $TiCl_4$ followed by dichloromethyl methyl ether at room temperature resulted in loss of isopropyl groups and simultaneous bisformylation to give aldehyde compound 5. The aldehyde groups of compound 5 were convert to carboxylic acid 6 by mild oxidation with sodium hypochlorite. The carboxylic acid 6 was then coupled with a variety of commercially available amines in the presence of 1-ethyl-3-(3'-dimethylaminopropyl)carbodiimide (EDCI) at room temperature to give compound 7. Subsequent demethylation of the compound 7 using boron tribromide afforded compound 8. The synthesis of 5,5' alkyl substituted Apogossypol derivatives were outlined in FIGS. 12 and 16-18. Compound 5 was treated with different Grignard or lithium reagents to afford a secondary alcohol 9, which was oxidized to give the phenone 10 by pyridinium chlorochromate. Triethylsilane reduced phenone 10 to alkyl compound 11 followed by subsequent demethylation using boron tribromide to afford compound 12. Compounds 13 and 14, with hydrogen atom or carboxylic acid at 5,5' positions, were synthesized to explore if substitution at 5,5' position is important for enhancing biological activities. Compound 13 was synthesized by treating compound 4 with concentrated sulfuric acid to lose isopropyl group. The resulting product and compound 6 was then treated individually with boron tribromide to give compounds 13 and 14, respectively.

The synthesized 5,5' substituted Apogossypol derivatives were first screened by one-dimensional $^1H$ nuclear magnetic resonance spectroscopy (1D-$^1H$ NMR) binding assays against Bcl-$X_L$. Active compounds in 1D-$^1H$ NMR binding assays were then selected and evaluated in Isothermal Titration calorimetry assays (ITC), cell viability assays and competitive fluorescence polarization assays (FPA). A group of compounds (8r, 8q, 8m) displayed high binding affinity for Bcl-$X_L$ in these assays. The most potent compound 8r induced significant chemical shift changes in active site methyl groups (region between −0.38 and 0.42 ppm) in the one-dimensional $^1H$-NMR spectra of Bcl-$X_L$ and also has an $IC_{50}$ value of 0.76 μM in the FP displacement assays, which is 5 times more effective than Apogossypol. To confirm results of the NMR binding data and the FP assays, we further evaluated the binding affinity of compound 8r for Bcl-$X_L$ using ITC assay. In agreement with NMR binding and FPA data, compound 8r displayed potent binding affinity to Bcl-$X_L$ with a $K_d$ value of 0.11 μM, which is 15 times more potent than Apogossypol ($K_d$=1.7 μM) in the same assay. Consistent with NMR binding, FPA, and ITC data, compound 8r displayed strong efficacy in inhibiting cell growth in PC3ML cells, which express high levels of Bcl-$X_L$. The $EC_{50}$ value of 8r is 1.7 μM, hence 6 fold more potent than Apogossypol ($EC_{50}$=10.4 μM). Compounds (8j-8s) displayed similar binding affinity as 8r for Bcl-$X_L$ in these assays with average $IC_{50}$ value of 2.8 μM.

Bcl-2 and Mcl-1 play critical roles in cell apoptosis and Bfl-1 has been recently suggested to be an important anti-apoptotic factor in large B-cell lymphomas among Bcl-2 family proteins. Therefore we further evaluated the binding properties and specificity of selected Bcl-$X_L$ active 5,5' substituted Apogossypol derivatives against Bcl-2, Mcl-1 and Bfl-1 using FP assays. Compound 8r displayed strong binding affinity for Bcl-2, Mcl-1 and Bfl-1. It inhibited Bcl-2, Mcl-1 and Bfl-1 with $IC_{50}$ values of 0.32, 0.28 and 0.73 μM, respectively, which are approximately 10 times more potent than Apogossypol in similar FP assays. Compound 8r was further evaluated against H460, H1299 and BP3 cell lines, which express high levels of Bcl-2, Mcl-1 and Bfl-1, respectively. Consistent with FPA data, compound 8r displayed significant efficacy in inhibiting cell growth in H460 and BP3 cells with $IC_{50}$ value of 0.33 μM and 0.66 μM, respectively, which are approximately 7-10 times more potent than Apogossypol. Molecular docking studies of compound 8r demonstrated that 2-phenylpropyl groups at 5,5' positions inserted deeper into hydrophobic pockets (P1 and P2) in Bcl-2, hence occupying these regions more efficiently compared to isopropyl groups of Apogossypol. In addition, the carbonyl group on the right naphthalene ring also formed an additional hydrogen bond with residue Tyr199. However, compound 8r displayed similar cell activity in H1299 cell line compared to Apogossypol which is probably because different cell lines have different sensitivities for compound 8r. Other 5,5' substituted Apogossypol derivatives, such as 12e, 8n, 8p, 8q, 8k also displayed strong pan-active inhibitory properties against Bcl-2, Mcl-1 and Bfl-1. The most potent compound 8q bound to Bcl-2, Mcl-1 and Bfl-1 with $IC_{50}$ value of 0.67, 0.59 and 1.3 μM, respectively, in FP assays. In agreement with FPA, it show potent cell inhibition activity for H460, H1299 and BP3 cell lines with $IC_{50}$ value of 0.40, 0.36 and 0.20 μM, respectively.

Analysis of structure-activity relationship (SAR) of synthesized 5,5' substituted Apogossypol derivatives reveals that substitution at 5,5' position are important for achieving stronger binding affinity to Bcl-2 family proteins. Accordingly compounds 13 and 14 with hydrogen atoms or carboxylic acid groups on 5,5' positions, displayed weak or no inhibition in all assays. Analysis of SAR of 5,5' amide substituted Apogossypol derivatives further indicates that longer and flexible hydrophobic groups show better efficacy than small, short and rigid hydrophobic groups. Replacement of small methylcyclopropane (8l) or short cyclopentyl (8b) group by longer methylcyclohexyl group (8m) significantly increased cell inhibition potency. Also, compounds (8n-8s) having phenethyl groups at 5,5' positions displayed potent cell activity in the H460 and PC3ML cell lines with average $EC_{50}$ values of 0.64 µM and 2.6 µM, respectively while compounds (8a-8e) having phenyl group displayed relatively weak cell activity with average $EC_{50}$ values of 8.6 µM and 11.3 µM, respectively. Based on our modeling prediction, this is likely because longer and flexible groups could insert deeper into the P1 and P2 pockets. We also explored the SAR of the 5,5' alkyl substituted Apogossypol derivatives. In general, longer hydrophobic groups also show improved potency. Compounds 12a and 12b with isobutyl and isopentyl groups displayed improved activity compared to Apogossypol with isopropyl groups. Again, compound 12e with phenethyl group are more active than compound 12d with benzyl group.

The H460 cell line has been studied by several groups. A pan-Bcl-2 family inhibitor, GX15-070, was tested in H460 cell line with an $IC_{50}$ value of 3.85 µM. BP3 is human diffuse large B-cell lymphoma (DLBCL) cell line overexpressing Bfl-1. The mRNA ratio of Bfl-1, Bcl-$X_L$ and Mcl-1 is approximately 10:3:1. We determined that BP3 cell overexpressed high level Bfl-1 and Mcl-1 by Western blot analysis as shown below in Table 1.

TABLE 1

| | Mcl-1 | Bcl-2 | Bcl-xl | Bfl-1 |
|---|---|---|---|---|
| BP3 | +++ | No | + | +++ |
| RS4; 11 | No | ++++ | + | No |

4-point rating scale for western data:
++++: Very high level
+++: High level
++: Medium level
+: Low
No: Not Detectable The potent Bcl-$X_L$ and Bcl-2 antagonist ABT-737 displayed no cell activity against BP3 cell lines because ABT737 is not effective against Mcl-1 and Bfl-1.

Hence, we next evaluated the ability of 5,5' substituted Apogossypol derivatives to induce apoptosis of the human lymphoma RS11846 cell line, which expresses high levels of Bcl-2 and Bcl-$X_L$. For these assays, we used Annexin V-FITC and propidium iodide (PI) double staining, followed by flow-cytometry analysis. Most of synthesized Apogossypol derivatives effectively induced apoptosis of the RS11846 cell line in a dose-dependent manner. In particular, compounds 8q, 8r and 8n are effective with $EC_{50}$ values ranging from 3.0 to 5.8 µM, which is consistent with previous results in human cancer PC3ML and H460 cell lines. Again, the negative control compounds 13 and 14 induced weak or no apoptosis of the RS11846 cell line.

We also explored whether 5,5' substituted Apogossypol derivatives had cytotoxicity against Bax/Bak double knockout (DKO) mouse embryonic fibroblast cells (MEF) in which antiapoptotic Bcl-2 family proteins lack a cytoprotective phenotype. Some potent pan-active Bcl-2 compounds (8m, 8q, 8r, 8k, 8p, 12e) displayed slightly cytotoxicity in Bax/Bak double knockout mouse embryonic fibroblast cells (MEF/DKO) by killing 20-35% of them at 10 µM using FITC-Annexin V/PI assays, implying that those compounds displayed some off-target effects. However, those compounds displayed reduced off-target effects than Gossypol which displayed very similar cytotoxicity in MEF and MEF/DKO cells at 10 µM. In comparison, Apogossypol had reduced off-target effect but displayed weaker ability to induce apoptosis of the MEF cells compared to 5,5' amide substituted Apogossypol derivatives.

Apogossypol is a polyphenol scaffold with 6 hydroxyl groups on the naphthalene ring which can be oxidized to quinones. We previously stabilized Apogossypol by cocrystallizing it with ascorbic acid. Apogossypol can also be stabilized by introducing electron withdrawing groups, such as carbonyl groups on the naphthalene rings because these will decrease the electron density on the naphthalene ring and subsequently slow down oxidation rate and other side reactions. The chemical stability of solid compounds (8m, 8q, 8r, 8k, 8p, 12e) was evaluated at room temperature. The stability of compound was monitored using a combination of HPLC and LCMS. Overall, 5,5' amide substituted Apogossypol derivatives show superior chemical stability compared to Apogossypol. In particular, 8r and 8q were 10% degraded after 60 days at room temperature while Apogossypol is almost 80% decomposed under same condition in the absence of ascorbic acid. Compound 12e having phenethyl group at 5,5' position are also less stable than amide compounds due to lack of electron withdrawing groups.

To test the pharmacological properties of 5,5' substituted Apogossypol derivatives, we determined their in vitro plasma stability, microsomal stability, and cell membrane permeability. From these studies, we could conclude that our synthesized compounds displayed superior plasma and microsomal stability than Apogossypol. Compounds 8r and 8m degraded 4% and 11%, respectively, after 1 hour incubation in rat plasma while Apogossypol degraded 47% under same condition. In addition, compounds 8r and 8m degraded 24% and 10%, respectively, after 1 hour incubation in rat microsomal preparations while Apogossypol degraded 36% under same condition. Compounds 8r and 8m also showed similar or improved cell membrane permeability compared to Apogossypol.

Hence, using a combination of 1D $^1$H-NMR binding assays, FP assays, ITC assays, cytotoxicity assays and preliminary in vitro ADME data, compounds such as 8r and 8q were selected for further in vivo studies using B6Bcl-2 transgenic mice. B-cells of the B6Bcl-2 transgenic mice overexpress human Bcl-2 and accumulate in the spleen of mice. The spleen weight is used as an end-point for assessing in vivo activity as we determined that the spleen weight is highly consistent in age- and sex-matched Bcl-2-transgenic mice and variability was within ±2% among control B6Bcl2 mice. We first screened the in vivo activities of compounds such as 8r and 8q side by side with Apogossypol and Gossypol in a single Bcl-2 transgenic mouse with a single intraperitoneal (ip) injection at 72 µmol/kg. In agreement with all in vitro data, tested 5,5' amide substituted Apogossypol derivatives displayed superior in vivo activity compared to Apogossypol and Gossypol. In particular, compounds (8r, 8k and 8p) induced more than 40% spleen weight reduction. Since the maximum spleen shrinkage would be no more than 50% in this experimental model, these compounds induced near maximal (85-95%) biological activity while Apogossypol and Gossypol induced 40% of maximum reduction in spleen weight at same dose. Again, the negative control, compound 13 displayed no activity in transgenic mice model, as expected. Overall tested 5,5' alkyl substituted Apogossypol derivatives (12c and 12e) displayed lower in vivo activity compared to 5,5' amide substituted Apogossypol derivatives. However, the 5,5' alkyl substituted Apogossypol show no significant signs of toxicity at 72 µmol/kg and even at 120 µmol/kg while 5,5' amide substituted Apogossypol show toxicity signs at 72 µmol/kg as shown below in Table 2.

TABLE 2

| | 2 | 1 | 13 | 12e | 8k | 8m | 8p | 8q | 8r | 12c |
|---|---|---|---|---|---|---|---|---|---|---|
| Effica | PR | PR | NR | PR | CR | PR | CR | PR | CR | PR |
| Tox | 0 | 2+ | 0 | 0 | 4+ | 4+ | 4+ | 4+ | 3+ | 1+ |

Toxicity Rating Scale:
4+ (lethal),
3+: severe,
2+: moderate,
1+: mild,
0: No toxicity The mice treated with compound 8r had more apparent signs of GI toxicity at 72 μmol/kg (50 mg/kg). In order to balance the toxicity and efficacy of compound 8r, we next explored the maximum tolerated dose (MTD) of 8r using a group of five mice. Mice were treated with a single dose of 100, 75, 50, 25 and 12.5 mg/kg (ip) and observed for a period of 14 days monitoring morbidity (body weight loss) and mortality. All mice were alive after 14 days and the maximum weight loss was observed at the fifth day which underwent 80-100% recovery after 14 days. The mice dosed at 25 and 12.5 mg/kg showed no weight loss while the mice dosed at 50 mg/kg displayed around 13% weight loss. Therefore the MTD of compound 8r is likely between 25 mg to 50 mg/kg, approximately. We next evaluated the in vivo activity and toxicity of the compound 8r in groups of six mice each at dose of 42 mg/kg (60 μmol/kg). Consistent with the single mouse experiment, compound 8r treatment of these mice resulted in a significant (~70%) reduction of spleen weight (P<0.0001) compared to the control group of six mice. All mice tolerated the treatment well and mild signs of GI toxicity were observed. The average weight loss of mice was 7.8% during the course of this study with 8r.

In summary, a library of 5,5' substituted Apogossypol derivatives was synthesized and evaluated in a variety of in vitro and in vivo assays. The most potent compound, 8r, was found to bind to Bcl-$X_L$, Bcl-2, Mcl-1 and Bfl-1 with $IC_{50}$ values of 760 nM, 320 nM, 280 nM and 730 nM, respectively. The compound also potently inhibited growth in cell cultures of the PC3ML, H460, H1299 and BP3 cancer cell lines, which express Bcl-$X_L$, Bcl-2, Mcl-1 and Bfl-1, respectively, with $EC_{50}$ values in the submicromolar to nanomolar range. Compound 8r effectively induced apoptosis of the RS11846 human lymphoma cell line in a dose-dependent manner and show little cytotoxicity against Bax/Bak double knockout mouse embryonic fibroblast cells in which antiapoptotic Bcl-2 family proteins lack a cytoprotective phenotype, implying that compound 8r has little off-target effects. Finally, compound 8r showed favorable chemical stability, in vitro ADME properties and superior in vivo efficacy compared to Apogossypol in Bcl-2 transgenic mice in which Bcl-2 is overexpressed in B-cells. Considering the critical roles of anti-apoptotic Bcl-2 family proteins in tumorgenesis, chemoresistance, and the potent inhibitory activity of 8r against anti-apoptotic Bcl-2 family proteins, compound 8r res a viable drug candidate for the development of novel apoptosis-based cancer therapies.

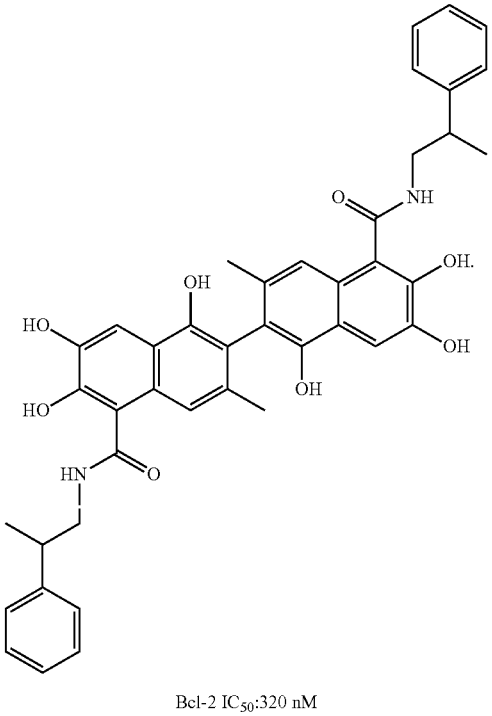

8r

Bcl-2 $IC_{50}$:320 nM

TABLE 3

EVALUATION OF 5, 5' SUBSTITUTED APOGOSSYPOL DERIVATIVES USING A COMBINATION OF 1D $^1$H-NMR BINDING ASSAYS AND CELL VIABILITY ASSAYS

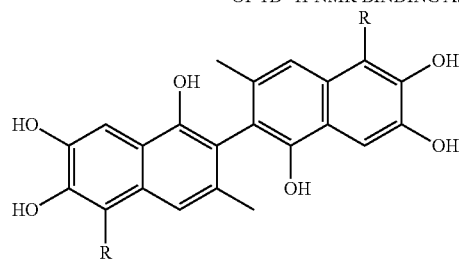

| Compound | R = | 1D-$^1$H NMR$^{a*}$ | RS11846$^{c*}$ | H1299$^{b*}$ | H460$^{b*}$ | PC3ML$^{b*}$ | BP3$^{c*}$ |
|---|---|---|---|---|---|---|---|
| Gossoypol (1) | | +++ | 4.2 | 6.0 | 3.0 | 3.1 | 1.42 |
| Apogossypol (2) | | ++ | 5.0 | 3.4 | 3.5 | 10.4 | 4.7 |
| 14 | COOH | − | >30 | >30 | >30 | >30 | >30 |

$EC_{50}$ (μM) spans the six rightmost columns.

TABLE 3-continued

EVALUATION OF 5, 5' SUBSTITUTED APOGOSSYPOL DERIVATIVES USING A COMBINATION OF 1D $^1$H-NMR BINDING ASSAYS AND CELL VIABILITY ASSAYS

| Compound | R = | 1D-$^1$H NMR$^{a}$* | EC$_{50}$ (μM) | | | | |
|---|---|---|---|---|---|---|---|
| | | | RS11846$^{c}$* | H1299$^{b}$* | H460$^{b}$* | PC3ML$^{b}$* | BP3$^{c}$* |
| 8a | phenyl-NH-C(O)-CH$_3$ | + | 15.1 | 8.0 | 3.5 | 15.1 | ND$^{d}$* |
| 8b | cyclopentyl-NH-C(O)-CH$_3$ | + | 13.7 | 8.0 | 8.5 | 12.2 | ND |
| 8c | 4-phenoxyphenyl-NH-C(O)-CH$_3$ | + | 10.8 | 17.0 | 10.1 | 8.5 | ND |
| 8d | 4-ethylphenyl-NH-C(O)-CH$_3$ | + | 4.7 | 5.0 | 4.1 | 8.3 | ND |
| 8e | 3-(trifluoromethyl)phenyl-NH-C(O)-CH$_3$ | + | 12.6 | 28.7 | 16.7 | 12.2 | ND |
| 8f | 1-phenylpropyl-NH-C(O)-CH$_3$ | +++ | 4.2 | ND | 1.5 | ND | ND |
| 8g | benzyl-NH-C(O)-CH$_3$ | + | 9.3 | 3.6 | 4.6 | 13.7 | ND |
| 8h | 3-methylbenzyl-NH-C(O)-CH$_3$ | +++ | 4.8 | 3.1 | 2.9 | 10.2 | ND |

TABLE 3-continued

EVALUATION OF 5, 5' SUBSTITUTED APOGOSSYPOL DERIVATIVES USING A COMBINATION OF 1D $^1$H-NMR BINDING ASSAYS AND CELL VIABILITY ASSAYS

| Compound | R = | 1D-$^1$H NMR[a]* | RS11846[c]* | H1299[b]* | H460[b]* | PC3ML[b]* | BP3[c]* |
|---|---|---|---|---|---|---|---|
| 8i | 3-chlorobenzyl acetamide | +++ | 7.3 | 5.2 | 3.3 | 8.3 | ND |
| 8j | 2,4,6-trimethylbenzyl acetamide | ++ | 3.0 | 3.6 | 1.4 | 0.7 | 1.5 |
| 8k | 1-(4-chlorophenyl)ethyl acetamide | +++ | 5.5 | 3.2 | 0.50 | 5.0 | 1.5 |
| 8l | cyclopropylmethyl acetamide | + | >10 | ND | ND | ND | ND |
| 8m | cyclohexylmethyl acetamide | +++ | 4.9 | 4.8 | 0.41 | 3.7 | 0.90 |
| 8n | phenethyl acetamide | ++ | 3.1 | 3.6 | 0.55 | 3.9 | 0.72 |
| 8o | 3-methylphenethyl acetamide | + | 5.6 | ND | 0.70 | ND | ND |
| 8p | 3-chlorophenethyl acetamide | +++ | 4.6 | 7.8 | 0.99 | 3.2 | 0.41 |
| 8q | 4-ethylphenethyl acetamide | +++ | 3.0 | 0.36 | 0.40 | 1.7 | 0.2 |

TABLE 3-continued

EVALUATION OF 5, 5' SUBSTITUTED APOGOSSYPOL DERIVATIVES USING A COMBINATION OF 1D $^1$H-NMR BINDING ASSAYS AND CELL VIABILITY ASSAYS

| Compound | R = | 1D-$^1$H NMR[a]* | RS11846[c]* | H1299[b]* | H460[b]* | PC3ML[b]* | BP3[c]* |
|---|---|---|---|---|---|---|---|
| | | | EC$_{50}$ (μM) | | | | |
| 8r | (2-phenylpropyl)acetamide | ++ | 5.8 | 3.2 | 0.33 | 1.7 | 0.66 |
| 8s | (indan-2-yl)acetamide | ++ | 4.1 | 7.1 | 0.94 | 3.0 | 1.1 |
| 8t | (4-chlorophenethyl)acetamide | ++ | 5.1 | ND | 1.3 | ND | 0.70 |

[a]*4-point-rating scale:
+++, Very Active;
++, Active;
+, Mild;
−, Weak
[b]*Compounds against cell line using ATP-LITE assay
[c]*Compounds against cell line using Annexin V-FITC and propidium iodide assay
[d]*ND: not determined

TABLE 4

EVALUATION OF 5, 5' SUBSTITUTED APOGOSSYPOL DERIVATIVES USING A COMBINATION OF 1D $^1$H-NMR BINDING ASSAYS AND CELL VIABILITY ASSAYS

| Compound | R = | 1D-$^1$H NMR[a]* | R511846[c]* | H1299[b]* | H460[b]* | PC3ML[b]* | BP3[c]* |
|---|---|---|---|---|---|---|---|
| | | | EC$_{50}$ (μM) | | | | |
| Apogossypol (2) | isobutyl | ++ | 5.0 | 3.4 | 3.5 | 10.4 | 4.7 |
| 13 | H | − | 24.5 | 13.4 | >10 | >10 | ND[d]* |

TABLE 4-continued

EVALUATION OF 5, 5' SUBSTITUTED APOGOSSYPOL DERIVATIVES USING A
COMBINATION OF 1D $^1$H-NMR BINDING ASSAYS AND CELL VIABILITY ASSAYS

| Compound | R = | 1D-$^1$H NMR$^{a}$* | R511846$^{c}$* | H1299$^{b}$* | H460$^{b}$* | PC3ML$^{b}$* | BP3$^{c}$* |
|---|---|---|---|---|---|---|---|
| 12a | sec-butyl (CH₃, H₃C) | + | 8.4 | 1.2 | 3.2 | 6.7 | ND |
| 12b | isopentyl | + | 4.8 | 1.8 | 1.1 | 5.2 | ND |
| 12c | cyclopentylmethyl | + | 4.5 | 10.9 | 1.8 | 11.2 | ND |
| 12d | benzyl | + | 3.2 | 1.28 | 1.2 | 8.3 | ND |
| 12e | phenylpropyl | ++ | 9.8 | 0.58 | 0.92 | 2.4 | 4.14 |

$^{a}$*4-point-rating scale:
+++: Very Active;
++: Active;
+: Mild;
−: Weak
$^{b}$*Compounds against cell line using ATP-LITE assay
$^{c}$*Compounds against cell line using Annexin V-FITC and propidium iodide assay
$^{d}$*ND: not determined

TABLE 5

CROSS-ACTIVITY OF SELECTED 5,5' SUBSTITUTED APOGOSSYPOL DERIVATIVES AGAINST BCL-X$_L$, BCL-2, MCL-1 and BFL-1

| Compound | IC$_{50}$ (μM) FPA | | | | K$_d$ (μM) ITC |
|---|---|---|---|---|---|
| IC$_{50}$ | Bcl-X$_L$ | Bcl-2 | Mcl-1 | Bfl-1 | Bcl-X$_L$ |
| Apogossypol (2) | 3.7 | 4.3 | 2.6 | >10 | 1.7 |
| 12e | 3.5 | 0.48 | 0.83 | 5.0 | 0.41 |
| 8m | 1.1 | 0.71 | 0.78 | 2.0 | 0.85 |
| 8n | 0.80 | 0.15 | 0.30 | 0.55 | ND |
| 8p | 6.3 | 4.4 | 3.2 | ND$^{a}$* | ND |
| 8q | 0.93 | 0.67 | 0.59 | 1.3 | 0.12 |
| 8j | 0.8 | 0.70 | 1.1 | ND | ND |
| 8k | 0.27 | 0.49 | 0.23 | 0.40 | 0.11 |
| 8r | 0.76 | 0.32 | 0.28 | 0.73 | 0.11 |
| 8s | 0.85 | 0.70 | 0.35 | 0.67 | ND |

ND$^{a}$* = Not determined

TABLE 6

PLASMA STABILITY, MICROSOMAL STABILITY, AND CELL PERMEABILITY OF SELECTED 5,5' SUBSTITUTED APOGOSSYPOL DERIVATIVES

| Compound | Plasma stability (T = 1 h) | Microsomal Stability (T = 1 h) | Cell Permeability |
|---|---|---|---|
| Apogossypol (1) | 53% | 64% | −7.16 |
| 12e | 80% | 89% | −6.61 |
| 12c | 81% | 75% | −6.27 |
| 8n | 63% | 60% | −6.49 |
| 8m | 89% | 90% | −6.67 |
| 8p | ND$^{a}$* | 90% | −7.71 |
| 8q | 94% | 87% | −8.15 |
| 8r | 96% | 76% | −7.51 |
| 8k | 94% | 71% | −7.92 |

ND$^{a}$* = Not determined

Binding of the compounds disclosed herein to anti-apoptotic BCL-2 proteins can induce apoptosis and thereby treat inflammation and/or inflammatory disorders. In some embodiments, the compounds disclosed herein can bind to anti-apoptotic BCL-2 family proteins such as, for example, BCL-2 or BCL-$X_L$. This binding can inhibit binding of the anti-apoptotic BCL-2 family members to pro-apoptotic BCL-2 family members. In various embodiments, binding of the compounds disclosed herein can reduce the formation of complexes between anti-apoptotic BCL-2 proteins and the BH3 domain of pro-apoptotic BCL-2 family members.

Guided by a combination of nuclear magnetic resonance (NMR) binding assays and computational docking studies, a series of 5,5' substituted Apogossypol derivatives were synthesized as potent pan-active inhibitors of anti-apoptotic Bcl-2 family proteins. One of the most potent compound, 8r, inhibits the binding of BH3 peptides to Bcl-$X_L$, Bcl-2, Mcl-1 and Bfl-1 with $IC_{50}$ values of 0.76 µM, 0.32 µM, 0.28 µM and 0.73 µM, respectively. This compound also potently inhibits cell growth in the H460 human lung cancer and BP3 human B-cell lymphoma cell lines with $EC_{50}$ values of 0.33 µM and 0.66 µM, respectively. Compound 8r effectively induces apoptosis of the RS11846 human lymphoma cell line in a dose-dependent manner and shows little cytotoxicity against $bax^{-/-}bak^{-/-}$ cells in which antiapoptotic Bcl-2 family proteins lack a cytoprotective phenotype, implying that compound 8r has little off-target effect. Compound 8r also displays in vivo efficacy in transgenic mice in which Bcl-2 is overexpressed in splenic B-cells. Together with its improved chemical, plasma and microsomal stability relative to Apogossypol, Compound 8r res a novel apoptosis-based therapy for cancer.

According to other embodiments, the disclosure provides a method for treating a disease or disorder. The method can include administering to a subject in need of such treatment, an effective amount of any herein described compound, or pharmaceutically acceptable salts, hydrates, or solvates thereof. Non-limiting examples of the diseases or disorders that can be treated are cancer and autoimmune diseases.

According to another embodiment, the disclosure provides a method for treating cancer. The method comprises administering to a subject in need thereof a therapeutically effective amount of any abo herein described compound, or pharmaceutically acceptable salts, hydrates, or solvates thereof. Any herein described compound may be used for treating any type of cancer. In some aspects, the kinds of cancer that may be treated include lung cancer, breast cancer, prostate cancer, as well as a variety of lymphomas.

According to another embodiment, any of the disclosed compound can be used for the manufacture of a medicament for the treatment of a pathological condition or symptom in a mammal, such as a human. The medicament can be directed to the treatment of cancer, within the limitations described herein.

According to another embodiment, the disclosure provides pharmaceutical compositions. The pharmaceutical compositions may comprise any of the disclosed compounds, or pharmaceutically acceptable salts, hydrates, or solvates thereof, and a pharmaceutically acceptable diluent or carrier. The pharmaceutical compositions can be used to treat cancer. The pharmaceutical compositions can further optionally include one or more additional therapeutic anti-cancer agents, including, but not limited to, such agents as (1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); (2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); (3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; (4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); (5) enzymes, including, L-asparaginase, and hydroxyurea, etc.; (6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); (7) platinum compounds (e.g., Cisplatin and Carboplatin, etc.); (8) monoclonal antibodies conjugated with anticancer drugs, toxins, and/or radionuclides, etc.; (9) biological response modifiers (e.g., interferons [e.g., IFN-.alpha., etc.] and interleukins [e.g., IL-2, etc.], etc.); (10) adoptive immunotherapy; (11) hematopoietic growth factors; (12) agents that induce tumor cell differentiation (e.g., all-trans-retinoic acid, etc.); (13) gene therapy agents; 14) antisense therapy agents; (15) tumor vaccines; (16) agents directed against tumor metastases (e.g., Batimistat, etc.); (17) inhibitors of angiogenesis, and (18) selective serotonin reuptake inhibitors (SSRI's).

Reactive, but non-limiting examples of suitable SSRIs that may be used include sertraline (e.g., sertraline hydrochloride, marketed under the trademark "Zoloft®" by Pfizer, Inc.) or sertraline metabolite, fluvoxamine (e.g., fluvoxamine melate, marketed under the trademark "Luvox®" by Solvay Pharmaceuticals, Inc.), paroxetine (e.g., paroxetine hydrochloride, marketed under the trademark "Paxil®" by SmithKline Beecham Pharmaceuticals, Inc.), fluoxetine (e.g., fluoxetine hydrochloride, marketed under the trademarks Prozac® or Sarafem® by Eli Lilly and Company) and citalopram (e.g., citalopram hydrobromide, marketed under the trademark "Celexa®" by Forest Laboratories, Parke-Davis, Inc.), and metabolites thereof. Additional examples include venlafaxine (e.g., venlafaxine hydrochloride marketed under the trademark "Effexor®" by Wyeth-Ayerst Laboratories), mirtazapine (e.g., marketed under the trademark "Remeron®" by Organon, Inc.), buspirone (e.g., buspirone hydrochloride marketed under the trademark "Buspar®" by Bristol-Myers Squibb), trazodone (e.g., trazodone hydrochloride marketed under the trademark "Desyrel®" by Bristol-Myers Squibb and Apothecon), nefazadone (e.g., nefazodone hydrochloride marketed under the trademark "Serzon®" by Bristol-Myers Squibb), clomipramine (e.g., clomipramine hydrochloride marketed under the trademark "Anafranil®" by Novopharm, LTD, Ciba, and Taro Pharmaceuticals), imipramine (e.g., imipramine hydrochloride marketed under the trademark "Tofranil®" by Glaxo-Welcome, Inc.), nortriptyline (e.g., Nortriptyline hydrochloride marketed under the trademark "Nortrinel®" by Lundbeck), mianserine (e.g., marketed under the trademark "Tolvon®" by Organon, Inc.), duloxetine (e.g., duloxetine hydrochloride marketed by Eli Lilly and Company), dapoxetine (e.g., dapoxetine hydrochloride marketed by ALZA Corporation), litoxetine (e.g., litoxetine hydrochloride marketed by Synthelabo Recherche (L.E.R.S.), Bagneux, France.), femoxetine, lofepramine (e.g., marketed under the trademark "Gamonil®" by MERCK & Co., Inc.), tomoxetine (e.g., marketed by Eli Lilly and Company). The disclosure encompasses SSRIs that are currently used, or those later discovered or formulated. SSRIs, including those listed herein, may be administered orally in an amount between about 2 mg and about 2,500 mg daily.

In the broad sense, any cancer or tumor (e.g. hematologic and solid tumors) may be treated according to embodiments of the disclosure. Exemplary cancers that may be treated according to embodiments of the disclosure include, but are not limited to, head and neck cancer, brain cancer (e.g. glioblastoma multifoma) breast cancer, colorectal cancer, esophageal cancer, gastric cancer, hepatic cancer, bladder cancer, cervical cancer, endometrial cancer, lung cancer (non-small cell), ovarian cancer and other gynological cancers (e.g. tumors of the uterus and cervix), pancreatic cancer, prostate cancer, renal cancer, choriocarcinoma (lung cancer), skin cancer (e.g. melanoma, basal cell carcinoma), hairy cell leukemia, chronic lymphotic leukemia, acute lymphocytic leukemia (breast & bladder), acute myelogenous leukemia, meningeal leukemia, chronic myelogenous leukemia, and erythroleukemia. More commonly, the cancers treated include leukemia and B-cell cancers (e.g. lymphoma, multiple myeloma, and MDS.

Non-limiting examples of autoimmune diseases that can be treated using any herein described compound and methods of the disclosure include rheumatoid arthritis, psoriatic arthritis, juvenile idiopathic arthritis, multiple sclerosis, systemic lupus erythematosus, myasthenia gravis, juvenile onset diabetes, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, psoriasis, psoriasis inflammatory bowel disease, and asthma.

As discussed in more detail herein, some embodiments also provide methods for treating and/or prevention various inflammatory disorders, diseases and conditions. Such inflammatory disorders, diseases and conditions include, without limitation, systemic autoimmune diseases such as, for example, lupus erythematosus, rheumatoid arthritis, multiple sclerosis, and psoriasis; and organ specific autoimmune diseases such as, for example, ulcerative colitis, myasthenia gravis, Grave's disease, Hashimoto's thyroiditis, Crohn's disease, lupus nephritis, autoimmune hemolytic anemias, immune thrombocytopenic purpura (ITP), thrombotic thrombocytopenic purpura (TTP), insulin dependent diabetes mellitus, glomerulonephritis, and rheumatic fever. Other inflammatory diseases that may be treated in accordance with this disclosure include, without limitation, other inflammatory arthritic conditions such as psoriatic arthritis, osteoarthritis and gouty arthritis, as well as other inflammatory conditions such as conjunctivitis, dermatitis, bronchitis, rhinitis etc., brought about by injury, allergies, infections, microorganisms, trauma, or physical or chemical agents. The treatment of inflammatory aspects of asthma, Sjogrens' syndrome, meningitis, adrenoleukodystrophy, CNS vasculitis, mitochondrial myopathies, Amyotrophic Lateral Sclerosis, Alzheimer's disease, or tumors is also contemplated as part of this disclosure. Examples of mitochondrial myopathies include MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, and combined systems disease (B12 deficiency). In association with such prevention and/or treatment, articles of manufacture, compositions, methods of use, and medical treatments by the compounds described herein are also provided.

In some cases, it may be appropriate to administer any herein described compound as a salt. Examples of pharmaceutically acceptable salts include organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting any herein described compound with a suitable base affording a physiologically acceptable anion. Alkali metal (for example, sodium, potassium or lithium) or alkaline earth metal (for example calcium) salts of carboxylic acids can also be made.

Any tablets, troches, pills, capsules, and the like, which incorporate any herein described compound, may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When there is a unit dosage form of any herein described compound, it may contain, in addition to materials of the herein type, a liquid carrier, such as a vegetable oil or a polyethylene glycol. Various other materials may be as coatings or to otherwise modify the physical form of a solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, any herein described compound may be incorporated into sustained-release preparations and devices.

Any herein described compound may also be administered intravenously or intraperitoneally by infusion or injection. Solutions of any herein described compound may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations may contain a preservative to prevent the growth of microorganisms.

Sterile injectable solutions can be prepared by incorporating any herein described compound of in the sufficient therapeutic amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, any herein described compound may be applied in pure form, i.e., when it is a liquid. However, it will generally be desirable to administer it to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants and additional antimicrobial agents can be added to optimize the properties for a given use.

The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user, as known to those having ordinary skill in the art.

The disclosure also provides a pharmaceutical composition of the compounds described herein, or a pharmaceutically acceptable salt thereof, in combination with a pharmaceutically acceptable diluent or carrier. Further, the disclosure provides the use of compounds disclosed herein in combination with other known anti-inflammatory compounds.

In various embodiments, the disclosure provides a method for treating inflammatory disease and/or a condition associated with inflammation by administering to a mammal in need of such therapy, an effective amount of the compounds described herein, the compounds described herein in combination with an additional anti-inflammatory compound or a pharmaceutically acceptable salt thereof. In other embodiments, methods for the prevention of inflammatory disease and/or a condition associated with inflammation or a method for reducing the likelihood that a patient will develop such inflammation is provided. The methods can include administering to a mammal in need of such therapy, an effective amount of the compounds described herein or a pharmaceutically acceptable salt thereof.

There are also provided methods for treating a mammalian subject, particularly a human, suspected of having, or being prone to a disease or condition involving inflammation, by administering to a mammalian subject in need thereof a therapeutically effective amount of a compound by at least one of the compounds of the general structure B shown herein, a single enantiomer of a compound of the general structure B, a mixture of the (+) enantiomer and the (−) enantiomer, a mixture of about 90% or more by weight of the (−) enantiomer and about 10% or less by weight of the (+) enantiomer, an individual diastereomer of a compound of the general structure B, a mixture of diastereomers, or a pharmaceutically acceptable salt, solvate, or prodrug thereof, so as to affect treat or prevent inflammation. In some embodiments, the compound is apogossypol.

In some embodiments, the methods for treating inflammation or preventing inflammation include administration of an effective amount of another therapeutic agent useful for treating or preventing the diseases or disorders disclosed herein. In some embodiments, the time in which the therapeutic effect of the other therapeutic agent is exerted overlaps with the time in which the therapeutic effect of the apogossypol or derivative is exerted.

In some embodiments, the other therapeutic agent is an anti-inflammatory agent. Examples of anti-inflammatory agents suitable for use according to some embodiments disclosed herein include, but are not limited to, steroids (e.g., cortisol, cortisone, fludrocortisone, prednisone, methylprednisolone, 6-methylprednisone, triamcinolone, betamethasone or dexamethasone), nonsteroidal anti-inflammatory drugs (NSAIDS (e.g., aspirin, acetaminophen, tolmetin, salicylates, ibuprofen, mefenamic acid, piroxicam, nabumetone, rofecoxib, celecoxib, etodolac or nimesulide). For the treatment of lupus erythmatosus, for example, the compounds disclosed herein may also be administered in conjunction with anti-malarial drugs including, for example, hydroxychloroquinone or in conjunction with cytotoxic chemotherapies including, for example, azathioprine and cyclophosphamide.

In some embodiments, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine).

Another type of therapeutic agent useful in the combination treatment of the disclosure is an antibody such as a humanized monoclonal antibody. Non-limiting examples include, the anti-CD99 antibody. See, for example, U.S. Pat. No. 7,223,395; White et al., Annu Rev. Med., 52:125 (2001). Rituximab (Rituxan®; Genentech, South San Francisco, Calif.) is another therapeutic agent that is useful in a conjugate of the disclosure for treating rheumatoid arthritis. Another therapeutic agent useful in the disclosure also can be cytotoxic agents, which, as used herein, is any molecule that directly or indirectly promotes cell death. Specific anticancer agents include Flavopiridol, Adriamycin (doxorubicin), VP16 (Etoposide), Taxol (paclitaxel), cisplatin and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a.-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds useful in practicing the disclosure can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds may be systemically administered, e.g., orally, in combination with a pharmaceutically acceptable vehicle such as an inert diluent or an assimilable edible carrier. The route of administration is oral or intravenous. Other routes of administration include, for example, parental, intramuscular, topical and subcutaneous. The compounds may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Just as in case of the compounds of the general structure A, the compounds of the general structure B may be administered in a variety of ways. For example, the tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the herein type, a liquid carrier, such as a vegetable oil or a polyethylene glycol. Various other materials may be as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compounds may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders by the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be advisable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated herein, as required, followed by filter sterilization. In the case of sterile powders for the preparation of sterile injectable solutions, the methods of preparation are vacuum drying and the freeze drying techniques, which yield a powder of the active ingredient plus any additional desired ingredient in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of structures A or B to the skin are known in the art; for example, see U.S. Pat. Nos. 4,608,392, 4,992,478, 4,559,157, and 4,820,508.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds of the general structure B in a liquid composition, such as a lotion, may be between about 0.1 and about 25.0 mass %, such as between about 0.5 about 10.0 mass %. The concentration in a semi-solid or solid composition such as a gel or a powder may be between about 0.1 and about 5.0 mass %, such as between about 0.5 and 2.5 mass %.

The amount of the compound, or an active salt or derivative thereof, required for use in treatment will vary with the particular salt selected but also with the route of administration, the nature of the condition being treated and the age and condition of the patient and will be ultimately at the discretion of the attendant physician or clinician. In general, however, a suitable dose may be in the range of between about 0.2 and about 100.0 µmol/kg per day. In one embodiment, the dose can be, e.g., between about 0.2 to about 1.0 µmol/kg per day. In some embodiments, a suitable does may be in the rage of between about 0.5 and about 100 mg/kg, e.g., between about 10 and about 75 mg/kg of body weight per day, such as between about 3 and about 50 mg per kilogram body weight of the recipient per day, for example, in the range of between about 6 and about 90 mg/kg/day, such as in the range of between about 15 and about 60 mg/kg/day.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. Typically, the dose range of the composition administered to the patient can be between about 0.5 and about 1000 mg/kg of the patient's body weight, or between about 1 and about 500 mg/kg, or between about 10 and about 500 mg/kg, or between about 50 and about 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between about 0.1 mg and about 500 mg of each ingredient, such as between about 1 mg and about 250 mg, e.g. between about 5 and about 200 mg or an intravenous, subcutaneous, or intramuscular dose of each ingredient between about 0.01 mg and about 100 mg, such as between about 0.1 mg and about 60 mg, e.g. between about 1 and about 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, at a dose of each ingredient up to 400 mg per day. Thus, the total daily dosage by oral administration of each ingredient will typically be in the range between about 1 and about 2000 mg and the total daily dosage by parenteral administration will typically be in the range between about 0.1 and about 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, such as between 30-90%, e.g., between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In various embodiments, the compositions may, if desired, be ed in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions including a compound disclosed herein formulated in a compatible pharmaceutical carrier may also be prepared, placed in an appropriate container, and labeled for treatment of an indicated condition.

In various embodiments, compounds of the disclosure can be labeled using methods known in the art. One detectable group is a fluorescent group. Fluorescent groups typically produce a high signal to noise ratio, thereby providing increased resolution and sensitivity in a detection procedure. For example, the fluorescent group absorbs light with a wavelength above about 300 nm, such as above about 350 nm, e.g., above about 400 nm. The wavelength of the light emitted by the fluorescent group is above about 310 nm, such as above about 360 nm, e.g., above about 410 nm.

The fluorescent detectable moiety can be selected from a variety of structural classes, including the following non-limiting examples: 1- and 2-amino-naphthalene, p,p' diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

In various embodiments, the compounds can be labeled, where the labeling group spontaneously emits a signal, or generates a signal upon the introduction of a suitable stimulus. Labels, include atoms such as, for example, $^{13}C$, $^{15}N$, $^{19}F$, $^{1}H$ and the like. In various embodiments, the compound can be conveniently administered in unit dosage form; for example, containing between about 5 and about 1,000 mg, such as between about 10 and about 750 mg, e.g., between about 50 and about 500 mg of active ingredient per unit dosage form.

In some embodiments, the active ingredient can be administered to achieve peak plasma concentrations of the active compound of between about 0.5 and about 75 µM, such as between about 1 and about 50 µM, e.g., between about 2 and about 30 µM. This may be achieved, for example, by the intravenous injection of a 0.05 to 5% solution of the active ingredient, optionally in saline, or orally administered as a bolus containing about 1-100 mg of the active ingredient. Desirable blood levels can be maintained by, for example, continuous infusion to provide about 0.01-5.0 mg/kg/hr or by intermittent infusions containing about 0.4-15 mg/kg of the active ingredient(s).

The desired dose may conveniently be ed in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLES

Some aspects of the disclosure can be further illustrated by the following non-limiting examples.

Example 1

Molecular Modeling

Molecular modeling studies were conducted on a Linux workstation and a 64 3.2-GHz CPUs Linux cluster. Docking studies were performed using the crystal structure of BCL-$X_L$ in complex with Bak-derived peptide (Protein Data Bank code 1BXL). The docked structures of 5,5' substituted Apogossypol derivatives in the peptide-binding pocket were obtained by ChemScore as the scoring function in the GOLD docking program. The protein surface was prepared with the program MOLCAD as implemented in Sybyl (Tripos, St. Louis). Docking studies were also performed using the crystal structure of Bcl-2 in complex with a benzothiazole BH3 mimetic ligand (Protein Data Bank code 1YSW). The ligand was extracted from the protein structure and was used to define the binding site for small molecules. Apogossypol and its derivatives were docked into the Bcl-2 protein by the GOLD docking program using ChemScore as the scoring function. The active site radius was set at 10 Å and 10 GA solutions were generated for each molecule. The GA docking procedure in GOLD allowed the small molecules to flexibly explore the best binding conformations whereas the protein structure was static. The protein surface was prepared with the program MOLCAD[5] as implemented in Sybyl (Tripos, St. Louis) and was used to analyze the binding poses for studied small molecules.

Example 2

General Chemical Procedures

Unless otherwise noted, all reagents and anhydrous solvents ($CH_2Cl_2$, THF, diethyl ether, etc) were obtained from commercial sources and used without purification. All reactions were performed in oven-dried glassware. All reactions involving air or moisture sensitive reagents were performed under a nitrogen atmosphere. Silica gel or reverse phase chromatography was performed using prepacked silica gel or C-18 cartridges (RediSep), repectively. All final compounds were purified to >95% purity, as determined by a HPLC Breeze from Waters Co. using an Atlantis T3 3 µM 4.6 mm×150 mm reverse phase column. Compounds for in vivo studies were purified again using preparative HPLC again to >99% purity. The eluant was a linear gradient with a flow rate of 1 ml/min from 50% A and 50% B to 5% A and 95% B in 15 min followed by 5 min at 100% B (Solvent A: $H_2O$ with 0.1% TFA; Solvent B: ACN with 0.1% TFA). Compounds were detected at λ=254 nm. NMR spectra were recorded on Varian 300 or Bruker 600 MHz instruments. Chemical shifts are reported in ppm (δ) relative to $^1H$ ($Me_4Si$ at 0.00 ppm). Coupling constant (J) are reported in Hz throughout. Mass spectral data were acquired on Shimadzu LCMS-2010EV for low resolution, and on an Agilent ESI-TOF for either high or low resolution.

Example 3

Synthesis of Compounds of the Disclosure

The synthesis for 5,5' substituted apogossypol derivatives is outlined below:

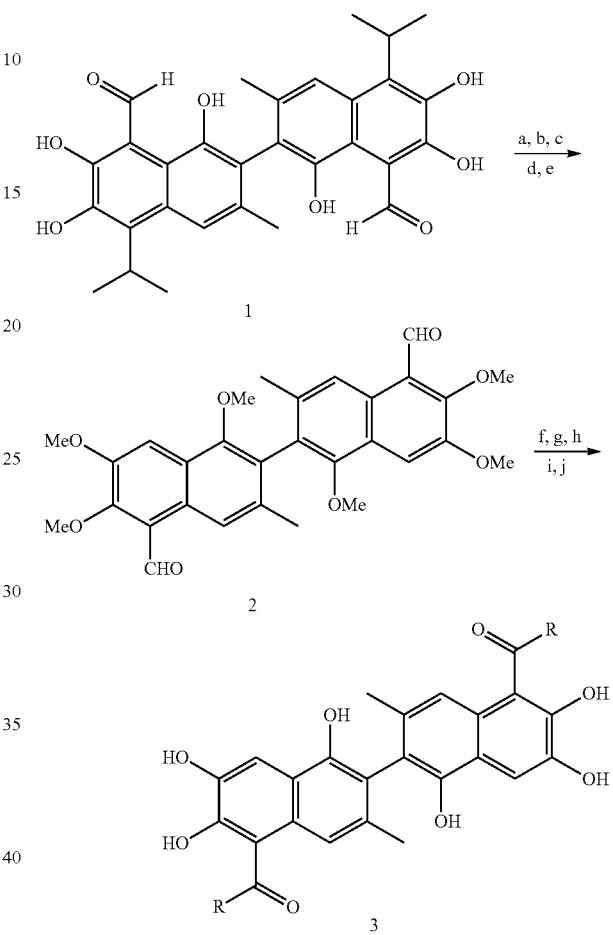

(a) NaOH, $H_2O$; (b) $H_2SO_4$; (c) DMS, $K_2CO_3$; (d) $TiCl_4$, $Cl_2CHOCH_3$; (e) HCl; (f) RMgBr or R Li; (g) $NH_4Cl$, $H2O$; (h) PCC, $CH_2Cl_2$; (i) $BBr_3$; (j) HCl.

Briefly and generally, gossypol 1 was treated with NaOH solution followed by dimethyl sulfate to afford methyl apogossypol. Reaction of methyl apogossypol with $TiCl_4$ and dichloromethyl methyl ether resulted in loss of isopropyl groups and simultaneous bisformylation to give aldehyde 2. The compound 2 was treated with different Grignard or lithium reagents to afford a secondary alcohol, which was oxidized to the phenone using pyridinium chlorochromate. Subsequent demethylation of the phenone afforded compound 3.

More specifically, the gossypol acetic acid 1 (5 g, 8.65 mmol) in 50 ml of 40% NaOH was heated under nitrogen at 90° C. for 3.5 hours in the dark. The reaction mixture was cooled and poured slowly onto ice (300 ml) and concentrated $H_2SO_4$ (35 ml) mixture to form white precipitation. The precipitation was filtered, washed with water and dried to afford apogossypol (3.8 g, 95%) as a white solid. $^1H$ NMR ($CDCl_3$ δ 7.61 (s, 2H), 7.50 (s, 2H), 5.93 (s, 2H), 5.27 (s, 2H), 5.13 (s, 2H), 3.88 (m, 2H), 2.12 (s, 6H), 1.55 (d, J=5.5 Hz, 12H).

Apogossypol (3.8 g, 8.21 mmol) was then dissolved into 200 ml acetone. $K_2CO_3$ (23.9 g, 206.7 mmol) and dimethyl sulfate (16.3 ml, 206.7 mmol) were added and the reaction mixture was refluxed under nitrogen for 24 hours. The solid that separated from the solution was collected by filtration. It was washed (acetone and water) and dried to yield 4.2 g of methylated apogossypol (93%). To a solution of methylated apogossypol (1.6 g, 2.93 mmol) in dry methyl chloride (40 ml) at 0° C. was added titanium tetrachloride (14.3 g, 75.5 mmol). After addition was completed, the dark red solution was stirred an additional 15 min at 0° C. Dichloromethyl methyl ether (2.93 g, 25.5 mmol) was added dropwise over 15 min, and the reaction mixture was stirred at ambient temperature under nitrogen for 14 hr.

The reaction mixture was poured onto ice and the resulting aqueous layer was extracted twice with methyl chloride. The combined organic fractions were washed with water and brine, dried over MgSO$_4$, and concentrated to give dark red oil. The oil was chromatographed (acetonitrile/methyl chloride) followed by trituration of crude product with diethyl ether to afford intermediate 2 (0.60 g, 40%) as a yellow solid.

For intermediate 2: $^1$H NMR: 8.47 (s, 1H), 7.29 (s, 1H), 7.05 (br s, 1H), 2.79 (t, J=7.35 Hz, 2H), 2.47 (s, 3H), 2.44 (s, 3H), 1.70 (m, 2H), 1.03 (t, J=7.35 Hz, 3H).

Example 4

Synthesis of Compound I of the Disclosure

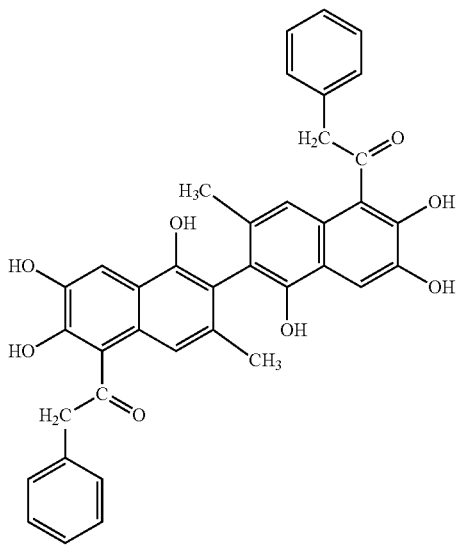

I

Compound I of the disclosure having the formula shown herein, also known as 1,1'-(1,1',6,6',7,7'-hexahydroxy-3,3'-dimethyl-2,2'-binaphthyl-5,5'-diyl)bis(2-phenylethanone), was synthesized as follows. To a freshly benzylmagnesium chloride (5.4 mmol) solution at room temperature was added a solution of aldehyde 2 (1.0 g, 1.93 mmol) in anhydrous tetrahydrofuran (15 ml) and the reaction mixture was stirred at this temperature for 12 hr. The reaction mixture was poured onto saturated ammonium chloride solution and the aqueous layer was extracted twice with diethyl ether, washed with brine and dried over MgSO$_4$. Filtration followed by evaporation of the ether gave yellow oil. The solution of yellow oil in dry methyl chloride (10 ml) was added into pyridinium chlorochromate (2.6 g, 12.1 mmol) in dry methyl chloride (12 ml). The reaction mixture was stirred at ambient temperature for 4 hr and was filtrated through celite The filtrate was chromatographed to afford 0.3 g of methylated compound I (22%). 0.27 mL of BBr$_3$ solution (0.72 g, 2.88 mmol) was added dropwise into a solution of methylated compound I (120 mg, 0.17 mmol) in 8 mL of anhydrous CH$_2$Cl$_2$ at −78° C. Stirring was continued at −78° C. for 1 hr, 0° C. for 1 hr, and ambient temperature for 1 hr. 50 grams of ice containing 10 mL of 6M hydrochloric acid was added to the mixture and stirred for one hour at room temperature. The aqueous layer was extracted with dichloromethane (3×30 mL). The combined organic layer was washed with water, brine and dried over MgSO$_4$. The solvent was concentrated in vacuo and the residue was purified by C-18 column chromatography (H$_2$O/Acetonitrile) to give 80 mg of compound c I (77%) as orange solid.

$^1$H NMR (CD$_3$OD) δ 7.61 (s, 2H), 7.30 (m, 8H), 7.22 (m, 2H), 6.97 (s, 2H), 4.40 (dd, J$_1$=15.6 Hz, J$_2$=22.8 Hz, 4H), 1.87 (s, 6H); $^{13}$C NMR (CD$_3$)$_2$SO) δ 204.6, 149.4, 144.8, 144.5, 135.4, 134.2, 130.5, 128.6, 126.9, 126.3, 122.6, 119.4, 116.8, 115.0, 107.1, 51.0, 21.1; HRMS calcd for [C$_{38}$H$_{30}$O$_8$+H] 615.2019; found 615.2013. HPLC is 99% pure.

Other derivatives encompassed by general structure A were synthesized and characterized. The synthesis followed the pattern described in Examples 3 and 4, with necessary adjustments, such as using different Grignard or lithium reagents when treating aldehyde intermediate compound 2. The spectral characteristics of the compounds were as follows (Roman numerals correspond to the herein described compounds of the disclosure).

Compound III. 1,1'-(1,1',6,6',7,7'-hexahydroxy-3,3'-dimethyl-2,2'-binaphthyl-5,5'-diyl)bis(2-methylpropan-1-one). $^1$H NMR (CDCl$_3$) δ 12.38 (s, 2H), 7.99 (s, 2H), 7.82 (s, 2H), 7.44 (s, 2H), 6.18 (s, 2H), 5.41 (s, 2H), 3.86 (m, 2H), 2.13 (s, 6H), 1.33 (d, J=9 Hz, 12H).

Compound XVIII. 1,1'-(1,1',6,6',7,7'-hexahydroxy-3,3'-dimethyl-2,2'-binaphthyl-5,5'-diyl)bis(2,2-dimethylpropan-1-one). $^1$H NMR (CD$_3$OD) δ 7.56 (s, 2H), 6.78 (s, 2H), 1.95 (s, 6H), 1.34 (m, 18H).

Compound IV. 1,1'-(1,1',6,6',7,7'-hexahydroxy-3,3'-dimethyl-2,2'-binaphthyl-5,5'-diyl)bis(3-methylbutan-1-one). $^1$H NMR (CD$_3$OD) δ 7.62 (s, 2H), 7.12 (s, 2H), 2.97 (d, J=6.6 Hz, 4H), 2.32 (m, 2H), 1.96 (s, 6H), 1.03 (d, J=3.6 Hz, 12H).

Compound XX. 1,1'-(1,1',6,6',7,7'-hexahydroxy-3,3'-dimethyl-2,2'-binaphthyl-5,5'-diyl)dipentan-1-one. $^1$H NMR (CD$_3$OD) δ 7.62 (s, 2H), 7.07 (s, 2H), 3.07 (t, J$_1$=J$_2$=6.6 Hz, 4H), 1.97 (s, 6H), 1.76 (m, 4H), 1.45 (m, 4H), 0.97 (t, J$_1$=J$_2$=6.6 Hz, 6H).

Compound XIX. 1,1'-(1,1',6,6',7,7'-hexahydroxy-3,3'-dimethyl-2,2'-binaphthyl-5,5'-diyl)bis(2-methylbutan-1-one). $^1$H NMR (CD$_3$OD) δ 7.62 (s, 2H), 7.05 (s, 2H), 3.43 (m, 2H), 1.96 (s, 6H), 1.50 (m, 4H), 1.21 (d, J=6.6 Hz, 6H), 0.99 (d, J=7.2 Hz, 6H).

Compound VII. (1,1',6,6',7,7'-hexahydroxy-3,3'-dimethyl-2,2'-binaphthyl-5,5'-diyl)bis(phenylmethanone). $^1$H NMR (CD$_3$OD) δ 7.89 (d, J=6.6 Hz, 4H), 7.67 (s, 2H), 7.62 (s, 2H), 7.49 (s, 4H), 6.82 (s, 2H), 1.93 (s, 6H).

Compound XVII. (1,1',6,6',7,7'-hexahydroxy-3,3'-dimethyl-2,2'-binaphthyl-5,5'-diyl)bis(benzo[d]thiazol-2-yl-methanone). $^1$H NMR (CD$_3$OD) δ 8.14 (d, J=4.8 Hz, 2H), 8.07 (s, 2H), 7.75 (s, 2H), 7.59 (t, J$_1$=J$_2$=2.4 Hz, 4H), 7.03 (s, 2H), 1.93 (s, 6H).

Compound VI. (1,1',6,6',7,7'-hexahydroxy-3,3'-dimethyl-2,2'-binaphthyl-5,5'-diyl)bis(cyclopentylmethanone). $^1$H NMR (CD$_3$OD) δ 7.62 (s, 2H), 7.05 (s, 2H), 3.84 (m, $J_1$=$J_2$=7.2 Hz, 2H), 2.03 (m, 4H), 1.99 (s, 6H), 1.93 (m, 4H), 1.77 (m, 4H), 1.67 (m, 4H).

Compound VIII. (1,1',6,6',7,7'-hexahydroxy-3,3'-dimethyl-2,2'-binaphthyl-5,5'-diyl)bis(naphthalen-1-ylmethanone). $^1$H NMR (CD$_3$OD) δ 8.97 (d, J=7.8 Hz, 2H), 8.07 (m, 2H), 7.98 (d, J=7.8 Hz, 2H), 7.68 (m, 8H), 7.43 (m, 2H), 6.95 (s, 2H), 1.79 (s, 6H).

Compound V. 1,1'-(1,1',6,6',7,7'-hexahydroxy-3,3'-dimethyl-2,2'-binaphthyl-5,5'-diyl)bis(3-ethylheptan-1-one). $^1$H NMR ((CD$_3$)$_2$SO) δ 10.08 (s, 2H), 9.26 (s, 2H), 8.08 (s, 2H), 7.53 (s, 2H), 6.91 (s, 2H), 2.87 (d, J=5.7 Hz, 4H), 1.98 (m, 2H), 1.85 (s, 6H), 1.30 (m, 16 H), 0.87 (t, $J_1$=$J_2$=7.5 Hz, 12H).

Compound IX. (1,1',6,6',7,7'-hexahydroxy-3,3'-dimethyl-2,2'-binaphthyl-5,5'-diyl)bis(biphenyl-4-ylmethanone). $^1$H NMR (CD$_3$OD) δ 7.97 (d, J=8.1 Hz, 4H), 7.70 (m, 10 H), 7.46 (m, 6H), 6.86 (s, 2H), 1.88 (s, 6H).

Compound X. (1,1',6,6',7,7'-hexahydroxy-3,3'-dimethyl-2,2'-binaphthyl-5,5'-diyl)bis((4-tert-butylphenyl)methanone). $^1$H NMR (CD$_3$OD) δ 7.82 (d, J=8.4 Hz, 4H), 7.65 (s, 2H), 7.51 (d, J=8.4 Hz, 4H), 6.80 (s, 2H), 1.86 (s, 6H), 1.34 (s, 18H).

Compound XI. (1,1',6,6',7,7'-hexahydroxy-3,3'-dimethyl-2,2'-binaphthyl-5,5'-diyl)bis((4-(trifluoromethyl)phenyl)methanone). $^1$H NMR (CD$_3$OD) δ 8.04 (d, J=7.8 Hz, 4H), 7.78 (d, J=7.8 Hz, 4H), 7.69 (s, 2H), 6.87 (s, 2H), 1.88 (s, 6H).

Compound II. (3,3'-dimethyl-2,2'-binaphthyl-1,1',6,6',7,7'-hexanol). $^1$H NMR (CD$_3$OD) δ 7.46 (s, 2H), 7.11 (s, 2H), 7.03 (s, 2H), 1.97 (s, 6H).

Compound XVI. 1,1'-(1,1',6,6',7,7'-hexahydroxy-3,3'-dimethyl-2,2'-binaphthyl-5,5'-diyl)bis(3-(4-fluorophenyl)propan-1-one). $^1$H NMR (CD$_3$OD) δ 7.62 (s, 2H), 7.27 (d, J=5.4 Hz, 4H), 6.97 (m, 4H), 6.88 (s, 2H), 3.40 (t, $J_1$=$J_2$=6.6 Hz, 4H), 3.10 (t, $J_1$=$J_2$=6.6 Hz, 4H), 1.90 (s, 6H).

Compound XII. 1,1'-(1,1',6,6',7,7'-hexahydroxy-3,3'-dimethyl-2,2'-binaphthyl-5,5'-diyl)bis(2-p-tolylethanone). $^1$H NMR (CD$_3$OD) δ 7.59 (s, 2H), 7.15 (d, J=8.1 Hz, 4H), 7.05 (d, J=8.1 Hz, 4H), 6.93 (s, 2H), 4.30 (dd, $J_1$=15.6 Hz, $J_2$=9.9 Hz, 4H), 2.27 (s, 6H), 1.85 (s, 6H).

Compound XV. 1,1'-(1,1',6,6',7,7'-hexahydroxy-3,3'-dimethyl-2,2'-binaphthyl-5,5'-diyl)bis(2-cyclohexylethanone). $^1$H NMR (CD$_3$OD) δ 7.61 (s, 2H), 7.10 (s, 2H), 2.95 (dd, $J_1$=3.3 Hz, $J_2$=3.0 Hz, 4H), 2.02 (m, 2H), 1.95 (s, 6H), 1.76 (m, 10H), 1.11 (m, 10H).

Compound XIII. 1,1'-(1,1',6,6',7,7'-hexahydroxy-3,3'-dimethyl-2,2'-binaphthyl-5,5'-diyl)bis(2-(3-bromophenyl)ethanone). $^1$H NMR (CD$_3$OD) δ 7.63 (s, 2H), 7.51 (s, 2H), 7.29 (m, 6H), 7.00 (s, 2H), 4.36 (dd, $J_1$=8.1 Hz, $J_2$=9.0 Hz, 4H), 1.91 (s, 6H).

Compound XIV. 1,1'-(1,1',6,6',7,7'-hexahydroxy-3,3'-dimethyl-2,2'-binaphthyl-5,5'-diyl)bis(2-(4-(trifluoromethoxy)phenyl)ethanone). $^1$H NMR (CD$_3$OD) δ 7.63 (s, 2H), 7.41 (d, J=4.2 Hz, 4H), 7.20 (d, J=4.2 Hz, 4H), 6.99 (s, 2H), 4.40 (dd, $J_1$=8.1 Hz, $J_2$=7.2 Hz, 4H), 1.88 (s, 6H).

Figure 12:
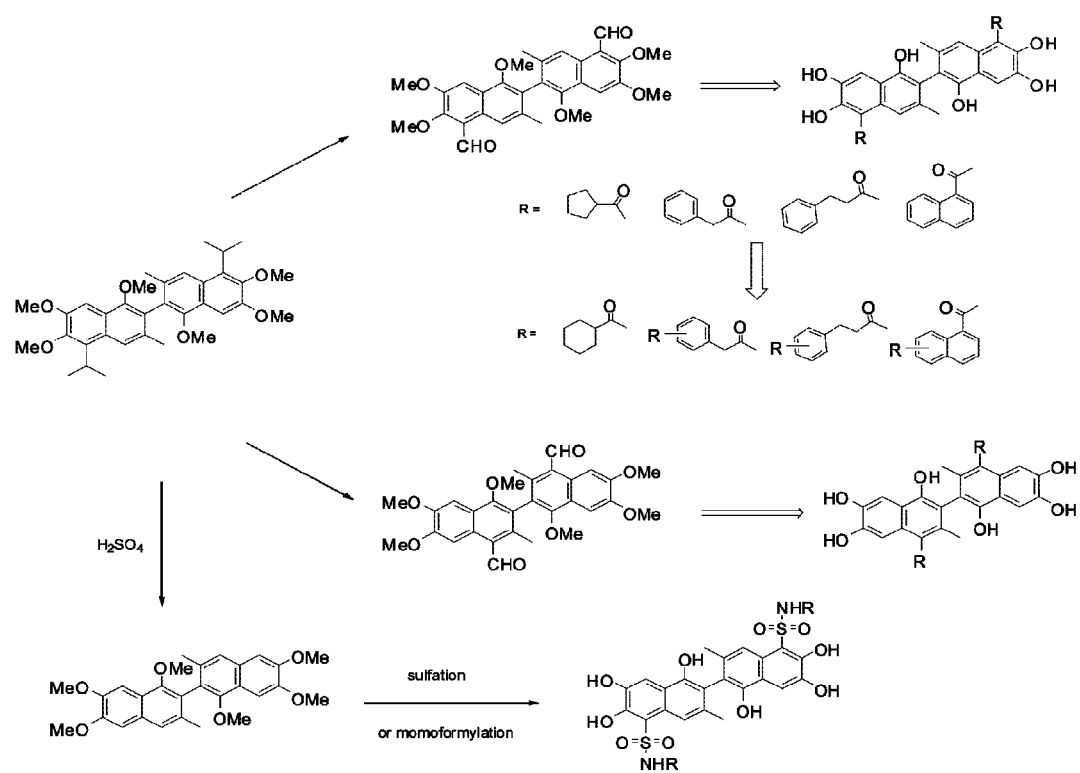
FIG. 12 shows a general synthetic scheme that can be used to synthesize some compounds of the disclosure.
Figure 13:
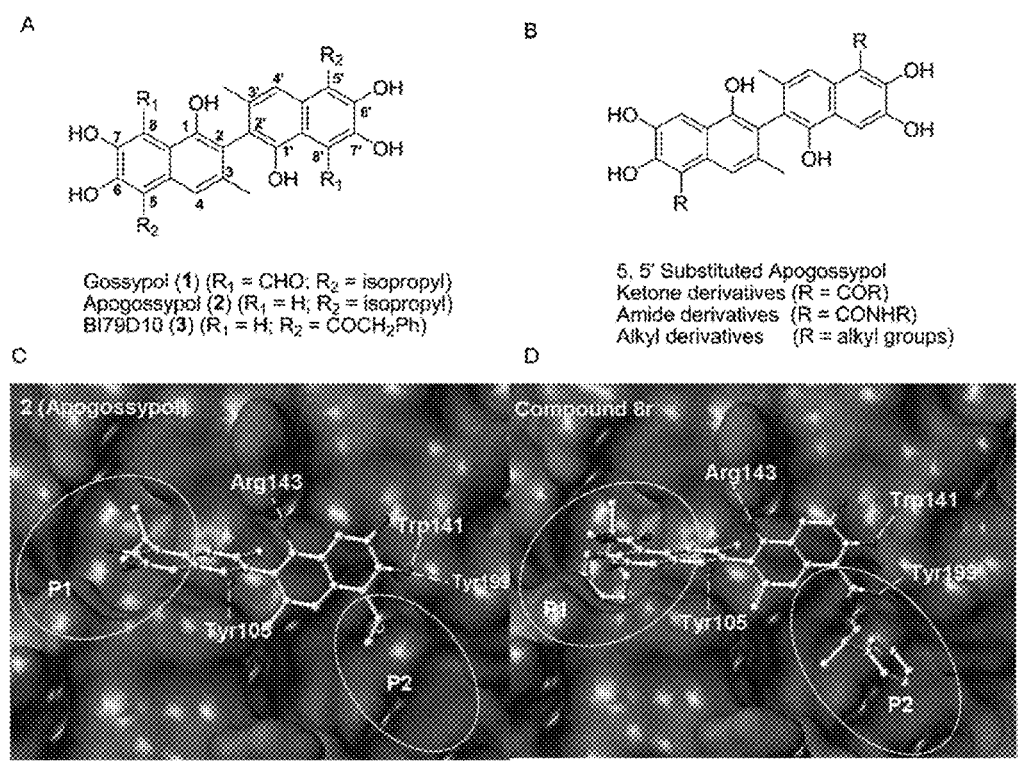
FIG. 13 shows: (A) Structure of Gossypol (1), Apogossypol (2) and BI79D10 (3). (B) Structure of 5,5' substituted Apogossypol derivatives. (C) and (D), Molecular docking studies. Stereo views of docked structures of (C) compound 2 (Apogossypol) and (D) compound 8r into Bcl-2 (PDB ID:1YSW).
Figure 14:
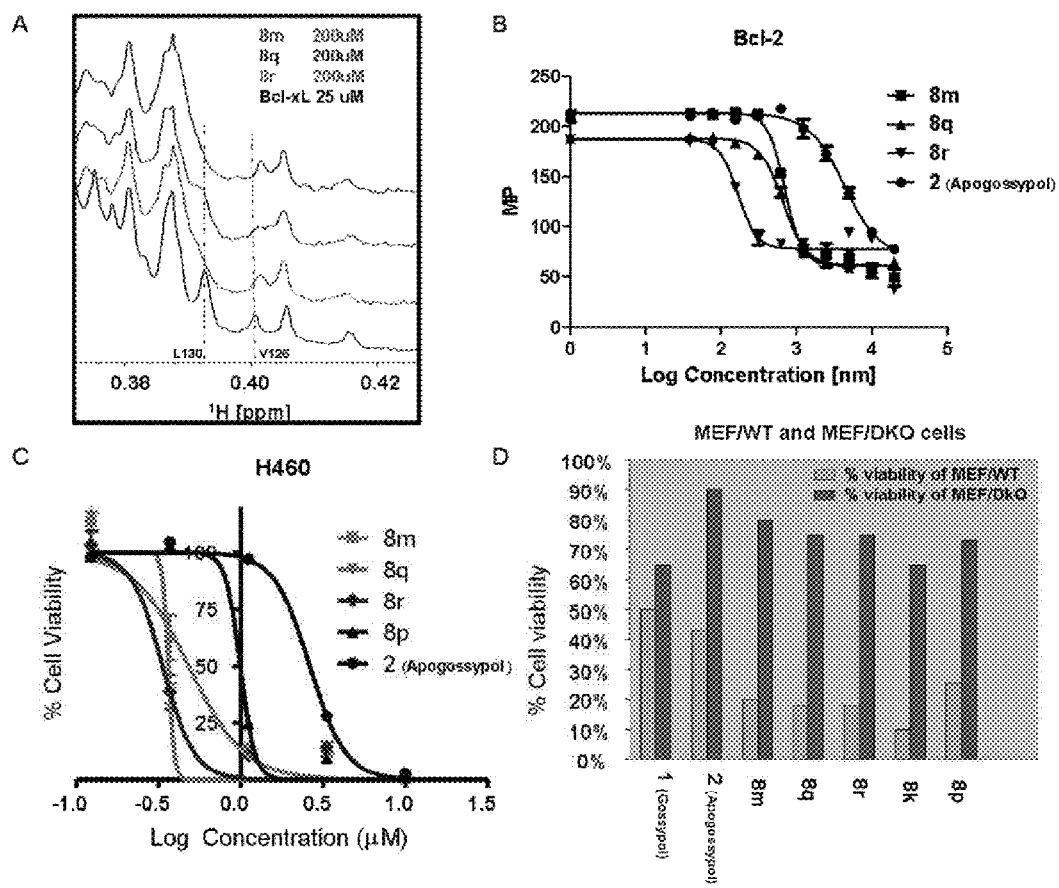
FIG. 14 shows: (A) NMR binding studies. Aliphatic region of the $^1$H-NMR spectrum of Bcl-$X_L$ (25 µM, black) and Bcl-$X_L$ in the presence of compound 8m (200 µM, grey), compound 8q (200 µM, blue), and compound 8r (200 µM, red). (B) Fluorescence polarization-based competitive binding curves of 8m (solid squares), 8q (solid up triangle), 8r (solid down triangle) and 2 (Apogossypol) (solid dots) using Bcl-2. (C) Inhibition of cell growth by compounds 8m (red square), 8q (green triangle), 8r (blue diamond), 8p (dark triangle) and 2 (Apogossypol) (dark dots) in the H460 human lung cell line. Cells were treated for 3 days and cell viability was evaluated using ATP-LITE assay. (D) Mouse embryonic fibroblast cells with wild-type (MEF/WT; blue bars) or bax$^{-/-}$ bak$^{-/-}$ double knockout (red bars) genotypes were treated with various 5,5' substituted Apogossypol derivatives at 10 µM and apoptosis was monitored by Annexin V-FITC assays.
Figure 15:
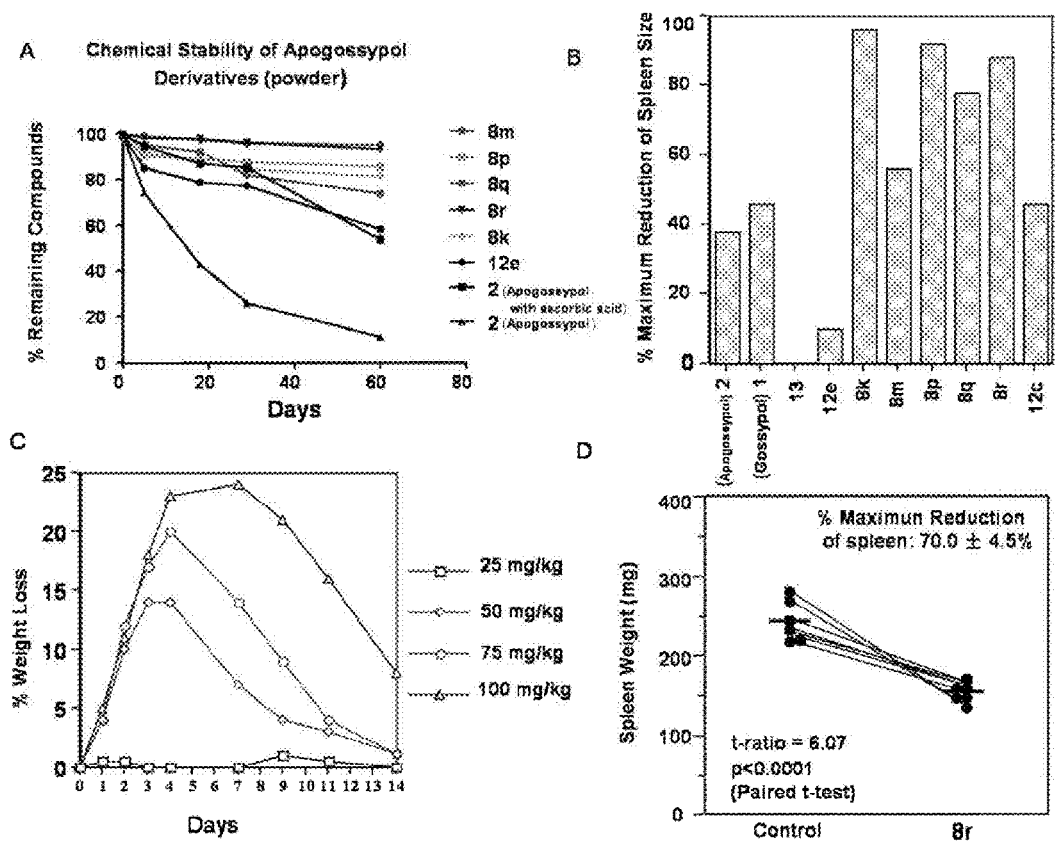
FIG. 15 shows: (A) Chemical stability of Apogossypol derivatives when left at room temperature in powder form: 8m (red dot), 8p (green square), 8q (purple dot), 8r (blue triangle), 8k (pink dot), 12e (dark dot), 2 (Apogossypol with ascorbic acid, dark square) and 2 (Apogossypol, dark triangle). Chemical stability was evaluated in the air for 60 days at room temperature. The stability was monitored using a combination of HPLC and LCMS. (B) Effects of 5,5' substituted Apogossypol derivatives on shrinkage of Bcl-2 mouse spleen at a single intraperitoneal injection dose of 0.072 mmol/kg. All shrinkage data are percentage of maximum reduction of mice spleen size. (C) % Weight loss in mice induced by single ip injection of various amount of compound 8r. (D) Effects of compound 8r at 42 mg/kg (0.06 mmol/kg) on reduction of spleen weight of six Bcl-2 mice treatment with a single intraperitoneal injection. Data shown as means±S.E. (n=6). P<0.0001.
Figure 16:
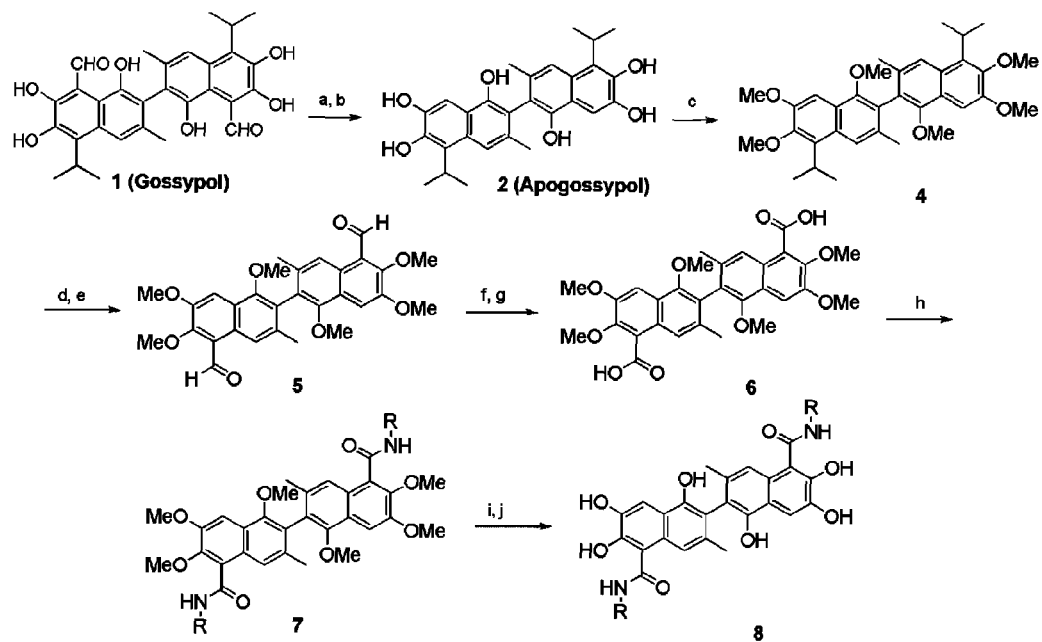
FIG. 16 shows a synthetic scheme that can be used to synthesize some of the compounds of the disclosure.
Figure 17:
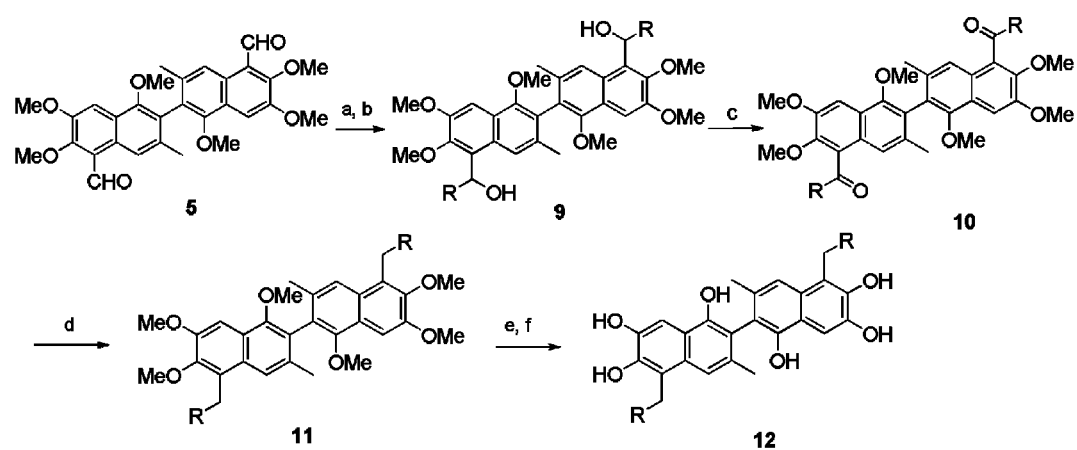
FIG. 17 shows a general synthetic scheme that can be used to synthesize some of the compounds of the disclosure.
Figure 18:
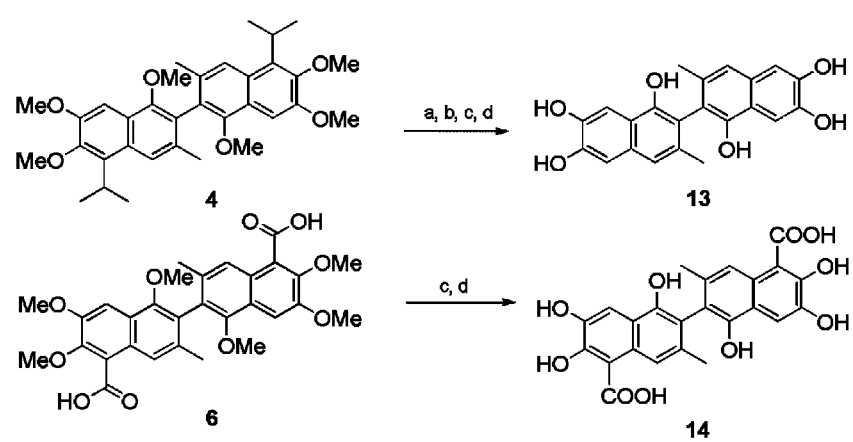
FIG. 18 shows a general synthetic scheme that can be used to synthesize some of the compounds of the disclosure.
Figure 19:
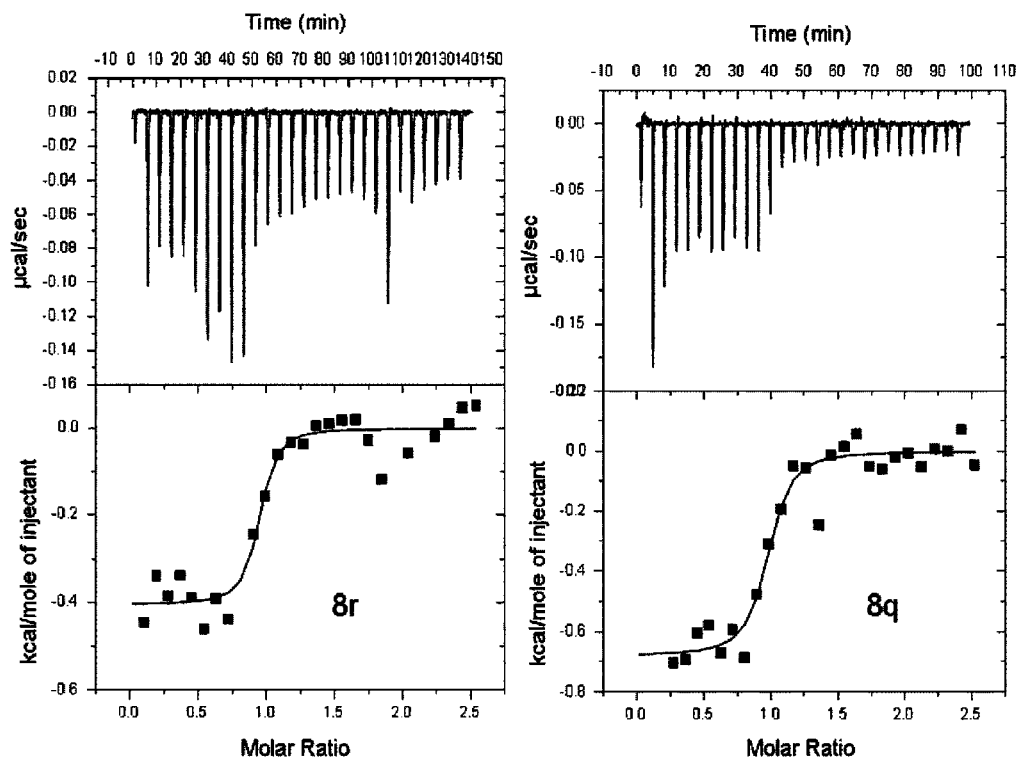
FIG. 19 shows the ITC studies of 5,5' substituted Apogossypol derivatives.
Figure 20:
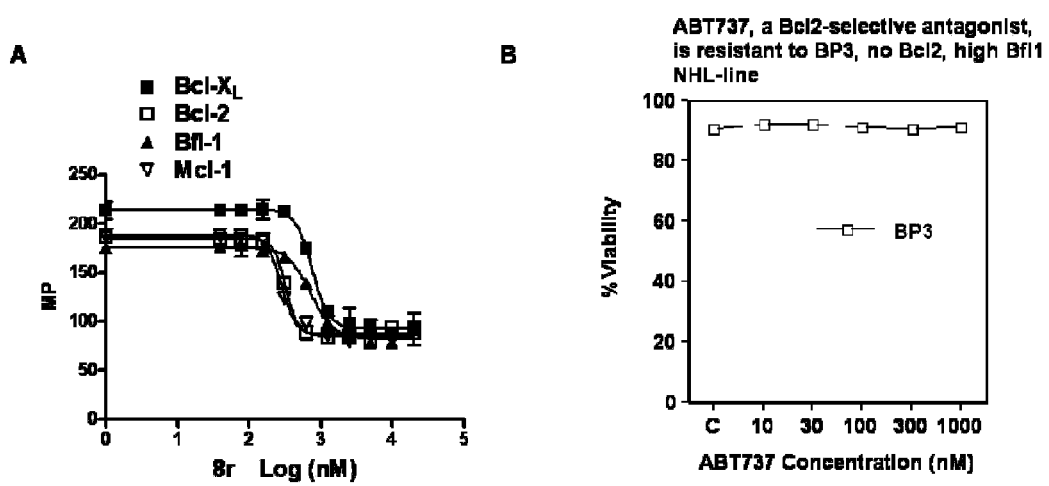
FIG. 20 shows: (A) Compound 8r competes with the binding of Bcl-2 family proteins to FITC-Bim BH3 peptide; (B) Cytotoxicity assays of ABT-737 against BP3 using Annexin V-FITC and propidium iodide assay.
Figure 21:
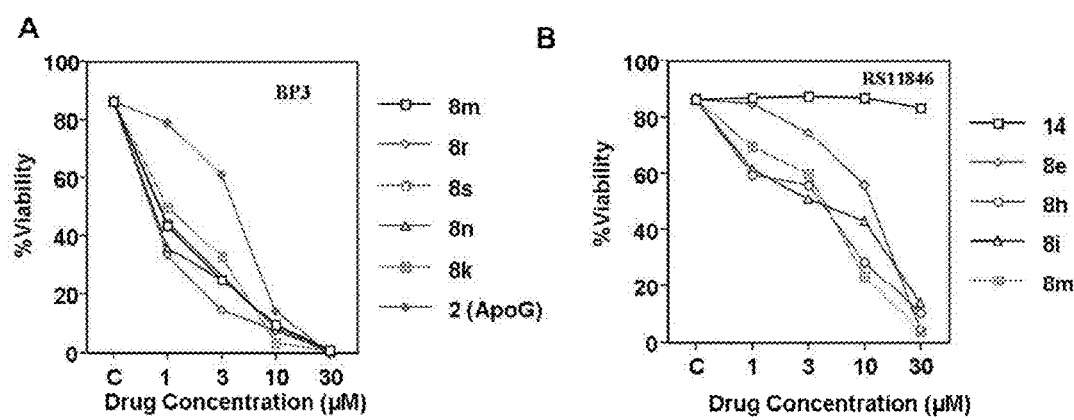
FIG. 21 shows the cytotoxicity assays of 5,5' substituted Apogossypol derivatives against (A) BP3 cell and (B) RS11846 cancer cell lines using Annexin V-FITC and propidium iodide assay.

Some compounds of the disclosure may be synthesized as shown on FIG. 12 (where R is CONX or CONR$_1$X, where R or R$_1$ is an alkyl, aromatic, or heterocyclic group, and X is an alkyl, a substituted alkyl, an aryl, a substituted aryl, an alkylaryl, and a heterocycle).

Further spectral data and the data on purity with respect to compounds of the disclosure are summarized in Table 7.

TABLE 7

HIGH RESOLUTION MASS (HRMS) AND HPLC PURITY OF 5,5' SUBSTITUTED APOGOSSYPOL DERIVATIVES

| Compound | Chemical Formula [M + H]$^+$ | HRMS Calculated | HRMS Found | HPLC Purity (%) |
|---|---|---|---|---|
| Gossypol | C$_{30}$H$_{31}$O$_8$ | NR | NR | 99.6 |
| Apogossypol | C$_{28}$H$_{31}$O$_6$ | 463.2115 | 463.2108 | 99.5 |
| III | C$_{30}$H$_{31}$O$_8$ | 519.2013 | 519.2013 | 99.5 |
| XVIII | C$_{32}$H$_{35}$O$_8$ | 547.2326 | 547.2327 | 99.3 |
| IV | C$_{32}$H$_{35}$O$_8$ | 547.2326 | 547.2326 | 99.3 |
| XX | C$_{32}$H$_{35}$O$_8$ | 547.2326 | 547.2324 | 97.1 |
| VII | C$_{36}$H$_{27}$O$_8$ | 587.1700 | 587.1702 | 99.4 |
| XVII | C$_{38}$H$_{25}$N$_2$O$_8$S$_2$ | 701.1047 | 701.1042 | 97.8 |
| VI | C$_{34}$H$_{35}$O$_8$ | 571.2326 | 571.2325 | 98.8 |
| VIII | C$_{44}$H$_{31}$O$_8$ | 687.2013 | 687.2027 | 97.2 |
| I | C$_{38}$H$_{31}$O$_8$ | 615.2013 | 615.2014 | 99.0 |
| V | C$_{40}$H$_{51}$O$_8$ | 659.3578 | 659.3583 | 98.8 |
| IX | C$_{48}$H$_{35}$O$_8$ | 739.2326 | 739.2323 | 99.5 |
| X | C$_{44}$H$_{43}$O$_8$ | 699.2952 | 699.2946 | 99.6 |
| XI | C$_{38}$H$_{25}$F$_6$O$_8$ | 723.1448 | 723.1447 | 99.6 |
| II | C$_{22}$H$_{19}$O$_6$ | 379.1176 | 379.1168 | 98.5 |
| XVI | C$_{40}$H$_{33}$F$_2$O$_8$ | 679.2138 | 679.2139 | 96.8 |
| XVII | C$_{40}$H$_{35}$O$_8$ | 643.2326 | 643.2328 | 98.6 |
| XV | C$_{38}$H$_{43}$O$_8$ | 627.2952 | 627.2949 | 98.6 |
| XIII | C$_{38}$H$_{29}$Br$_2$O$_8$ | 771.0224 | 771.0225 | 98.1 |
| XII | C$_{40}$H$_{29}$F$_6$O$_{10}$ | 783.1659 | 783.1651 | 95.6 |

Example 5

Synthesis of 5,5'-diisopropyl-3,3'-dimethyl-2,2'-binaphthyl-1,1',6,6',7,7'-hexanol (2)

The Gossypol acetic acid (1) (5 g, 8.65 mmol) in 50 ml of 40% NaOH was heated under nitrogen at 90° C. for 3.5 hours in the dark. The reaction mixture was cooled and poured slowly onto ice (300 ml) and concentrated H$_2$SO$_4$ (35 ml) mixture to form white precipitation. The precipitation was filtered, washed with water and dried to afford compound 2 (Apogossypol) (3.8 g, 95%) as a white solid. $^1$H NMR (CDCl$_3$) δ 7.61 (s, 2H), 7.50 (s, 2H), 5.93 (s, 2H), 5.27 (s, 2H), 5.13 (s, 2H), 3.88 (m, 2H), 2.12 (s, 6H), 1.55 (d, J=5.5 Hz, 12H).

Example 6

Synthesis of 5,5'-diisopropyl-1,1',6,6',7,7'-hexamethoxy-3,3'-dimethyl-2,2'-binaphthyl (4)

The compound 2 (Apogossypol) (3.8 g, 8.21 mmol) was dissolved into 200 ml acetone. K$_2$CO$_3$ (23.9 g, 206.7 mmol) and dimethyl sulfate (16.3 ml, 206.7 mmol) were added and the reaction mixture was refluxed under nitrogen for 24 hours. The solid was collected by filtration and washed using acetone and water and dried to yield 4.2 g of compound 4 as white solid (93%). $^1$H NMR (CDCl$_3$) 7.83 (s, 2H), 7.43 (s, 2H), 3.98 (m, 8H), 3.94 (s, 6H), 3.57 (s, 6H), 2.20 (s, 6H), 1.56 (s, 12H).

Example 7

Synthesis of 1,1',6,6',7,7'-hexamethoxy-3,3'-dimethyl-2,2'-binaphthyl-5,5'-dicarbaldehyde (5)

To a solution of compound 4 (1.6 g, 2.93 mmol) in dry methylene chloride (40 ml) at 0° C. was added titanium tetrachloride (14.3 g, 75.5 mmol). After addition was completed, the dark red solution was stirred an additional 15 min at 0° C. Dichloromethyl methyl ether (2.93 g, 25.5 mmol) was added dropwise over 15 min, and the reaction mixture was stirred at ambient temperature under nitrogen for 12 hours. The reaction mixture was poured onto ice and the resulting aqueous layer was extracted twice with methylene chloride. The combined organic fractions were washed with water and brine, dried over $MgSO_4$, and concentrated to give dark red oil. The oil was chromatographed (acetonitrile/methylene chloride) followed by trituration of crude product with diethyl ether to afford compound 5 (0.60 g, 40%) as yellow solid. $^1$H NMR ($CDCl_3$): 10.84 (s, 2H), 8.93 (s, 2H), 7.82 (s, 2H), 4.10 (s, 6H), 4.03 (s, 6H), 3.48 (s, 6H), 2.22 (s, 6H).

Example 8

Synthesis of 1,1',6,6',7,7'-hexamethoxy-3,3'-dimethyl-2,2'-binaphthyl-5,5'-dicarboxylic acid (6)

Compound 5 (6.6 g, 12.7 mmol) was dissolved in 40 ml of acetonitrile and 40 ml of THF in an ice bath. Sodium dihydrogen phosphate (876 mg, 6.35 mmol), 30% hydrogen peroxide (2.6 mL, 25.4 mmol) were added. Sodium chlorite (4.14 g, 45.8 mmol) dissolved in 20 ml of water was added. The reaction mixture was stirred overnight at room temperature and then poured onto 100 g of ice with 30 ml of 6M HCl. The solution was extracted with ether (3×100 mL). The ether extracts were washed with brine, dried over magnesium sulfate and filtered. Evaporation of the solvent in vacuo and the residue was purified by C-18 column chromatography ($H_2O$/Acetonitrile) to give 5.9 g (85%) of compound 6 as a red solid. $^1$H NMR ($CD_3OD$) δ 8.0 (s, 2H), 7.68 (s, 2H), 4.1 (s, 6H), 4.06 (s, 6H), 3.54 (s, 6H), 2.21 (s, 6H).

Example 9

Synthesis of 1,1',6,6',7,7'-hexamethoxy-3,3'-dimethyl-$N^5,N^{5'}$-bis(2-phenylpropyl)-2,2'-binaphthyl-5,5'-dicarboxamide (7r)

Compound 6 (500 mg, 0.907 mmol), EDCI (522 mg, 2.72 mmol) and HOBT (244 mg, 1.81 mmol) were dissolved in 15 ml of dry $CH_2Cl_2$ and stirred at room temperature for 10 minutes under nitrogen atmosphere. 2-phenyl-1-propanamine (0.30 ml, 2.09 mmol) and $Et_3N$ (0.51 ml, 3.7 mmol) were added and the reaction mixture was stirred at room temperature for 24 hours. The mixture was then poured onto 50 ml of water and the solution was extracted with $CH_2Cl_2$ (3×100 mL). The ether extracts were washed with water and brine, dried over magnesium sulfate and filtered. Evaporation of the solvent in vacuo and the residue was purified by silica chromatography to give 320 mg (45%) of compound 7r as a yellow solid. $^1$H NMR ($CD_3OD$) δ 7.56 (s, 2H), 7.37 (m, 8H), 7.22 (m, 4H), 3.98 (s, 6H), 3.85 (s, 6H), 3.77 (m, 2H), 3.62 (m, 2H), 3.55 (s, 3H), 3.53 (s, 3H), 3.20 (m, 2H), 2.01 (s, 3H), 2.00 (s, 3H), 1.38 (s, 3H), 1.39 (s, 3H).

Example 10

Synthesis of 1,1',6,6',7,7'-hexahydroxy-3,3'-dimethyl-$N^5,N^{5'}$-bis(2-phenylpropyl)-2,2'-binaphthyl-5,5'-dicarboxamide (8r)

0.45 ml of $BBr_3$ solution (1.18 g, 4.73 mmol) was added dropwise into a solution of compound 7 (310 mg, 0.40 mmol) in 20 ml of anhydrous $CH_2Cl_2$ at −78° C. Stirring was continued at −78° C. for 1 hour, 0° C. for 2 hours, and ambient temperature for 10 minutes. 50 grams of ice containing 10 ml of 6M HCl was added to the mixture and stirred for one hour at room temperature. The aqueous layer was extracted with dichloromethane (3×50 ml). The combined organic layer was washed with water, brine and dried over $MgSO_4$. The solvent was concentrated in vacuo and the residue was purified using C-18 column chromatography ($H_2O$/Acetonitrile) to give 200 mg of compound 8r (72%) as white-yellow solid. $^1$H NMR ($CD_3OD$) δ 7.56 (s, 2H), 7.37 (d, J=6.0 Hz, 4H), 7.32 (t, $J_1$=$J_2$=7.2 Hz, 4H), 7.20 (t, $J_1$=$J_2$=7.2 Hz, 2H), 7.06 (s, 1H), 6.98 (s, 1H), 3.75-3.59 (m, 4H), 3.19 (m, 2H), 1.88 (d, J=3.0 Hz, 3H), 1.88 (d, J=3.0 Hz, 3H), 1.41 (m, 6H).

Following the herein mentioned procedure and the appropriate starting materials and reagents used; compounds (7a-7t, 8a-8t and 14) were synthesized.

Example 11

Synthesis of 1,1',6,6',7,7'-hexamethoxy-3,3'-dimethyl-5,5'-diphenethyl-2,2'-binaphthyl (11e)

To a freshly benzylmagnesium chloride (5.4 mmol) solution at room temperature was added a solution of 5 (1.0 g, 1.93 mmol) in anhydrous tetrahydrofuran (15 ml) and the reaction mixture was stirred at this temperature for 12 hours. The reaction mixture was poured onto saturated ammonium chloride solution and the aqueous layer was extracted twice with diethyl ether, washed with brine and dried over $MgSO_4$. Filtration followed by evaporation of the ether gave yellow oil. The solution of yellow oil in dry methylene chloride (10 ml) was added into pyridinium chlorochromate (2.6 g, 12.1 mmol) in dry methylene chloride (12 ml). The reaction mixture was stirred at ambient temperature for 4 hours and was filtrated through celite. The filtrate was chromatographed to afford 0.3 g of 10e (22%). $^1$H NMR ($CDCl_3$) δ 7.54 (s, 2H), 7.32 (m, 10H), 7.14 (s, 2H), 4.29 (s, 4H), 4.02 (s, 6H), 3.96 (s, 6H), 3.49 (s, 6H), 2.02 (s, 6H). To a solution of compound 10e (170 mg, 0.29 mmol) in 10 ml TFA was added 0.6 ml of triethylsilane dropwise. The solution was stirred overnight at room temperature and concentrated in vacuo followed by silica gel column chromatography to give compound 11e as colorless oil (140 mg, 90%). $^1$H NMR ($CDCl_3$) δ 7.67 (s, 2H), 7.44 (s, 2H), 7.35 (s, 8H), 7.25 (s, 2H), 4.04 (s, 6H), 3.95 (s, 6H), 3.60 (s, 6H), 3.41 (m, 4H), 3.02 (m, 4H), 2.18 (s, 6H).

Example 12

Synthesis of 3,3'-dimethyl-5,5'-diphenethyl-2,2'-binaphthyl-1,1',6,6',7,7'-hexanol (12e)

0.27 ml of $BBr_3$ solution (0.72 g, 2.88 mmol) was added dropwise into a solution of 11e (200 mg, 0.30 mmol) in 8 ml of anhydrous $CH_2Cl_2$ at −78° C. Stirring was continued at −78° C. for 1 hour, 0° C. for 1 hour, and ambient temperature for 1 hour, respectively. 100 grams of ice containing 10 ml of 6M HCl was added to the mixture and stirred for one hour at room temperature. The aqueous layer was extracted with dichloromethane (3×50 ml). The combined organic layer was washed with water, brine and dried over $MgSO_4$. The solvent was concentrated in vacuo and the residue was purified by C-18 column chromatography ($H_2O$/Acetonitrile) to give 128 mg of compound 12e (75%) as orange solid. $^1$H NMR ($CDCl_3$) δ 7.52 (s, 2H), 7.44 (s, 2H), 7.30 (m, 10H), 5.35 (s, OH, 4H), 5.17 (s, OH, 2H), 3.37 (t, $J_1$=$J_2$=6.6 Hz, 4H), 3.03 (t, $J_1$=$J_2$=6.6 Hz, 4H), 2.13 (s, 6H).

Example 13

Synthesis of Compounds 11a-11e and 12a-12e

Following herein mentioned procedure and the appropriate starting materials and reagents used; compounds (11a-11e and 12a-12e) were synthesized.

1,1',6,6',7,7'-hexamethoxy-3,3'-dimethyl-$N^5,N^{5'}$-diphenyl-2,2'-binaphthyl-5,5'-dicarboxamide (7a). Yield, 45%. $^1$H NMR (CD$_3$OD) δ 7.76 (d, J=7.8 Hz, 4H), 7.59 (s, 2H), 7.52 (s, 2H), 7.40 (t, $J_1$=$J_2$=7.8 Hz, 4H), 7.18 (s, 2H), 4.04 (s, 6H), 4.00 (s, 6H), 3.63 (s, 6H), 2.11 (s, 6H).

$N^5,N^{5'}$-dicyclopentyl-1,1',6,6',7,7'-hexamethoxy-3,3'-dimethyl-2,2'-binaphthyl-5,5'-dicarboxamide (7b). Yield, 40%. $^1$H NMR (CD$_3$OD) δ 7.52 (s, 2H), 7.45 (s, 2H), 4.47 (m, 2H), 3.98 (s, 6H), 3.96 (s, 6H), 3.60 (s, 6H), 2.11 (m, 10H), 1.79 (s, 4H), 1.68 (s, 8H).

1,1',6,6',7,7'-hexamethoxy-3,3'-dimethyl-$N^5,N^{5'}$-bis(4-phenoxyphenyl)-2,2'-binaphthyl-5,5'-dicarboxamide (7c). Yield, 46%. $^1$H NMR (CD$_3$OD) δ 7.76 (m, 6H), 7.59 (m, 2H), 7.53 (m, 2H), 7.35 (m, 2H), 7.11 (m, 2H), 7.03 (m, 8H), 4.00 (s, 6H), 4.00 (s, 6H), 3.63 (s, 6H), 2.12 (s, 6H).

$N^5,N^{5'}$-bis(3-ethylphenyl)-1,1',6,6',7,7'-hexamethoxy-3,3'-dimethyl-2,2'-binaphthyl-5,5'-dicarboxamide (7d). Yield, 47%. $^1$H NMR (CD$_3$OD) δ 7.62 (s, 2H), 7.58 (m, 4H), 7.52 (s, 2H), 7.30 (m, 2H), 7.05 (m, 2H), 4.04 (s, 6H), 3.99 (s, 6H), 3.63 (s, 6H), 2.54 (q, $J_1$=$J_2$=8.4 Hz, 4H), 2.11 (s, 6H), 1.28 (t, $J_1$=$J_2$=8.4 Hz, 6H).

1,1',6,6',7,7'-hexamethoxy-3,3'-dimethyl-$N^5,N^{5'}$-bis(3-(trifluoromethyl)phenyl)-2,2'-binaphthyl-5,5'-dicarboxamide (7e). Yield, 50%. $^1$H NMR (CD$_3$OD) δ 7.88 (s, 2H), 7.77 (d, J=6.6 Hz, 2H), 7.60 (m, 4H), 7.54 (s, 2H), 7.36 (s, 2H), 4.77 (s, 4H), 3.99 (s, 6H), 3.94 (s, 6H), 3.58 (s, 6H), 2.05 (s, 6H).

1,1',6,6',7,7'-hexamethoxy-3,3'-dimethyl-N5,N5'-bis(1-phenylpropyl)-2,2'-binaphthyl-5,5'-dicarboxamide (7l). Yield, 46%. $^1$H NMR (CD$_3$OD) δ 7.50 (m, 6H), 7.38 (m, 4H), 7.26 (m, 4H), 5.12 (s, 2H), 4.01 (s, 6H), 4.00 (s, 6H), 3.89 (s, 6H), 3.58 (s, 3H), 3.55 (s, 3H), 1.95 (m, 10H), 1.10 (s, 6H).

$N^5,N^{5'}$-dibenzyl-1,1',6,6',7,7'-hexamethoxy-3,3'-dimethyl-2,2'-binaphthyl-5,5'-dicarboxamide (7g). Yield, 46%. $^1$H NMR (CD$_3$OD) δ 7.53 (m, 6H), 7.38 (m, 6H), 7.30 (m, 2H), 4.68 (s, 4H), 4.00 (s, 6H), 3.91 (s, 6H), 3.57 (s, 6H), 2.02 (s, 6H).

1,1',6,6',7,7'-hexamethoxy-3,3'-dimethyl-$N^5,N^{5'}$-bis(3-methylbenzyl)-2,2'-binaphthyl-5,5'-dicarboxamide (7h). Yield, 43%. $^1$H NMR (CD$_3$OD) δ 7.52 (s, 2H), 7.36 (d, J=7.8 Hz, 4H), 7.29 (d, J=7.8 Hz, 2H), 7.26 (t, $J_1$=7.8 Hz, $J_2$=7.2 Hz, 2H), 7.11 (d, J=7.2 Hz, 2H), 4.64 (s, 4H), 4.00 (s, 6H), 3.92 (s, 6H), 3.57 (s, 6H), 2.37 (s, 6H), 2.02 (s, 6H).

$N^5,N^{5'}$-bis(3-chlorobenzyl)-1,1',6,6',7,7'-hexamethoxy-3,3'-dimethyl-2,2'-binaphthyl-5,5'-dicarboxamide (7l). Yield, 46%. $^1$H NMR (CD$_3$OD) δ 7.61 (s, 2H), 7.53 (s, 2H), 7.42 (d, J=6.6 Hz, 2H), 7.36 (m, 4H), 7.31 (d, J=7.2 Hz, 2H), 4.68 (s, 4H), 4.00 (s, 6H), 3.98 (s, 6H), 3.58 (s, 6H), 2.07 (s, 6H).

1,1',6,6',7,7'-hexamethoxy-3,3'-dimethyl-$N^5,N^{5'}$-bis(2,4,6-trimethylbenzyl)-2,2'-binaphthyl-5,5'-dicarboxamide (7j). Yield, 40%. $^1$H NMR (CD$_3$OD) δ 7.48 (s, 2H), 7.41 (s, 2H), 6.96 (s, 2H), 6.88 (s, 2H), 3.92 (s, 6H), 3.87 (s, 6H), 3.55 (s, 6H), 3.39 (s, 6H), 2.46 (s, 6H), 2.27 (s, 6H), 2.05 (s, 6H).

$N^5,N^{5'}$-bis(1-(4-chlorophenyl)ethyl)-1,1',6,6',7,7'-hexamethoxy-3,3'-dimethyl-2,2'-binaphthyl-5,5'-dicarboxamide (7k). Yield, 49%. $^1$H NMR (CD$_3$OD) δ 7.52 (m, 6H), 7.39 (m, 4H), 7.24 (s, 1H), 7.25 (m, 1H), 5.36 (m, 2H), 4.01 (s, 3H), 4.00 (s, 3H), 3.90 (s, 3H), 3.89 (s, 3H), 3.57 (s, 3H), 3.56 (s, 3H), 2.01 (s, 3H), 2.00 (s, 3H), 1.58 (s, 3H), 1.57 (s, 3H).

$N^5,N^{5'}$-bis(cyclopropylmethyl)-1,1',6,6',7,7'-hexamethoxy-3,3'-dimethyl-2,2'-binaphthyl-5,5'-dicarboxamide (7l). Yield, 46%. $^1$H NMR (CD$_3$OD) δ 7.52 (s, 2H), 7.49 (s, 2H), 4.00 (s, 6H), 3.96 (s, 6H), 3.59 (s, 6H), 3.37 (d, J=6.9 Hz, 4H), 2.10 (s, 6H), 1.2 (m, 2H), 0.59 (m, 4H), 0.37 (m, 4H).

$N^5,N^{5'}$-bis(cyclohexylmethyl)-1,1',6,6',7,7'-hexamethoxy-3,3'-dimethyl-2,2'-binaphthyl-5,5'-dicarboxamide (7m). Yield, 50%. $^1$H NMR (CD$_3$OD) δ 7.52 (s, 2H), 7.45 (s, 2H), 4.02 (s, 6H), 3.94 (s, 6H), 3.59 (s, 6H), 3.33 (d, J=17.4 Hz, 4H), 2.09 (s, 6H), 1.94 (d, J=12.0 Hz, 4H), 1.80 (d, J=12.0 Hz, 4H), 1.72 (d, J=10.6 Hz, 4H), 1.39-1.07 (m, 10H).

1,1',6,6',7,7'-hexamethoxy-3,3'-dimethyl-$N^5,N^{5'}$-diphenethyl-2,2'-binaphthyl-5,5'-dicarboxamide (7n). Yield, 51%. $^1$H NMR (CD$_3$OD) δ 7.51 (s, 2H), 7.36 (d, J=7.2 Hz, 4H), 7.30 (m, 6H), 7.22 (t, $J_1$=$J_2$=7.2 Hz, 2H), 4.00 (s, 6H), 3.89 (s, 6H), 3.78 (t, $J_1$=7.2 Hz, $J_2$=6.6 Hz, 4H), 3.57 (s, 6H), 3.02 (t, $J_1$=6.6 Hz, $J_2$=7.2 Hz, 4H), 2.04 (s, 6H).

1,1',6,6',7,7'-hexamethoxy-3,3'-dimethyl-$N^5,N^{5'}$-bis(3-methylphenethyl)-2,2'-binaphthyl-5,5'-dicarboxamide (7o). Yield, 50%. $^1$H NMR (CD$_3$OD) δ 7.51 (s, 2H), 7.28 (s, 2H), 7.23 (m, 4H), 7.12 (m, 4H), 3.97 (s, 6H), 3.89 (s, 6H), 3.75 (s, 6H), 3.58 (m, 4H), 2.97 (m, 4H), 2.29 (s, 6H), 2.02 (s, 6H).

$N^5,N^{5'}$-bis(3-chlorophenethyl)-1,1',6,6',7,7'-hexamethoxy-3,3'-dimethyl-2,2'-binaphthyl-5,5'-dicarboxamide (7p). Yield, 45%. $^1$H NMR (CD$_3$OD) δ 7.51 (s, 2H), 7.39 (s, 2H), 7.30 (d, J=4.2 Hz, 4H), 7.25 (m, 4H), 4.03 (s, 6H), 3.95 (s, 6H), 3.78 (m, 4H), 3.55 (s, 6H), 3.02 (t, $J_1$=$J_2$=6.6 Hz, 4H), 2.04 (s, 6H).

$N^5,N^{5'}$-bis(4-ethylphenethyl)-1,1',6,6',7,7'-hexamethoxy-3,3'-dimethyl-2,2'-binaphthyl-5,5'-dicarboxamide (7q). Yield, 47%. $^1$H NMR (CD$_3$OD) δ 7.52 (s, 2H), 7.27 (s, 2H), 7.23 (d, J=7.8 Hz, 4H), 7.15 (d, J=7.8 Hz, 4H), 4.02 (s, 6H), 3.92 (s, 6H), 3.91 (m, 4H), 3.49 (s, 6H), 3.01 (t, $J_1$=$J_2$=6.6 Hz, 4H), 2.61 (q, $J_1$=$J_2$=7.8 Hz, 6H), 2.11 (s, 6H), 1.21 (t, $J_1$=$J_2$=7.8 Hz, 6H).

$N^5,N^{5'}$-bis(2,3-dihydro-1H-inden-2-yl)-1,1',6,6',7,7'-hexamethoxy-3,3'-dimethyl-2,2'-binaphthyl-5,5'-dicarboxamide (7s). Yield, 47%. $^1$H NMR (CD$_3$OD) δ 7.50 (s, 2H), 7.45 (s, 2H), 7.26 (m, 4H), 7.15 (m, 4H), 4.94 (m, 2H), 3.99 (s, 6H), 3.90 (s, 6H), 3.56 (s, 6H), 3.43 (m, 4H), 3.07 (m, 4H), 2.08 (s, 6H).

1,1',6,6',7,7'-hexahydroxy-3,3'-dimethyl-$N^5,N^{5'}$-diphenyl-2,2'-binaphthyl-5,5'-dicarboxamide (8a). Yield, 75%. $^1$H NMR (CD$_3$OD) δ 7.77 (d, J=7.8 Hz, 4H), 7.63 (s, 2H), 7.38 (t, $J_1$=7.8 Hz, $J_2$=7.2 Hz, 4H), 7.28 (s, 2H), 7.16 (t, $J_1$=7.8 Hz, $J_2$=7.2 Hz, 2H), 2.01 (s, 6H).

$N^5,N^{5'}$-dicyclopentyl-1,1',6,6',7,7'-hexahydroxy-3,3'-dimethyl-2,2'-binaphthyl-5,5'-dicarboxamide (8b). Yield, 76%. $^1$H NMR (CD$_3$OD) δ 7.57 (s, 2H), 7.19 (s, 2H), 4.46 (m, 2H), 2.09 (m, 4H), 1.97 (s, 6H), 1.80 (m, 4H), 1.69 (m, 8H).

1,1',6,6',7,7'-hexahydroxy-3,3'-dimethyl-$N^5,N^{5'}$-bis(4-phenoxyphenyl)-2,2'-binaphthyl-5,5'-dicarboxamide (8c). Yield, 65%. $^1$H NMR (CD$_3$OD) δ 7.78 (d, J=8.4 Hz, 4H), 7.64 (s, 2H), 7.35 (t, $J_1$=7.8 Hz, $J_2$=7.8 Hz, 4H), 7.28 (s, 2H), 7.08 (m, 2H), 7.02 (m, 8H), 2.01 (s, 6H).

$N^5,N^{5'}$-bis(3-ethylphenyl)-1,1',6,6',7,7'-hexahydroxy-3,3'-dimethyl-2,2'-binaphthyl-5,5'-dicarboxamide (8d). Yield, 69%. $^1$H NMR (CD$_3$OD) δ 7.63 (s, 4H), 7.60 (d, J=7.8 Hz, 2H), 7.28 (m, 4H), 7.02 (d, J=7.8 Hz, 2H), 2.68 (q, $J_1$=$J_2$=8.4 Hz, 4H), 2.01 (s, 6H), 1.28 (t, $J_1$=$J_2$=8.4 Hz, 6H).

1,1',6,6',7,7'-hexahydroxy-3,3'-dimethyl-$N^5,N^{5'}$-bis(3-(trifluoromethyl)phenyl)-2,2'-binaphthyl-5,5'-dicarboxamide (8e). Yield, 69%. $^1$H NMR (CD$_3$OD) δ 8.26 (s, 2H), 7.96 (d, J=7.8 Hz, 2H), 7.65 (s, 2H), 7.57 (t, $J_1$=$J_2$=6.6 Hz, 2H), 7.44 (d, J=7.2 Hz, 2H), 7.27 (s, 2H), 2.01 (s, 6H).

1,1',6,6',7,7'-hexahydroxy-3,3'-dimethyl-$N^5,N^{5'}$-bis(1-phenylpropyl)-2,2'-binaphthyl-5,5'-dicarboxamide (8l).

Yield, 70%. $^1$H NMR (CD$_3$OD) δ 7.50 (m, 4H), 7.31 (m, 6H), 7.09 (s, 2H), 6.95 (s, 2H), 5.09 (m, 2H), 1.88 (m, 6H), 1.09 (m, 6H).

N$^5$,N$^{5'}$-dibenzyl-1,1',6,6',7,7'-hexahydroxy-3,3'-dimethyl-2,2'-binaphthyl-5,5'-dicarboxamide (8g). Yield, 78%. $^1$H NMR (CD$_3$OD) δ 7.58 (s, 2H), 7.54 (d, J=7.2 Hz, 4H), 7.36 (t, J$_1$=J$_2$=7.2 Hz, 4H), 7.27 (t, J$_1$=J$_2$=7.2 Hz, 2H), 7.16 (s, 2H), 4.70 (s, 4H), 1.91 (s, 6H).

1,1',6,6',7,7'-hexahydroxy-3,3'-dimethyl-N$^5$,N$^{5'}$-bis(3-methylbenzyl)-2,2'-binaphthyl-5,5'-dicarboxamide (8h). Yield, 75%. $^1$H NMR (CD$_3$OD) δ 7.58 (s, 1H), 7.36 (s, 2H), 7.30 (d, J=7.8 Hz, 2H), 7.23 (t, J$_1$=7.8 Hz, J$_2$=7.2 Hz, 2H), 7.16 (s, 2H), 7.08 (d, J=7.2 Hz, 2H), 4.65 (t, J$_1$=J$_2$=15.0 Hz, 4H), 2.36 (s, 6H), 1.91 (s, 6H).

N$^5$,N$^{5'}$-bis(3-chlorobenzyl)-1,1',6,6',7,7'-hexahydroxy-3,3'-dimethyl-2,2'-binaphthyl-5,5'-dicarboxamide (8I). Yield, 70%. $^1$H NMR (CD$_3$OD) δ 7.59 (d, J=4.2 Hz, 4H), 7.46 (d, J=7.2 Hz, 2H), 7.35 (t, J$_1$=J$_2$=7.2 Hz, 2H), 7.28 (d, J=7.2 Hz, 2H), 7.15 (s, 2H), 4.68 (s, 4H), 1.93 (s, 6H).

1,1',6,6',7,7'-hexahydroxy-3,3'-dimethyl-N$^5$,N$^{5'}$-bis(2,4,6-trimethylbenzyl)-2,2'-binaphthyl-5,5'-dicarboxamide (8j). Yield, 70%. $^1$H NMR (CD$_3$OD) δ 7.54 (s, 2H), 7.18 (s, 2H), 6.87 (s, 4H), 4.70 (s, 4H), 2.46 (s, 12H), 2.22 (s, 6H), 1.91 (s, 6H).

N$^5$,N$^{5'}$-bis(1-(4-chlorophenyl)ethyl)-1,1',6,6',7,7'-hexahydroxy-3,3'-dimethyl-2,2'-binaphthyl-5,5'-dicarboxamide (8k). Yield, 73%. $^1$H NMR (CD$_3$OD) δ 7.53 (m, 6H), 7.35 (m, 4H), 7.09 (s, 2H), 6.95 (s, 2H), 5.33 (m, 2H), 1.91 (s, 3H), 1.86 (s, 3H), 1.56 (m, 3H), 1.54 (m, 3H).

N$^5$,N$^{5'}$-bis(cyclopropylmethyl)-1,1',6,6',7,7'-hexahydroxy-3,3'-dimethyl-2,2'-binaphthyl-5,5'-dicarboxamide (8I). Yield, 70%. $^1$H NMR (CD$_3$OD) δ 7.58 (s, 2H), 7.26 (s, 2H), 3.36 (m, 4H), 1.97 (s, 6H), 1.18 (m, 2H), 0.57 (d, J=8.1 Hz, 4H), 0.37 (m, 4H).

N$^5$,N$^{5'}$-bis(cyclohexylmethyl)-1,1',6,6',7,7'-hexahydroxy-3,3'-dimethyl-2,2'-binaphthyl-5,5'-dicarboxamide (8m). Yield, 80%. $^1$H NMR (CD$_3$OD) δ 7.58 (s, 2H), 7.22 (s, 2H), 3.32 (m, 4H), 1.96 (s, 6H), 1.79 (d, J=7.2 Hz, 4H), 1.71 (d, J=8.4 Hz, 4H), 1.39-1.08 (m, 14H).

1,1',6,6',7,7'-hexahydroxy-3,3'-dimethyl-N$^5$,N$^{5'}$-diphenethyl-2,2'-binaphthyl-5,5'-dicarboxamide (8n). Yield, 80%. $^1$H NMR (CD$_3$OD) δ 7.58 (s, 2H), 7.36 (d, J=7.2 Hz, 4H), 7.31 (t, J$_1$=J$_2$=7.2 Hz, 4H), 7.21 (t, J$_1$=J$_2$=7.2 Hz, 2H), 7.09 (s, 2H), 3.74 (m, 4H), 3.01 (t, J$_1$=J$_2$=7.2 Hz, 4H), 1.92 (s, 6H).

1,1',6,6',7,7'-hexahydroxy-3,3'-dimethyl-N$^5$,N$^{5'}$-bis(3-methylphenethyl)-2,2'-binaphthyl-5,5'-dicarboxamide (8o). Yield, 76%. $^1$H NMR (CD$_3$OD) δ 7.57 (s, 2H), 7.23 (d, J=7.8 Hz, 4H), 7.11 (d, J=7.8 Hz, 4H), 7.06 (s, 2H), 3.80 (m, 4H), 2.96 (t, J$_1$=J$_2$=7.2 Hz, 4H), 2.29 (s, 6H), 1.90 (s, 6H), 1.40 (s, 4H).

N$^5$,N$^{5'}$-bis(3-chlorophenethyl)-1,1',6,6',7,7'-hexahydroxy-3,3'-dimethyl-2,2'-binaphthyl-5,5'-dicarboxamide (8p). Yield, 70%. $^1$H NMR (CD$_3$OD) δ 7.57 (s, 2H), 7.39 (s, 2H), 7.30 (t, J$_1$=7.2 Hz, J$_2$=6.6 Hz, 4H), 7.21 (d, J=6.6 Hz, 2H), 7.03 (s, 2H), 3.79 (m, 2H), 3.70 (m, 2H), 3.00 (m, 4H), 1.91 (s, 6H).

N$^5$,N$^{5'}$-bis(4-ethylphenethyl)-1,1',6,6',7,7'-hexahydroxy-3,3'-dimethyl-2,2'-binaphthyl-5,5'-dicarboxamide (8q). Yield, 75%. $^1$H NMR (CD$_3$OD) δ 7.58 (s, 2H), 7.26 (d, J=7.8 Hz, 4H), 7.15 (d, J=7.8 Hz, 4H), 7.10 (s, 2H), 3.75 (m, 2H), 3.70 (m, 2H), 2.98 (t, J$_r$=J$_2$=7.2 Hz, 4H), 2.60 (q, J$_1$=7.8 Hz, J$_2$=7.2 Hz, 4H), 1.91 (s, 6H), 1.20 (t, J$_1$=7.8 Hz, J$_2$=7.2 Hz, 6H).

N$^5$,N$^{5'}$-bis(2,3-dihydro-1H-inden-2-yl)-1,1',6,6',7,7'-hexahydroxy-3,3'-dimethyl-2,2'-binaphthyl-5,5'-dicarboxamide (8s). Yield, 72%. $^1$H NMR (CD$_3$OD) δ 7.57 (s, 2H), 7.24 (s, 4H), 7.19 (s, 2H), 7.14 (s, 4H), 4.94 (m, 2H), 3.42 (m, 4H), 3.07 (m, 4H), 1.94 (s, 6H).

N$^5$,N$^{5'}$-bis(4-chlorophenethyl)-1,1',6,6',7,7'-hexahydroxy-3,3'-dimethyl-2,2'-binaphthyl-5,5'-dicarboxamide (8t). Yield, 75%. $^1$H NMR (CD$_3$OD) δ 7.57 (s, 2H), 7.35 (d, J=7.8 Hz, 4H), 7.30 (d, J=7.8 Hz, 4H), 7.02 (s, 2H), 3.76 (m, 2H), 3.71 (m, 2H), 2.99 (t, J$_r$=J$_2$=6.6 Hz, 4H), 1.93 (s, 6H).

5,5'-diisobutyl-1,1',6,6',7,7'-hexamethoxy-3,3'-dimethyl-2,2'-binaphthyl (11a). Yield, 85%. $^1$H NMR (CDCl$_3$) δ 7.60 (s, 2H), 7.41 (s, 2H), 3.99 (s, 6H), 3.90 (s, 6H), 3.57 (s, 6H), 2.97 (d, J=7.2 Hz, 4H), 2.19 (s, 6H), 2.12 (m, 2H), 1.03 (t, J$_1$=J$_2$=6.0 Hz, 12H).

5,5'-diisopentyl-1,1',6,6',7,7'-hexamethoxy-3,3'-dimethyl-2,2'-binaphthyl (11b). Yield, 81%. $^1$H NMR (CDCl$_3$) δ 7.63 (s, 2H), 7.38 (s, 2H), 3.99 (s, 6H), 3.96 (s, 6H), 3.59 (s, 6H), 3.08 (m, 4H), 2.2 (s, 6H), 1.80 (m, 2H), 1.29 (m, 4H), 1.06 (m, 12H).

5,5'-bis(cyclopentylmethyl)-1,1',6,6',7,7'-hexamethoxy-3,3'-dimethyl-2,2'-binaphthyl (11c). Yield, 80%. $^1$H NMR (CDCl$_3$) δ 7.65 (s, 2H), 7.40 (s, 2H), 3.99 (s, 6H), 3.90 (s, 6H), 3.58 (s, 6H), 3.09 (d, J=7.2 Hz, 4H), 2.38 (m, 2H), 2.20 (s, 6H), 1.73 (m, 8H), 1.54 (m, 8H).

1,1',6,6',7,7'-hexamethoxy-3,3'-dimethyl-2,2'-binaphthyl (11e). Yield, 90%. $^1$H NMR (CDCl$_3$) δ 7.46 (s, 2H), 7.45 (s, 2H), 7.14 (s, 2H), 4.04 (s, 6H), 4.02 (s, 6H), 3.57 (s, 6H), 2.18 (s, 6H).

5,5'-diisobutyl-3,3'-dimethyl-2,2'-binaphthyl-1,1',6,6',7,7'-hexanol (12a). Yield, 80%. $^1$H NMR (CD$_3$OD) δ 7.44 (s, 2H), 7.34 (s, 2H), 2.95 (d, J=7.2 Hz, 4H), 2.14 (m, 2H), 2.05 (s, 6H), 1.02 (d, J=6.0 Hz, 6H), 1.00 (d, J=6.0 Hz, 6H).

5,5'-diisopentyl-3,3'-dimethyl-2,2'-binaphthyl-1,1',6,6',7,7'-hexanol (12b). Yield, 79%. $^1$H NMR (CD$_3$OD) δ 7.42 (s, 2H), 7.34 (s, 2H), 3.04 (t, J$_1$=J$_2$=5.4 Hz, 4H), 2.05 (s, 6H), 1.74 (m, 2H), 1.55 (m, 4H), 1.05 (d, J=3.6 Hz, 6H), 1.04 (d, J=3.6 Hz, 6H).

5,5'-bis(cyclopentylmethyl)-3,3'-dimethyl-2,2'-binaphthyl-1,1',6,6',7,7'-hexanol (12c). Yield, 78%. $^1$H NMR (CD$_3$OD) δ 7.41 (s, 2H), 7.37 (s, 2H), 3.06 (d, J=7.2 Hz, 4H), 2.36 (m, 2H), 2.03 (s, 6H), 1.72 (m, 8H), 1.50 (m, 8H).

5,5'-dibenzyl-3,3'-dimethyl-2,2'-binaphthyl-1,1',6,6',7,7'-hexanol (12d). Yield, 72%. $^1$H NMR ((CD$_3$)$_2$SO) δ 9.81 (s, 2H), 8.64 (s, 2H), 7.76 (s, 2H), 7.39 (s, 2H), 7.24 (m, 10H), 7.10 (m, 2H), 4.28 (dd, J$_1$=15.0 Hz, J$_2$=19.8 Hz, 4H), 1.94 (s, 6H). E1 $^{13}$C NMR ( ) δ 150.69, 145.86, 145.66, 143.20, 134.04, 126.97, 120.46, 119.85, 117.38, 116.13, 105.10, 101.09, 32.0, 22.5.

3,3'-dimethyl-5,5'-diphenethyl-2,2'-binaphthyl-1,1',6,6',7,7'-hexanol (12e). Yield, 73%. $^1$H NMR (CDCl$_3$) δ 7.52 (s, 2H), 7.44 (s, 2H), 7.32 (d, J=6.6 Hz, 4H), 7.29 (d, J=7.2 Hz, 4H), 7.18 (t, J$_1$=7.2 Hz, J$_1$=6.6 Hz, 2H), 5.35 (s, 4H), 5.17 (s, 2H), 3.37 (t, J$_1$=J$_2$=6.6 Hz, 4H), 3.03 (t, J$_1$=J$_2$=6.6 Hz, 4H), 2.13 (s, 6H).

3,3'-dimethyl-2,2'-binaphthyl-1,1',6,6',7,7'-hexanol (13). Yield, 75%. $^1$H NMR (CD$_3$OD) δ 7.46 (s, 2H), 7.11 (s, 2H), 7.02 (s, 2H), 1.97 (s, 6H).

1,1',6,6',7,7'-hexahydroxy-3,3'-dimethyl-2,2'-binaphthyl-5,5'-dicarboxylic acid (14). Yield, 70%. $^1$H NMR (CD$_3$OD) δ 8.29 (s, 2H), 7.83 (s, 2H), 2.04 (s, 6H).

TABLE 8

HIGH RESOLUTION MASS (HRMS) AND HPLC PURITY
OF 5,5'-SUBSTITUTED APOGOSSYPOL DERIVATIVES

| Compd. | Chemical Formula | HRMS [M + H]+ Calculated | Found | HPLC Purity (%) |
|---|---|---|---|---|
| 2 (Apogossypol) | $C_{28}H_{30}O_6$ | 463.2115 | 463.2108 | 99.5 |
| 8a | $C_{36}H_{28}N_2O_8$ | 617.1918 | 617.1912 | 99.0 |
| 8b | $C_{34}H_{36}N_2O_8$ | 601.2544 | 601.2531 | 98.7 |
| 8g | $C_{38}H_{32}N_2O_8$ | 645.2231 | 645.2237 | 98.5 |
| 8c | $C_{48}H_{36}N_2O_{10}$ | 801.2443 | 801.2425 | 99.0 |
| 8n | $C_{40}H_{36}N_2O_8$ | 673.2544 | 673.2536 | 99.4 |
| 8d | $C_{40}H_{36}N_2O_8$ | 673.2544 | 673.2537 | 99.5 |
| 8e | $C_{38}H_{26}F_6N_2O_8$ | 753.1666 | 751.1506 | 98.5 |
| 8h | $C_{40}H_{36}N_2O_8$ | 673.2544 | 673.2536 | 97.5 |
| 8i | $C_{38}H_{30}N_2O_8$ | 713.1452 | 713.1426 | 98.9 |
| 8j | $C_{44}H_{44}N_2O_8$ | 729.3170 | 729.3167 | 99.5 |
| 8l | $C_{32}H_{32}N_2O_8$ | 573.2231 | 573.2214 | 99.2 |
| 8k | $C_{40}H_{34}N_2O_8$ | 741.1765 | 741.1763 | 99.5 |
| 8m | $C_{38}H_{44}N_2O_8$ | 657.3170 | 657.3169 | 99.8 |
| 8p | $C_{40}H_{34}N_2O_8$ | 741.1765 | 741.1769 | 99.5 |
| 8q | $C_{44}H_{44}N_2O_8$ | 729.3170 | 729.3175 | 99.7 |
| 8r | $C_{42}H_{40}N_2O_8$ | 701.2857 | 701.2864 | 99.5 |
| 8s | $C_{42}H_{36}N_2O_8$ | 697.2544 | 697.2541 | 99.0 |
| 8t | $C_{40}H_{34}N_2O_8$ | 741.1765 | 741.1765 | 98.0 |
| 8f | $C_{40}H_{40}N_2O_8$ | 701.2857 | 701.2867 | 99.0 |
| 8o | $C_{40}H_{40}N_2O_8$ | 701.2857 | 701.2859 | 99.0 |
| 12a | $C_{30}H_{34}O_6$ | 491.2428 | 491.2429 | 99.1 |
| 12b | $C_{32}H_{38}O_6$ | 519.2741 | 519.2739 | 99.5 |
| 12c | $C_{34}H_{38}O_6$ | 543.2741 | 543.2739 | 99.3 |
| 12d | $C_{36}H_{30}O_6$ | 559.2115 | 559.2112 | 99.5 |
| 12e | $C_{38}H_{34}O_6$ | 587.2428 | 587.2425 | 99.0 |
| 13 | $C_{22}H_{18}O_6$ | 379.1176 | 379.1168 | 98.5 |
| 14 | $C_{24}H_{18}O_{10}$ | 467.0973 | 467.0964 | 99.4 |

Example 6

NMR Experiments

NMR-based binding assays have been conducted by acquiring one-dimensional $^1H$ experiments with 500 µL solution of BCL-$X_L$ at 25 µM concentration, in absence and presence of added compounds, each at 200 µM concentration. By observing the aliphatic region of the spectra, binding could be readily detected due to chemical shift changes in active site methyl groups of Ile, Leu, Thr, Val or Ala (region between −0.8 and 0.3 ppm). All experiments were performed with a 600 MHz spectrometer Bruker Avance 600 equipped with four rf channels and z-axis pulse-field gradients.

Example 7

Fluorescence Polarization Assays (FPA)

A Bak BH3 peptide (F-BakBH3) (GQVGRQLAIIGD-DINR) was labeled at the N-terminus with fluorescein isothiocyanate (FITC) (Molecular Probes) and purified by HPLC. For competitive binding assays, 100 nM GST-BCL-$X_L$ ΔTM protein was preincubated with the tested compound at varying concentrations in 47.5 µL PBS (pH=7.4) in 96-well black plates at room temperature for 10 min, then 2.5 µL of 100 nM FITC-labeled Bak BH3 peptide was added to produce a final volume of 50 µL. The wild-type and mutant Bak BH3 peptides were included in each assay plate as positive and negative controls, respectively. After 30 min incubation at room temperature, the polarization values in millipolarization units were measured at excitation/emission wavelengths of 480/535 nm with a multilabel plate reader (PerkinElmer). $IC_{50}$ was determined by fitting the experimental data to a sigmoidal dose-response nonlinear regression model (Sigma-Plot 10.0.1, Systat Software, Inc., San Jose, Calif., USA). Data reported are mean of three independent experiments±standard error (SE). Performance of BCL-2 and Mcl-1 FPA are similar. Briefly, 50 nM of GST-BCL-2 or -Mcl-1 were incubated with various concentrations of Apogossypol, or its 5,5' substituted derivatives for 2 min, then 15 nM FITC-conjugated-Bim BH3 peptide was added in PBS buffer. Fluorescence polarization was measured after 10 min.

Example 8

Isothermal Titration Calorimetry Assays (ITC)

Titrations were performed using a VP-ITC or ITC200 calorimeter from Microcal (Northampton, Mass.). BCL-$X_L$ was used at concentrations between 25 and 100 µM in 20 mM sodium phosphate buffer (pH 7.4) and 5-10% DMSO. Titrants were used at concentrations 10-15 fold of that of the protein in the same buffer. Titrations were carried out at 25° C. Data were analyzed using Microcal Origin software provided by the ITC manufacturer (Microcal, Northampton, Mass.).

Example 9

Cell Viability and Apoptosis Assays

The activity of the compounds against human cancer cell lines (PC3ML, H460, H1299, RS11846) were assessed by using the ATP-LITE assay (PerkinElmer). All cells were seeded in either F12 or RPMI1640 medium with 5 mM L-glutamine supplemented with 5% fetal bovine serum (Mediatech Inc.), penicillin and streptomycin (Omega). For maintenance, cells were cultured in 5% FBS. Cells plated into 96 well plates at varying initial densities depending on doubling time. H460 and H1299 plated at 2000 cells/well, A549 and PC3 at 3000 cells/well, and RS118456S at 10,000 cells/well. Compounds were diluted to final concentrations with 0.1% DMSO. Prior to dispensing compounds onto cells, fresh 5% media was placed into wells. Administration of compounds occurred 24 hours after seeding into the fresh media. Cell viability was evaluated using ATP-LITE reagent (PerkinElmer) after 72 hours of treatment. Data were normalized to the DMSO control-treated cells using Prism version 5.01 (Graphpad Software).

The apoptotic activity of the compounds against RS11846 cells was assessed by staining with Annexin V- and propidium iodide (PI). Lymphoma cell line, RS11846, was cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of 5,5' substituted Apogossypol for 1-2 days. The percentage of viable cells was determined by FITC-Annexin V- and propidium iodide (PI)-labeling, using an Apoptosis Detection kit (BioVision Inc.), and analyzing stained cells by flow cytometry (FACSort; Bectin-Dickinson, Inc.; Mountain View, Calif.). Cells that were annexin-V-negative and PI-negative were considered viable.

The apoptotic activity of the compounds, such as 8r, 8q against mouse embryonic fibroblast wild-type cells (MEF/WT) and mouse embryonic fibroblast BAX/Bak double knockout cells (MEF/DKO) was assessed by staining with Annexin V- and propidium iodide (PI). MEF/WT and MEF/DKO cells were seeded in 24-well plate at a seeding density of half a million per well (in 1 ml of DMEM medium supplemented by 10% FCS). Next day, compound was added to wild-type and DKO cells at final concentration of 0, 2.5, 5.0, 7.5 and 100 µM. On the following day, floating cells were pooled with adherent cells harvested after brief incubation with 0.25% Trypsin/EDTA solution (Gibco/In-Vitrogen Inc.). Cells were centrifuged and supernatant was discarded, and cell pellet was re-suspended with 0.2 ml of Annexin-V binding buffer, followed by addition of 1 µl Annexin-FITC and 1 µl PI (propidium iodide). The percentage of viable cells was determined by a 3-color FACSort instrument and data analyzed by Flow-Jo program, scoring Annexin V-negative, PI-negative as viable cells.

Example 10

In Vitro ADMET Studies

Liver Microsomal Stability. Pooled rat liver microsomes (BD Biosciences, #452701) were preincubated with test compounds at 37.5° C. for 5 min in the absence of NADPH. The reaction was initiated by addition of NADPH and then incubated under the same conditions. The final incubation concentrations were 4 µM test compound, 2 mM NADPH, and 1 mg/mL (total protein) liver microsomes in phosphate-buffered saline (PBS) at pH 7.4. One aliquot (100 µL) of the incubation mixture was withdrawn at 0, 15, 30, and 60 min and combined immediately with 200 µL of ACN/MeOH containing an internal standard. After mixing, the sample was centrifuged at approximately 13,000 rpm for 12 min. The supernatant was transferred into an autosampler vial and the amount of test compound was quantified using the Shimadzu LCMS 2010EV mass spectrometer. The change of the AUC (area under the curve) of the parent compound as function of time was used as a measure of microsomal stability.

Plasma Stability. A 20 µL aliquot of a 10 mM solution in DMSO of the test compound was added to 2.0 mL of heparinized rat plasma (Lampire, P1-150N) to obtain a 100 µM final solution. The mixture was incubated for 1 h at 37.5° C. Aliquots of 100 µL were taken (0, 30 min, 1 h) and diluted with 200 µL of MeOH containing internal standard. After mixing, the sample was centrifuged at approximately 13,000 rpm for 12 min. The supernatant was transferred into an autosampler vial and the amount of test compound was quantified using the Shimadzu LCMS-2010EV system. The change of the AUC (area under the curve) of the parent compound as function of time was used as a measure of microsomal stability.

Example 11

PAMPA Assays

PAMPA is parallel artificial membrane permeation assay. A 96-well microtiter plate (Millipore, #MSSACCEPTOR) was completely filled with aqueous buffer solution (pH 7.2) and covered with a microtiter filterplate (Millipore, #MAPBMN310). The hydrophobic filter material was impregnated with a 10% solution of hexadecane in hexane and the organic solvent was allowed to completely evaporate. Permeation studies were started by the transfer of 200 µL of a 100 µM test compound solution on top of the filterplate. In general phosphate buffer at pH 7.2 buffer was used. The maximum DMSO content of the stock solutions was <5%. In parallel, an equilibrium solution lacking a membrane was prepared using the exact concentrations and specifications but lacking the membrane. The concentrations of the acceptor and equilibrium solutions were determined using the Shimadzu LCMS-2010EV and AUC methods. The permeation of a compound through the membrane layer is described by the percentage permeation (% flux). The flux values were calculated considering the concentration of the acceptor compartment after 8 h and that of a reference well with the same concentration containing no membrane barrier.

Example 12

Transgenic Mice Studies

Transgenic mice expressing BCL-2 have been described as the B6 line. The BCL-2 transgene res a minigene version of a t(14;18) translocation in which the human BCL-2 gene is fused with the immunoglobulin heavy-chain (IgH) locus and associated IgH enhancer. The transgene was propagated on the Balb/c background. These mice develop polyclonal B-cell hyperplasia with asynchronous transformation to monoclonal aggressive lymphomas beginning at approximately 6 months of age, with approximately 90% of mice undergoing transformation by the age of 12 to 24 months. All animals used here had not yet developed aggressive lymphoma.

Example 13

Further Mouse Experiments

Compounds dissolved in 500 µL of solution (Ethanol:Cremophor EL:Saline=10:10:80) were injected intraperitoneally to age- and sex-matched B6BCL2 mouse, while control-mice were injected intraperitoneally with 500 µL of the same formulation without compound. After 24 hours, B6BCL2 mice were sacrificed by intraperitoneal injection of lethal dose of Avertin. Spleen was removed and weighed. The spleen weight of mice is used as an end-point for assessing activity as we determined that spleen weight is highly consistent in age- and sex-matched BCL-2-transgenic mice in preliminary studies. Variability of spleen weight was within ±2% among control-treated age-matched, sex-matched B6BCL2 mice. Spleen tissue was fixed in z-FIX for 3 days and rinsed in PBS, and saved for histological analysis of spleen (H&E staining and TUNEL assay).

Example 14

Comparisons with Apogossypol

Molecular docking studies of apogossypol into the BH3 binding groove in BCL-$X_L$ suggest that apogossypol forms two hydrogen bonds with residues Arg 139 and Tyr 195 in BCL-$X_L$ through adjacent sixth and seventh hydroxyl groups on the right naphthalene ring. The isopropyl group on the left naphthalene ring inserts into the first hydrophobic pocket (P1) in BCL-$X_L$, while the methyl group and the isopropyl group on the right naphthalene ring insert into the adjacent two hydrophobic pockets, P2 and P3, respectively. Analysis of the predicted binding models indicates that while the overall core structure of apogossypol fits rather well into BH3 binding groove of BCL-$X_L$, the two isopropyl groups do not apparently fully occupy the hydrophobic pockets P1 and P3.

Therefore, a library of 5,5' substituted apogossypol derivatives that replace the isopropyl groups with larger hydrophobic substituents was designed with the aim of deriving novel molecules that could occupy the hydrophobic pockets on BCL-$X_L$ more efficiently.

The designed 5,5' substituted apogossypol derivatives were synthesized as described herein and evaluated by nuclear magnetic resonance spectroscopy (NMR) binding assays, competitive fluorescence polarization assays (FPA), and cell viability assays as shown in Table 9.

TABLE 9

EVALUATION OF 5,5' SUBSTITUTED APOGOSSYPOL DERIVATIVES USING A COMBINATION OF 1D 1H NMR BINDING ASSAYS, COMPETITIVE FLUORESCENCE POLARIZATION ASSAYS AND CELL VIABILITY ASSAYS

| Compound | R | 1D $^1$H-NMR Binding Assay[a] (BCL-$X_L$) | FPA IC$_{50}$ (μm) (BCL-$X_L$) | PC3ML EC$_{50}$ (μM) | H460 EC$_{50}$ (μM) | H1299 EC$_{50}$ (μM) | RS11846[b] EC$_{50}$ (μM) | RS11846[c] EC$_{50}$ (μM) |
|---|---|---|---|---|---|---|---|---|
| Gossypol | isobutyl | ++ | 2.72 | 3.1 | 3.0 | 6.0 | 2.2 | 4.23 |
| Apogossypol | isobutyl | ++ | 3.69 | 10.3 | 2.8 | 3.4 | 5.0 | 8.6 |
| I | phenylacetyl | +++ | 0.19 | 4.6 | 0.68 | 3.5 | 2.6 | 4.9 |
| II | —H | + | NR | 12.6 | 10.1 | 13.4 | 10.0 | 24.7 |
| III | isobutyryl | ++ | NR | 3.9 | 1.5 | 4.8 | 15 | 14.7 |
| IV | isovaleryl | + | 1.30 | 7.5 | 1.1 | 3.6 | 10 | 13.7 |
| V | 2-hexyl-butanoyl | + | 1.29 | 3.0 | 1.5 | 3.0 | 2.8 | 6.6 |
| VI | cyclopentanoyl | + | 0.45 | 3.4 | 1.1 | 3.1 | 4.0 | 4.5 |
| VII | benzoyl | + | 2.9 | 3.6 | 0.31 | 4.2 | NR | 18.3 |

TABLE 9-continued

EVALUATION OF 5,5' SUBSTITUTED APOGOSSYPOL DERIVATIVES USING A COMBINATION OF 1D 1H NMR BINDING ASSAYS, COMPETITIVE FLUORESCENCE POLARIZATION ASSAYS AND CELL VIABILITY ASSAYS

| Compound | R | 1D $^1$H-NMR Binding Assay[a] (BCL-$X_L$) | FPA IC$_{50}$ (μm) (BCL-$X_L$) | PC3ML EC$_{50}$ (μM) | H460 EC$_{50}$ (μM) | H1299 EC$_{50}$ (μM) | RS11846[b] EC$_{50}$ (μM) | RS11846[c] EC$_{50}$ (μM) |
|---|---|---|---|---|---|---|---|---|
| VIII | 1-naphthyl-C(O)-CH$_2$- | + | 0.16 | 3.0 | 0.59 | 2.4 | 1.8 | 4.2 |
| IX | 4-biphenyl-C(O)-CH$_2$- | − | NR | 7.7 | 8.2 | 9.6 | 2.8 | 25.9 |
| X | 4-tBu-phenyl-C(O)-CH$_2$- | − | NR | 2.8 | 3.6 | 4.8 | 2.3 | 13.4 |
| XI | 4-CF$_3$-phenyl-C(O)-CH$_2$- | + | 0.25 | 2.9 | 2.2 | 2.0 | 2.5 | 3.8 |
| XII | 4-CH$_3$-phenyl-CH$_2$-C(O)-CH$_2$- | ++ | 0.32 | 2.5 | 0.82 | 1.7 | 2.2 | 3.0 |
| XIII | 3-Br-phenyl-CH$_2$-C(O)-CH$_2$- | ++ | 1.31 | 3.1 | 2.7 | 2.6 | 8.4 | 5.3 |
| XIV | 4-CF$_3$O-phenyl-CH$_2$-C(O)-CH$_2$- | ++ | 1.30 | 1.9 | 3.3 | 3.9 | 1.8 | 6.2 |

TABLE 9-continued

EVALUATION OF 5,5' SUBSTITUTED APOGOSSYPOL DERIVATIVES USING A COMBINATION OF 1D 1H NMR BINDING ASSAYS, COMPETITIVE FLUORESCENCE POLARIZATION ASSAYS AND CELL VIABILITY ASSAYS

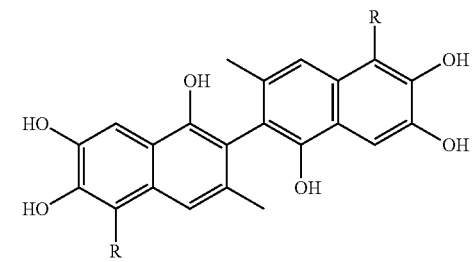

| Compound | R | 1D $^1$H-NMR Binding Assay[a] (BCL-$X_L$) | FPA IC$_{50}$ (μm) (BCL-$X_L$) | PC3ML EC$_{50}$ (μM) | H460 EC$_{50}$ (μM) | H1299 EC$_{50}$ (μM) | RS11846[b] EC$_{50}$ (μM) | RS11846[c] EC$_{50}$ (μM) |
|---|---|---|---|---|---|---|---|---|
| XV | 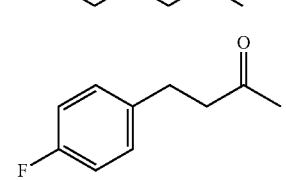 | + | NR | 1.9 | 1.8 | 2.1 | 2 | 5.2 |
| XVI | 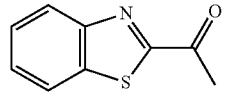 | ++ | 0.14 | 2.8 | 1.5 | 2.2 | 2.3 | 3.1 |
| XVII | 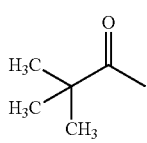 | + | 0.39 | 5.2 | 1.4 | 5.8 | 2.9 | 7 |
| XVIII | 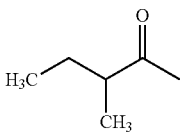 | ++ | NR | NR | NR | NR | NR | 14.7 |
| XIX | 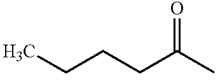 | + | NR | NR | NR | NR | NR | 17.1 |
| XX |  | + | NR | NR | NR | NR | NR | 11.7 |

[a]4-point-rating scale:
+++: Very Active;
++: Active;
+: Mild;
−: Weak
[b]Compounds against RS11846 cell line using ATP-LITE assay
[c]Compounds against RS11846 cell line using Annexin V-and propidium iodide assay Compound I displayed high affinity for BCL-$X_L$ in these assays. It induced significant chemical shift changes in active site methyl groups (region between −0.3 and 0.8 ppm) in the one-dimensional $^1$H-NMR spectra of BCL-$X_L$ and also has an IC$_{50}$ value of 0.19 μM in the FP displacement assays, which is almost 20 times more effective than apogossypol.

A group of compounds, such as compounds XVII, VI, VIII, XI, XVI, and XII also displayed high binding affinity to BCL-$X_L$ in the FP assays with IC$_{50}$ values ranging from 0.14 to 0.45 μM and induced chemical shift changes in the one-dimensional $^1$H-NMR spectra of BCL-$X_L$. To confirm results of the NMR binding data and the FP assays, the binding affinity of compound I and other compounds was further evaluated for BCL-$X_L$ using ITC (Isothermal Titration calorimetry).

TABLE 10

CROSS-ACTIVITY OF SELECTED 5,5' SUBSTITUTED APOGOSSYPOL DERIVATIVES AGAINST BCL-XL, BCL-2, AND MCL-1

| Compound | R | EC$_{50}$ (μM) FPA BCL-X$_L$ | BCL-2 | Mcl-1 | K$_d$ (μM) ITC BCL-X$_L$ |
|---|---|---|---|---|---|
| Apogossypol | isopropyl | 3.69 | 2.80 | 2.60 | 1.70 |
| I | benzyl ketone (—C(O)CH$_2$Ph) | 0.19 | 0.36 | 0.52 | 0.17 |
| XII | 4-methylbenzyl ketone | 0.32 | 0.78 | 1.10 | 0.04 |
| VIII | 1-naphthoyl | 0.16 | 1.90 | 2.20 | 2.75 |

As can be seen, in agreement with NMR binding and FPA data, compound I and its para-methyl substituted derivative compound XII, displayed potent binding affinity to BCL-X$_L$ with K$_d$ values of 0.17 and 0.04 μM, respectively, which is 10 and 40 times more potent than apogossypol (K$_d$=1.7 μM) in the same assay. Molecular docking studies of compound I in the BH3 binding groove of BCL-X$_L$ demonstrated that 5,5' benzyl groups insert deeper into hydrophobic pockets (P1 and P3) in BCL-X$_L$ hence occupying these regions more efficiently compared to isopropyl groups of apogossypol.

Consistent with NMR binding, FPA, and ITC data, compounds such as compounds I and XII display significant efficacy in inhibiting cell growth in PC3ML cells, which express high levels of BCL-X$_L$. Their EC$_{50}$ values ranged from 1.9 to 4.6 μM, hence 2-5 fold more potent than apogossypol (EC$_{50}$=10.3 μM).

To evaluate the binding properties and specificity of 5,5' substituted apogossypol derivatives to other anti-apoptotic BCL-2 family proteins, selected BCL-X$_L$ active compounds were evaluated against BCL-2 and Mcl-1 using FP assays. These BCL-X$_L$ inhibitors also displayed strong binding affinity to BCL-2 and Mcl-1. Compound I binds to BCL-2 and Mcl-1 with EC$_{50}$ values of 0.36 and 0.52 μM, respectively, which are approximately 8 and 5 fold more potent than apogossypol (EC$_{50}$=2.8 04). Compound XII is slightly less active than compound I, while compound VIII has activity that is similar to that of apogossypol.

Since compounds I and XII displayed strong binding affinities to BCL-2 and Mcl-1 in FP assay, all 5,5' substituted apogossypol derivatives were further evaluated against H460 and H1299 cell lines, which express high levels of BCL-2 and Mcl-1, respectively. In agreement with FPA data, compounds I and XII inhibited growth of the H460 cell line with EC$_{50}$ values of 0.68 and 0.82 μM, respectively, which are approximately 4-5 times more potent than apogossypol (EC$_{50}$=3.4 μM). Compounds VII and VIII having structures that are similar to that of compound I also inhibited cell growth in the H460 cell line with EC$_{50}$ values of 0.30 and 0.59 μM, respectively. Most of the tested 5,5' substituted apogossypol derivatives also showed potent cell activity in the H460 and H1299 cell lines with EC$_{50}$ values ranging from 1 to 4 μM.

In contrast, compound II, the negative control compound with hydrogen atoms on 5,5' positions, displayed weak cell growth inhibition activity in both H460 (EC$_{50}$=10.1 μM) and H1299 (EC$_{50}$=13.4 μM) cell lines indicating 5,5' substituted groups are necessary for strong inhibition. This observation is in agreement with reports for the potent BCL-X$_L$ antagonist ABT-737, which is not effective against Mcl-1 and consequentially is not effective in killing Mcl-1 overexpressing cell lines such as the H1299.

5,5' substituted apogossypol derivatives were further tested for their ability to induce apoptosis of the human lymphoma RS11846 cell line, which expresses high levels of BCL-2 and BCL-X$_L$. For these assays, we used Annexin V-FITC and propidium iodide (PI) double staining, followed by flow-cytometry analysis. Most of synthesized apogossypol derivatives effectively induced apoptosis of the RS11846 cell line in a dose-dependent manner. In particular, compounds I, VIII, XI, and XII have EC$_{50}$ values ranging from 3.0 to 5.5 μM, which is consistent with previous results in human cancer PC3ML and H460 cell lines. Again, the negative control compound II induced weak apoptosis (EC$_{50}$=24.7) of the RS11846 cell line, consistent with its poor anti-BCL-2 activity.

To test the pharmacological properties of 5,5' substituted apogossypol derivatives, their in vitro plasma stability, microsomal stability, and cell membrane permeability were determined. The results are shown in Table 11.

TABLE 11

PLASMA STABILITY, MICROSOMAL STABILITY, AND CELL PERMEABILITY OF SELECTED 5,5' SUBSTITUTED APOGOSSYPOL DERIVATIVES

| Compound | R | Plasma Stability (T = 1 hr) | Microsomal Stability (T = 1 hr) | Cell Permeability |
|---|---|---|---|---|
| Apogossypol | isopropyl | 53% | 60% | Low |

TABLE 11-continued

PLASMA STABILITY, MICROSOMAL STABILITY, AND CELL PERMEABILITY OF SELECTED 5,5' SUBSTITUTED APOGOSSYPOL DERIVATIVES

| Compound | R | Plasma Stability (T = 1 hr) | Microsomal Stability (T = 1 hr) | Cell Permeability |
|---|---|---|---|---|
| XVII | benzothiazole-2-yl acetyl | 90% | 68% | Medium |
| VI | cyclopentyl acetyl | 79% | 27% | Low |
| VIII | naphthalen-1-yl acetyl | 62% | 52% | Low |
| I | phenyl acetyl | 85% | 64% | Medium |
| XII | 4-(trifluoromethyl)benzoyl | NR | 41% | Low |
| XII | 4-methylphenyl acetyl | 72% | 92% | Medium |
| XVIII | pivaloyl (tert-butyl ketone) | 90% | 30% | Medium |

As can be seen from the data provided in Table 4, the synthesized compounds of the disclosure displayed superior plasma stability and overall are more stable than apogossypol. Compounds I degraded 15% after 1 hour incubation in rat plasma. In addition, compounds I and XII showed similar or improved microsomal stability compared to Apogossypol, while compounds VI and XVIII, degraded faster than apogossypol in rat hepatocytes microsomal preparations. Compounds I and XII also displayed improved cell membrane permeability compared to apogossypol.

Accordingly, using a combination of 1D $^1$H-NMR binding assays, FP assays, ITC assays, cytotoxicity assays and preliminary in vitro ADME data, compounds such as compounds I and XII were selected for further in vivo studies using B6BCL-2 transgenic mice. B-cells of the B6BCL-2 transgenic mice overexpress BCL-2 and accumulate in the spleen of mice. The spleen weight is used as an end-point for assessing in vivo activity as we determined that the spleen weight is highly consistent in age- and sex-matched BCL-2-transgenic mice and variability was within ±2% among control-treated age-matched, sex-matched B6BCL2 mice. The in vivo activities of compounds such as compounds I and XII were first screened side by side with apogossypol and gossypol in a single BCL-2 transgenic mouse at 60 μmol/kg.

All tested compounds induced significant spleen weight reduction of mice and compound I displayed best efficiency causing 40% reduction in spleen weight. Since the maximum spleen shrinkage would be no more than 50% in this experimental model, the in vivo effect of compound I induced near maximal biological activity at 60 μmol/kg. To confirm the result from a single mouse experiment, the in vivo activity of compound I was next evaluated in groups of six mice each. In agreement with the single mouse experiment, compound I treatment of these mice resulted in a significant (~40%) reduction of spleen weight (P<0.0001), compared to the control group of six mice. All mice tolerated the treatment well with no macroscopic toxicity; the maximal weight loss was 4% during the course of study of compound I.

Example 15

Mouse Model for Prevention and Treatment of Systemic Lupus Erythematosus (SLE)

This example illustrates a proposed study to examine the effect of apogossypol treatment on development of SLE in the New Zealand black×New Zealand white F1 (NZBW) and MRL/lpr mouse models.

Prevention Studies

Two genetically diverse strains, NZB/NZW F1 (which is genetically similar to B6.Sle1.Sle3 congenics) and MRL/lpr would be subjected to preventative studies from the age of 3 mo, to the age of 5 mo, i.e., for a 2 month period. Mice will be checked to ensure they are negative for anti-nuclear autoantibodies at the beginning of the study. In one example, 10 mice of each strain will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 mmol/kg to about 1.0 mmol/kg per day. The route of administration will be oral. However, intravenous administration can also be used.

The mice will be monitored at fortnightly intervals for serum autoantibody levels and 24-hour urine protein levels, and at monthly intervals for full blood counts, numbers and activation status of blood leukocytes (using flow cytometry). At the end of the study, all mice will also be examined for creatinine/BUN levels, spleen leukocyte counts and activation status, as well as histological severity of glomerular and interstitial lesions in their kidneys. Statistical analyses will be carried out to determine if the apogossypol treated mice have significantly reduced autoantibodies and leukocyte numbers/activation (primary outcome measures), or renal disease (secondary outcome measure). Finally, flow-sorted leukocyte populations from both study groups will be examined for the phosphorylation status of BCL-2, BCL-$X_L$, AKT, mTOR, Erk1,2, p38, CDK1/2, and NFkB, to ascertain if BCL-2 blockade also dampens other hyperactivated signaling pathways in lupus.

Treatment Studies

The same two genetically diverse strains, NZB/NZW F1 and MRL/lpr would be subjected to treatment studies from the age of 5 mo (once they are positive for anti-nuclear autoantibodies and become proteinuric), to the age of 7 months, i.e., for a 2 month period. 20 mice of each strain will receive apogossypol, whereas another 20 age/gender matched females will receive the vehicle ("placebo group"). Mice will be given from between about 0.2 µmol/kg to about 1.0 µmol/kg per day. The route of administration may be oral. However, intravenous administration can also be used. All mice will be tested to ensure they are positive for anti-nuclear autoantibodies at the beginning of the study. In one example, 10 mice will be sacrificed immediately after the treatment period, to examine for splenic leukocyte numbers/activation, whereas the remaining 10 mice in each group will be followed up till death (in order to ascertain the impact of apogossypol on mortality).

The mice will be monitored at fortnightly intervals for serum autoantibody levels and 24-hour urine protein levels, and at monthly intervals for full blood counts, numbers and activation status of blood leukocytes (using flow cytometry). At the end of the study, all mice will also be examined for creatinine/BUN levels, spleen leukocyte counts and activation status, as well as histological severity of glomerular and interstitial lesions in their kidneys. Statistical analyses will be carried out to determine if the apogossypol treated mice have significantly reduced autoantibodies, mortality and leukocyte numbers/activation (primary outcome measures), or renal disease (secondary outcome measure). Finally, flow-sorted leukocyte populations from both study groups will be examined for the phosphorylation status of BCL-2, BCL-$X_L$, AKT, mTOR, Erk1,2, p38, CDK1/2, and NFkB, to ascertain if BCL-2 blockade also dampens other hyperactivated signaling pathways in lupus.

Follow up studies will include: assessing the impact of BCL-2 blockade on selected lupus checkpoints, assessing whether the combined use of apogossypol and other conventional drugs might yield better therapeutic efficacy with reduced side-effects, assessing the level of generalized immunosuppression due to apogossypol, and assessing the level of BCL-2 family member activation in human lupus.

Example 16

Prevention of Experimental Autoimmune Encephalomyelitis (EAE) in the Murine Model of Multiple Sclerosis This example illustrates a proposed study to examine the effect of apogossypol treatment on development of both active and passive EAE in the murine model of multiple sclerosis.

Experimental allergic encephalomyelitis (EAE) is a T cell mediated autoimmune disease of the central nervous system (CNS). Disease can be induced in susceptible strains of mice by immunization with CNS myelin antigens or alternatively, disease can be passively transferred to susceptible mice, such as SJL/J mice, using antigen stimulated CD4+ T cells (Pettinelli, *J. Immunol.* 127, 1981, p. 1420). EAE is widely recognized as an acceptable animal model for multiple sclerosis in primates (Alvord et al. (eds.) 1984. Experimental allergic encephalomyelitis—A useful model for multiple sclerosis. Alan R. Liss, New York).

Prevention Studies

Female SJL/J mice would be subjected to preventative studies from the age of 7 to 10 weeks, i.e., for a 2 month period. In one example, 10 mice will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 µmol/kg to about 1.0 µmol/kg per day. The route of administration will be oral. However, intravenous administration can also be used.

a) Active EAE. Active EAE would be induced by immunization of female SJL/J mice with, for example, about 800 µg of mouse spinal cord homogenate ("MSCH") in complete Freund's adjuvant ("CFA") on days zero and seven; following the procedure described in Racke et al., *J. Neuroimmunol., Vol* 46:175-184, (1993).

b) Passive EAE. Passive EAE would be induced by adoptive transfer of myelin basic protein ("MBP")-sensitized T lymphocytes as follows: female SJL/J mice (four- to six-weeks-old) were immunized on days zero and seven with 400 µg of MBP in CFA. On day 14 the regional draining lymph node cells and spleen are harvested and cultured. The cells are cultured at about $4 \times 10^6$ cells/well in, for example, RPMI 1640 (Gibco, Gaithersburg, Md.) containing 10% fetal bovine serum (Hyclone Labs, Logan, Utah), 2 mM L-glutamine (Gibco, Gaithersburg, Md.), $5 \times 10^{-5}$ M 2-mercaptoethanol (Gibco, Gaithersburg, Md.), 1% penicillin/streptomycin (Gibco, Gaithersburg, Md.), and 100 µg/ml of MBP. After four days, viable T cell blasts are harvested, washed, and injected intraperitoneally into recipient mice ($1 \times 10^7$ to $1.5 \times 10^7$ cells in 500 µl of PBS).

The mice will be monitored at daily intervals for clinical signs of EAE and scored on a scale of 0 to 3 as follows: 0.5—Distal limp tail; 1.0—Complete limp tail; 1.5—Limp tail and hind limb weakness (unsteady gait); 2.0—Partial hind limb paralysis; 3.0—Complete bilateral hind limb paralysis. At the end of the study, all mice will also be examined for lymphocyte infiltration and demyelination of the spinal cord. Statistical analyses will be carried out to determine if the apogossypol treated mice have significantly reduced disease severity, inflammation and/or demyelination.

Example 17

Prevention and Treatment of Diabetes in the NOD/SCID Mouse Model

This example illustrates generally the proposed use of the NOD/SCID mouse model to test the ability of apogossypol to prevent or treat diabetes.

The non-obese diabetic (NOD) mouse is a model for autoimmune disease, in this case insulin-dependent diabetes mellitus (IDDM), which main clinical feature is elevated blood glucose levels (hyperglycemia). The elevated blood glucose levels are caused by the immune-mediated destruction of insulin-producing β cells in the islets of Langerhans of the pancreas. This destruction is accompanied by a massive cellular infiltration surrounding and penetrating of the islets (insulitis) by a heterogeneous mixture composed of a CD4+ and CD8+ T lymphocytes, B lymphocytes, macrophages and dendritic cells.

The NOD mouse model for inflammation was generally described previously. Female NOD mice spontaneously develop an IDDM-like disease with destruction of the β cells in the pancreas and spilling of glucose into the urine beginning around 12-14 weeks of age. A typical longitudinal histological examination of the NOD pancreas demonstrates infiltrating cells surrounding the blood vessels at 3-4 weeks of age, but the islets are typically still clear at 6-7 weeks. Infiltrating cells than reach the islets, either surrounding them or accumulating at one pole. Between 10 and 12 weeks, the infiltrating cells penetrate into the islets and the islets become swollen with lymphocytes. The easiest and most reliable way to detect the onset of diabetes in these mice is to test for glucose levels in the blood.

Diabetes can be assessed by measurement of venous blood using, for example, an Abbott Medisense Precision Q.I.D. glucometer and also monitored for glucosuria (Gluketur Test; Boehringer Mannheim, Mannheim, Germany). Animals will be considered diabetic after two consecutive glucose measurements of higher than about 13.75 mmol/l (250 mg/dl). Onset of diabetes will be dated from the first consecutive reading. In instances of sustained hyperglycemia of >33 mmol/l animals will be sacrificed to avoid prolonged discomfort.

Prevention Studies

NOD/LtJ mice (Jackson Laboratories) would be subjected to preventative studies from the age of about 8-10 weeks, for a 2 month period. Mice will be checked to ensure they are negative for IDDM-like disease symptoms at the beginning of the study. In one example, 10 will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 µmol/kg to about 1.0 µmol/kg per day. The route of administration may be oral; intravenous administration can also be used.

The mice will be monitored at daily intervals for blood glucose levels and 24-hour urine protein and glucose levels, and at monthly intervals for full blood counts, numbers and activation status of blood leukocytes (using flow cytometry). At the end of the study, all mice will also be examined for insulin levels, presence of CD4+ and CD8+ T lymphocytes, B lymphocytes, macrophages and dendritic cells in the pancreas, as well as general morphology of the pancreas. Statistical analyses will be carried out to determine if the apogossypol treated mice have significantly delayed onset of diabetes.

Treatment Studies

NOD/LtJ mice would be subjected to treatment studies beginning at about 10-12 weeks of age. 20 mice will receive apogossypol, whereas another 20 age/gender matched females will receive the vehicle ("placebo group"). Mice will be given from between about 0.2 µmol/kg to about 1.0 µmol/kg per day. The route of administration will be oral; intravenous administration can also be used. All mice will be tested to ensure they are positive for IDDM-like disease (i.e., two consecutive glucose measurements of higher than about 13.75 mmol/l (250 mg/dl)) at the beginning of the study. In one example, 10 mice will be sacrificed immediately after the treatment period, to examine for pancreas morphology and presence of lymphocytes in the pancreas, whereas the remaining 10 mice in each group will be followed up till death (in order to ascertain the impact of apogossypol on mortality).

The mice will be monitored at daily intervals for blood glucose levels and 24-hour urine protein and glucose levels, and at monthly intervals for full blood counts, numbers and activation status of blood leukocytes (using flow cytometry). At the end of the study, all mice will also be examined for insulin levels, presence of CD4+ and CD8+ T lymphocytes, B lymphocytes, macrophages and dendritic cells in the pancreas, as well as general morphology of the pancreas. Statistical analyses will be carried out to determine if the apogossypol treated mice have significantly reduced blood glucose levels, urine glucose levels, and mortality and leukocyte numbers/activation.

Follow up studies will include: assessing the impact of BCL2 blockade on selected IDDM-like disease checkpoints, assessing whether the combined use of apogossypol and other conventional drugs might yield better therapeutic efficacy with reduced side-effects, assessing the level of generalized immunosuppression due to apogossypol, and assessing the level of BCL2 family member activation in human diabetes.

Example 18

Studies of Apogossypol Activity and Toxicity in BCL-2 Transgenic Mice

The toxicity and efficacy studies were conducted in mice to compare gossypol and apogossypol. At daily dose of 0.12 mmol/kg p.o., % mortality in gossypol-treated Balb/c mice was 100% by the end of week 3. Gossypol-treated mice developed the following toxicities: GI toxicity (partial paralytic ileus), hematological toxicity (lymphopenia), hepatotoxicity (elevation of serum levels of ALT and AST), weight loss and cardic toxicity, and cause of death was cardiac failure in gossypol-treated mice.

Figure 5A:
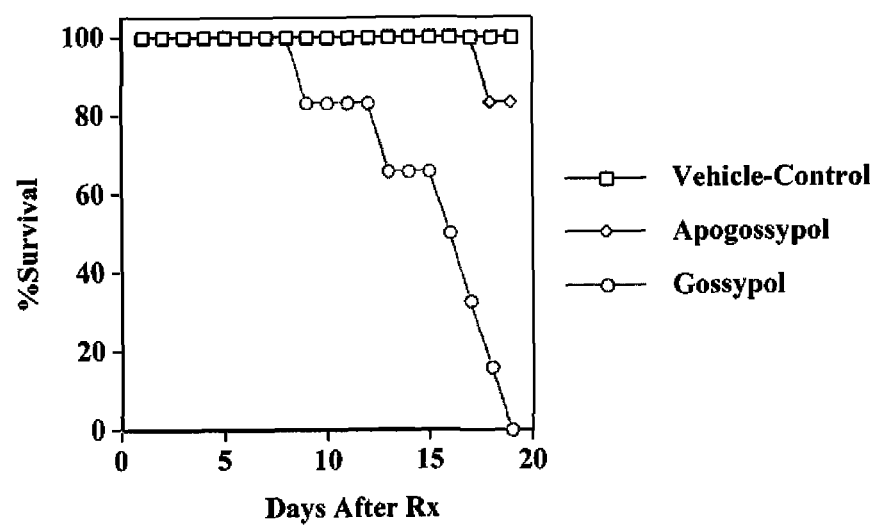
FIGS. 5A and 5B depict toxicity profiles of gossypol vs. apogossypol.
Figure 5B:
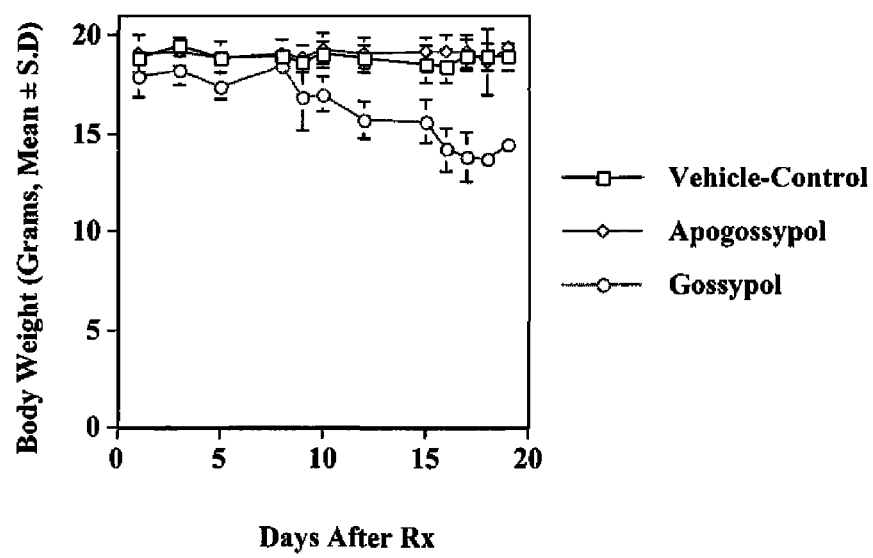

FIGS. 5A and 5B further illustrate toxicity profiles of gossypol vs. apogossypol. FIG. 5A shows % survival in young, healthy Balb/c mice (7-weeks-old females, 6 mice per group). Mice were orally administered with apogossypol, gossypol or vehicle-control at a daily dose of 0.12 mmol/kg, QD×5 for three weeks. % survival dropped to 0 by the end of 3 weeks of treatment with gossypol, whereas % survival remained high among groups treated with apogossypol or vehicle-control.

FIG. 5B illustrates changes in body weight, which were monitored throughout the entire period of treatments with apogossypol, gossypol or vehicle-control at a daily dose of 0.12 mmol/kg, QD×5 for three weeks. Data expressed in grams (Mean±Standard Deviation).

As can be seen from the data provided by FIGS. 5A and 5 B, apogossypol was less toxic than gossypol in all these categories and apogossypol did not induce any abnormal changes in E.C.G. pattern throughout the entire period of treatment. Gossypol-treated mice became lethagic with scruffy hair, whereas apogossypol or vehicle-control-treated mice remained active and apparently healthy without weight loss throughout the treatment period. Apogossypol-treated mice as well as vehicle-control mice (0.12 mmol/kg ascorbic acid in sesame oil) revealed normal E.C.G.-pattern, using 2-electrodes, by the use of MP150 Biopac system (the third electrode=ground). In addition, apogossypol-treated mice as well as vehicle-control mice exhibited normal bowel movement in ultrasound imaging-Cinema (300 frames), while no weight loss was noted during the entire course of treatment. One of 6 apogossypol-treated mice was found dead on day 18 of treatment. This mouse was apparently healthy until the day before death, and cause of death is unknown at this moment.

Apogossypol was well-tolerated in nude mice grafted with SCLC H146 cell line at daily dose of 0.24 mmol/kg, p.o. (no fatality and no weight loss), and anti-tumor effect of apogossypol was demonstrated. Ascorbic acid-stabilized apogossypol was stable for 2.5 weeks when stored at 4° C. or at room temperature under nitrogen gas or air, with or without light.

Toxicity

It was determined that apogossypol is less toxic than gossypol. The toxicities of gossypol and apogossypol were compared in normal female Balb/c mice. Preliminary maximum tolerated dose (MTD) studies suggested that apogossypol was less toxic than gossypol whether delivered orally or by intraperitoneal injection. Previous NCI-sponsored studies determined that racemic gossypol and (−)gossypol are nonlethal and show anti-tumor activity when dosed orally at 0.06 mmol/kg daily for up to 21 days. Thus, orally administered gossypol and apogossypol were compared at twice this dose; animals were dosed with 0.12 mmol/kg. Ascorbic acid was employed as a control, because apogossypol is formulated at 1:1 molar ratio with this weak acid, which renders the compound stable upon storage. Compounds or vehicle control were dosed 15 times over 3 weeks, giving compounds daily for 5 consecutive days (Monday-Friday), resting on weekends.

BCL-2 Transgenic Mice

Transgenic mice expressing BCL-2 have been described as the B6 line. The BCL-2 transgene res a mini-gene version of a t(14;18) translocation in which the human BCL-2 gene is fused with the immunoglobulin heavy-chain (IgH) locus and associated IgH enhancer. The transgene was propagated on the Balb/c background.

Patient Specimens

Peripheral blood mononuclear cells (PBMC) from patients with CLL were obtained from the CLL Research Consortium (CRC) tissue bank (San Diego, Calif.). The blood samples were collected after obtaining informed consent. PBMC were isolated by density gradient centrifugation using Histopaque 1077 (Sigma, St. Louis, Mo. 63178). All patients met the NCI IWCLL criteria for diagnosis of CLL. The samples used contained ≧95% CD19 and CD5 positive cells, as assessed by flow cytometry. CLL samples were cultured in RPMI media containing 10% fetal bovine serum (FBS) (HyClone, Logan, Utah 84321 or Mediatech Inc., Herndon, Va. 20171) at 37° C. in 5% $CO_2$:95% air.

Gossypol and Apogossypol Preparation and Formulation

Apogossypol (NSC736630) was co-crystallized with ascorbic acid at 1:1 molar ratio. Gossypol (NSC19048) was lyophilized in acetic acid form. Both compounds were provided by NCI-DTP (RAID-program). Compounds were dissolved in 100% sesame oil just before oral administration. Vehicle-control consisted of corresponding concentration of ascorbic acid suspended in 100% sesame oil.

Mouse Experiments

Gossypol and apogossypol were administered orally to mice daily at doses of 0.06 mmol/kg or 0.12 mmol/kg, using a straight-type oral gavage needle (18G-3" Straight 2.25 mm ball, Braintree Scientific, Inc.). The volume of administration was 10 ml/kg, i.e., typically 0.2 mL per 20 gm mouse. Normal Balb/c mice of 7 to 8 weeks of age at the initiation of the study were employed for toxicity studies, while BCL-2 transgenic mice on Balb/c background of >6 months age were employed for efficacy studies. Age-matched, sex-matched mice were typically dosed 5 times weekly, using a regiment of daily dosing 5 consecutive days (Monday through Friday), followed by resting for 2 days, before resuming dosing. For BCL-2 transgenic mice, spleen-size was longitudinally monitored either by Ultrasound Imaging (Visualsonics) weekly and by physical examination using a digital caliper. At conclusion of treatments, mice were sacrificed via intra-peritoneal (i.p.) injection of 0.7 ml of Avertin and whole blood was collected into Yellow-Top Serum Separator tubes (Becton Dickinson Vacutainer Systems Becton Dickinson and Company, Franklin Lakes, N.J. 07417-1885). Spleens were removed and weighed.

Hematology Studies

Whole blood (250 µl) was collected in EDTA-coated glass tubes (purple top; MICROTAINER Brand Tube with EDTA, Catalogue #365973, Becton, Dickinson and Company, New Jersey 07417-1885) via either cardiac puncture or severing the brachial artery of anesthetized mice. After thorough mixing, specimens were analyzed using a VetScan HM2 (Abaxis Inc., Union City, Calif. 94587) hematology analyzer, measuring white blood cell count (WBC), red blood cell count (RBC), platelet (PLT) count, leukocyte differential (including % lymphocyte, % monocyte and % granulocyte), hematocrit (Ht), and hemoglobin (Hb).

Figure 6A:
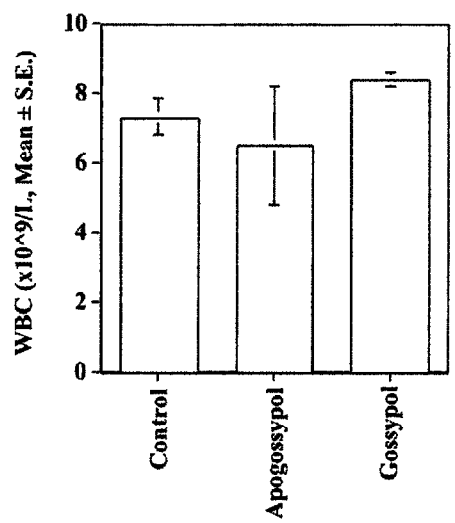
FIGS. 6A-6C depict hematological profiles of mice treated with apogossypol or gossypol.
Figure 6A:
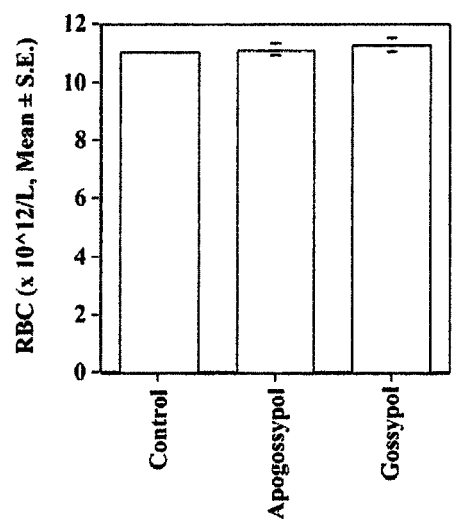
Figure 6B:
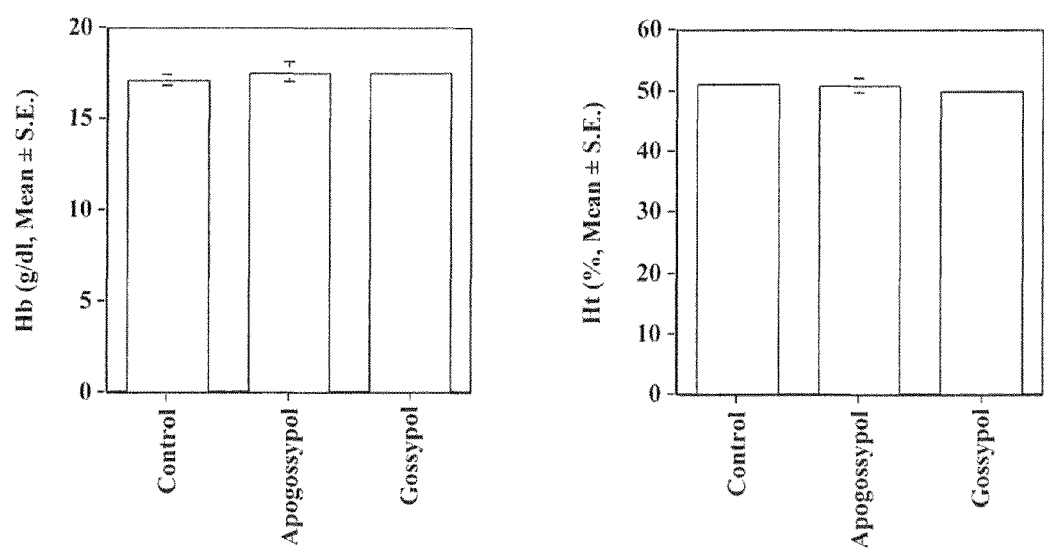
Figure 6C:
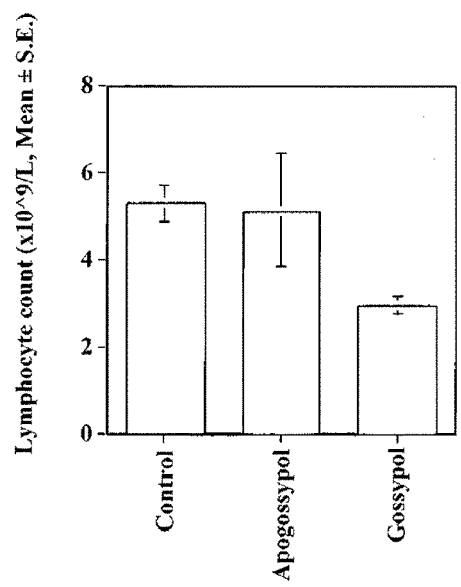
Figure 6C:
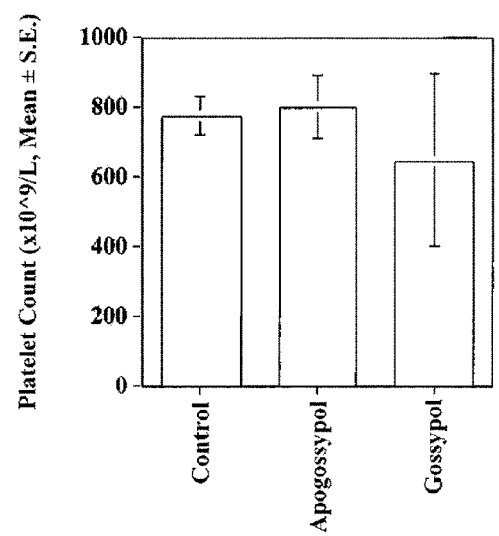

FIGS. 6A-6C illustrate hematological profiles of mice treated with apogossypol or gossypol. Mice were orally administered with apogossypol, gossypol or vehicle-control at a daily dose of 0.12 mmol/kg, QD×5 for three weeks (6 mice per group). Hematological profiles were analyzed by the use of an automated HM2 hematology analyzer (Abaxis Inc., Union City, Calif. 94587) at conclusion of therapy with vehicle-control or apogossypol or at the time of death in mice treated with gossypol.

Figure 2:
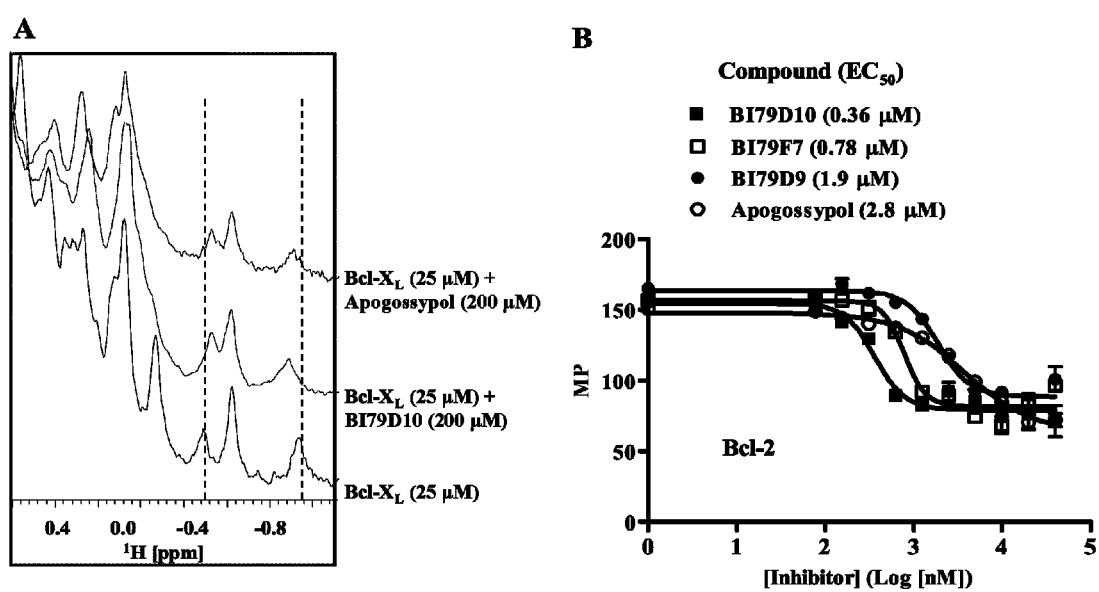
FIG. 2 demonstrates, NMR binding studies (A) and inhibiting activity of some compounds of the disclosure (B).
Figure 3:
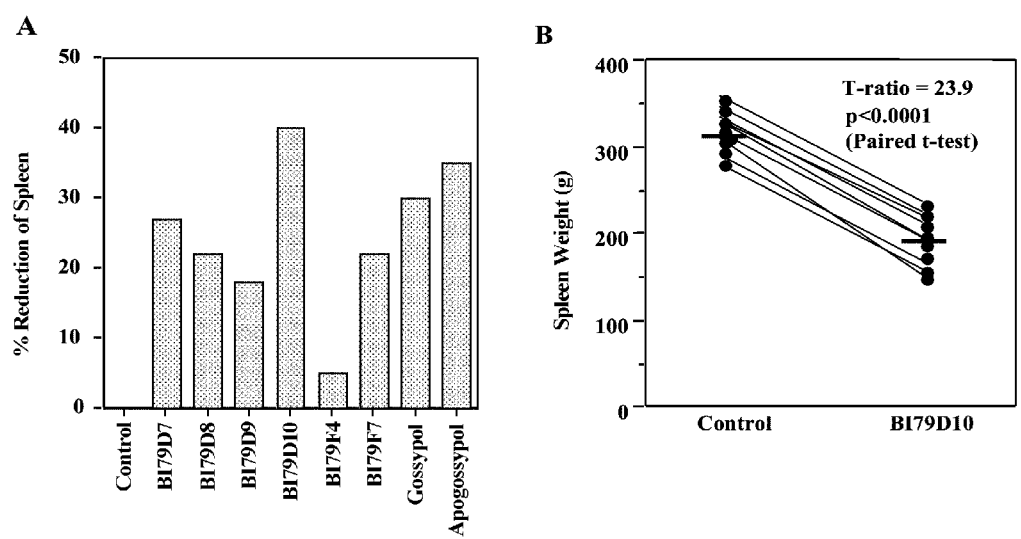
FIG. 3 demonstrates effectiveness of compounds of the disclosure on shrinkage of BCL-2 mouse spleen.
Figure 4:
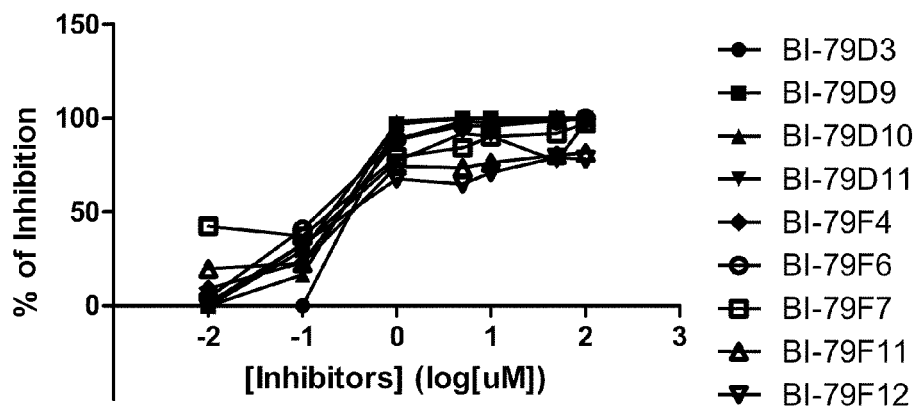
FIG. 4 demonstrates FP competitive binding curves of compounds of the disclosure using BCL-$X_L$.

FIG. 6A shows WBC (left Panel) and RBC (right panel). As can be seen, both WBC and RBC were unaffected by treatments with gossypol and apogossypol. FIG. 6B shows dtata for hemoglobin (Hb)(left panel) and for hematocrit (Ht)(right panel). As can be seen, both Hb and Ht were unaffected by treatments with gossypol and apogossypol. Finally, FIG. 2C provides data for lymphocyte count (left panel) and for platelet count: (right panel). As can be seen, gossypol induced lymphopenia, whereas apogossypol did not induce lymphopenia in Balb/c mice.

Serum Chemistry

Approximately 500 µl of whole blood was collected in glass tubes (yellow-top; MICROTAINER Brand, Serum Separator Tube, Catalogue #365956, Becton Dickinson and Company, Franklin Lakes, N.J. 07417-1885) and kept on ice for 30 minutes, then centrifuged at 12,000 r.p.m. (Eppendorf Centrifuge 5415C) for 2 minutes to separate serum from cells and fibrin clot. The resulting serum specimens were analyzed using an automated blood chemistry analyzer ("COBAS MIRA Classic"; Roche, Indianapolis, Ind. 46250-0414) to measure alanine aminotransferase (ALT) and aspartate aminotransferase AST), blood urea nitrogen (BUN), and Creatine.

Figure 7:
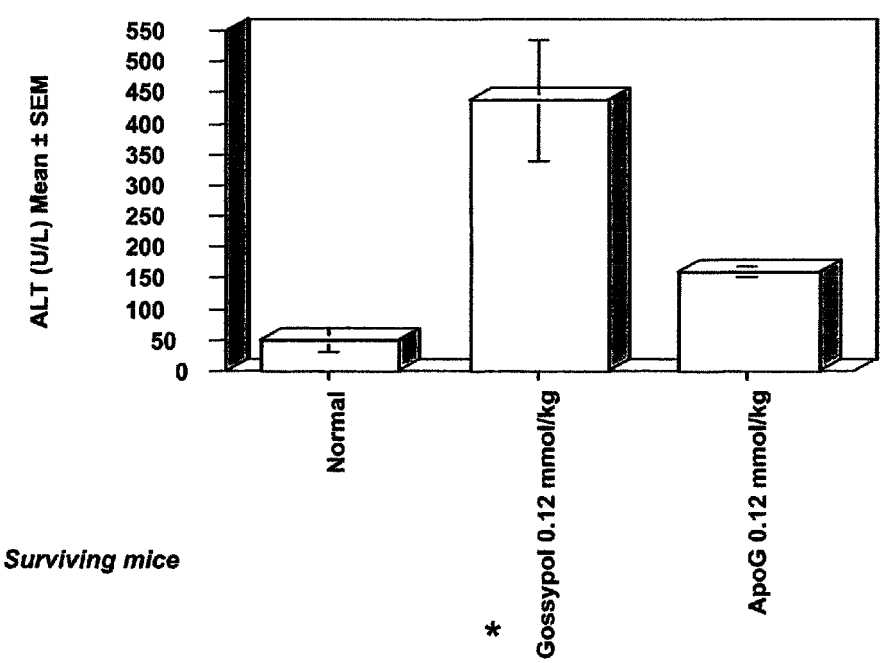
FIG. 7 depicts reactive blood chemistry profiles of mice treated with apogossypol or gossypol.

FIG. 7 provides the experimental data illustrating reactive blood chemistry profiles of mice treated with apogossypol or gossypol. Mice were orally administered with apogossypol, gossypol or vehicle-control at a daily dose of 0.12 mmol/kg, QD×5 for three weeks (6 mice per group). As can be seen, gossypol induced elevation of serum levels of ALT and apogossypol was less hepato-toxic than gossypol.

Ultrasound Imaging

Stomach and intestines were examined also imaged by ultrasound for evidence of dilation, an indication of GI toxicity. Briefly, mice were anesthetized using a mixture of isofluorane (5%) and oxygen gas (95%), restrained on a heated table using Aquagel Lubrication Gel (Parker Laboratories, Inc., Fairfield, N.J. 07004), and abdominal hair was removed with a chemical depilation agent (Nair™ Hair Removal, Church & Dwight Co., Inc., Princeton, N.J. 08543). Aquasonic 100 Ultrasound Transmission Gel (Parker Laboratories, Inc., Fairfield, N.J. 07004) was applied to the abdomen prior to imaging using a high-frequency probe to assess gas and intestinal distention.

Cardiac Toxicity

Immediately after ultrasound imaging, electrocardiogram (ECG) analysis of anesthetized mice was performed using a MP150 Biopack System.

Histology

Vital organs, including liver, kidneys, spleen, heart, stomach, small intestines, large intestines and lungs, were fixed in z-FIX solution for 3 days, rinsed 3 times with phosphate-buffered saline (PBS) [pH 7.4], and then embedded in paraffin-blocks. Thin sections were cut (0.5 um), stained with hematoxylin-eosin (H&E), and evaluated by light microscopy for histological abnormalities. In addition, unstained sections were analyzed by the terminal deoxynucleotidyl transferase end-labeling (TUNEL) method to stain cells with DNA fragmentation indicative of apoptosis.

Splenocyte Isolation

Spleens were excised from sacrificed mice and cell suspensions treated with a mouse erythrocyte lysing kit (R & D Systems). Total splenocyte count was determined by trypan blue dye exclusion assays using hemocytometers. The percentage of B-lymphocytes was determined by fluorescence activated cell sorter (FACS) analysis (FACS-CANTO, Bectin-Dickinson Inc., Mountain View, Calif.) following staining cells with Phyco-Erythrin (PE)-conjugated anti-CD19 or -B220 antibodies (Becton Dickinson, San Jose, Calif. 95131).

Cell Culture and Cytotoxicity Studies

Splenocytes were suspended at $1\times10^6$ cells/mL in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Human B-CLL cells and 3 B-NHL cell lines, including RS11846, DOHH2 and 380 cells, were cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of Gossypol, ApoGossypol, or ascorbic acid for 1-2 days. The percentage of viable cells was determined by Annexin V- and propidium iodide (PI)-labeling, using an Apoptosis Detection kit (BioVision Inc.), analyzing stained cells by flow cytometry (FACSort; Bectin-Dickinson, Inc.; Mountain View, Calif.). Cells that were annexin-V-negative and PI-negative were considered viable.

Figure 8:
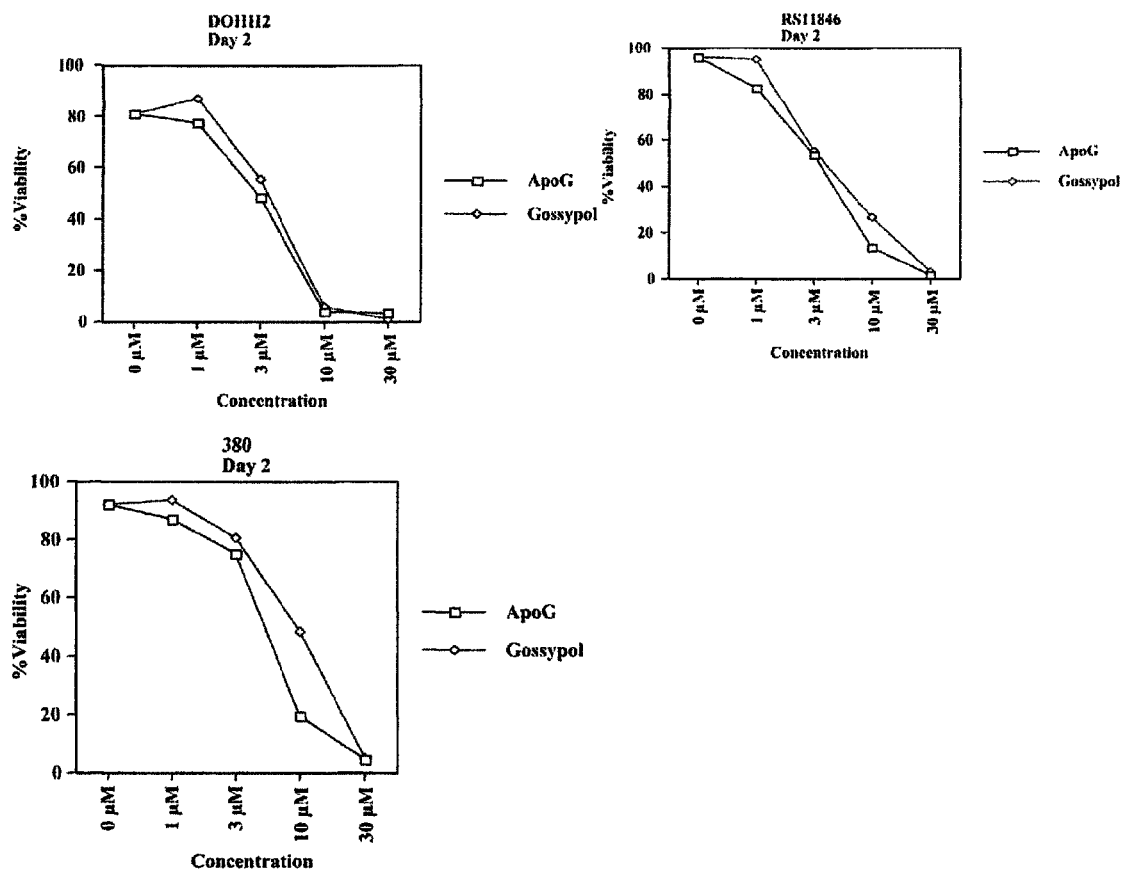
FIG. 8 depicts a comparison of apoptosis induction of NHL B-cell lines, including DOHH2, RS11846 and 380, by apogossypol and gossypol.

FIG. 8 provides the experimental data illustrating a comparison of apoptosis induction of NHL B-cell lines, including DOHH2, RS11846 and 380, by apogossypol and gossypol. NHL B-cell lines, including DOHH2, RS11846 and 380, were cultured in RPMI medium containing 10% fetal bovine serum (FBS) for 48 hours, in the absence and presence of various concentrations of gossypol and apogossypol as indicated in the figures.

After 48 hours of incubation, % viability was determined by FACSort after staining cells by the use of an Annexin V-FITC/PI Apoptosis Detection kit (BioVision Inc.). Viable cells were defined by Annexin V-negative, PI-negative cells. DOHH2 and RS11846 cell lines were slightly more sensitive to gossypol and apogossypol in vitro with IC50 of approximately 3 µM, whereas 380 cell line was slightly more resistant to gossypol and apogossypol. In all three NHL B-lymphoma cell lines, apogossypol was slightly more potent than gossypol, but their potencies were roughly comparable.

Figure 9:
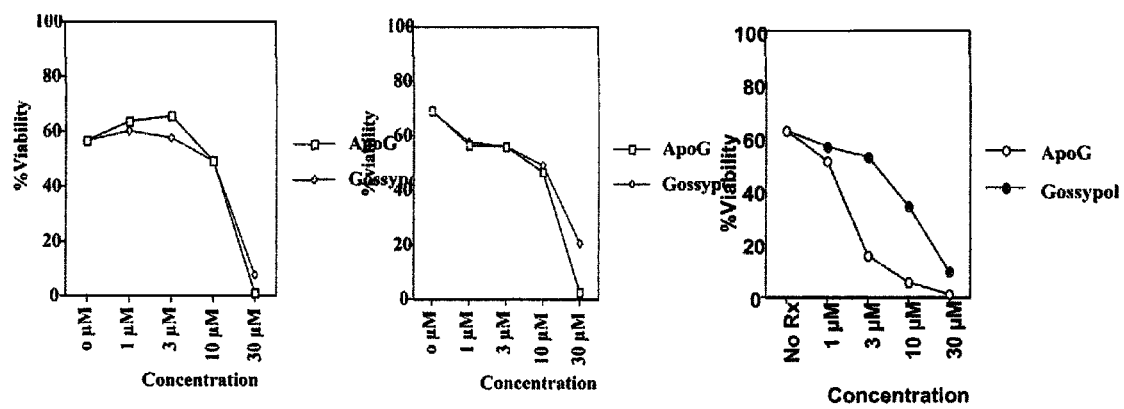
FIG. 9 depicts a comparison of activity of gossypol and apogossypol against cultured murine B-cells from transgenic mice: BCL-2 vs. BCL-2/TRAF2DN.

FIG. 9 provides the experimental data illustrating a comparison of activity of gossypol and apogossypol against cultured murine B-cells from transgenic mice: BCL-2 vs. BCL-2/TRAF2DN. Spleen tissues were removed from BCL-2 transgenic mice and BCL-2/TRAF2DN mice, and splenocytes were isolated by the use of a mouse erythrocyte lysing kit (R & D Systems) according to the manufacturer's manual.

Splenocytes were cultured in RPMI medium containing 10% fetal bovine serum (FBS) for 18 hours, in the absence and presence of various concentrations of gossypol and apogossypol as indicated in the figures. After 18 hours of incubation, % viability of splenocytes was determined by FACSort after staining cells by the use of an Annexin V-FITC/PI Apoptosis Detection kit (BioVision Inc.). Viable cells were defined by Annexin V-negative, PI-negative cells. In BCL-2 transgenic mouse, apogossypol was several-fold more potent than gossypol in induction of apoptosis against cultured B-cells with IC50 of roughly 1-2 µM for apogossypol vs. 10 µM for gossypol. In contrast, murine B-cells from Bcl-2/TRAF2DN mice were roughly 10-fold more resistant to both apogossypol and gossypol than Bcl-2 transgenic mice.

Figure 10:
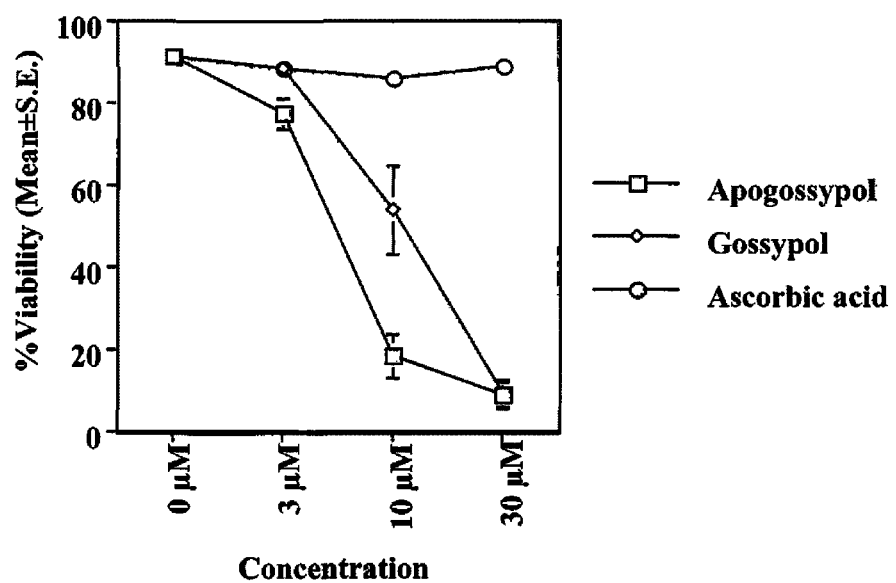
FIG. 10 depicts a comparison of apogossypol and gossypol induction of apoptosis of cultured CLL B-cells.

FIG. 10 provides the experimental data illustrating a comparison of apogossypol and gossypol induction of apoptosis of cultured CLL B-cells. CLL samples were incubated in RPMI media containing 10% fetal bovine serum (FBS) at 37° C. with 5% CO2 for 48 hours, in the absence or presence of various concentrations of gossypol and apogossypol as indicated in the figures.

After 48 hours of culture, % viability was determined by FACSort after staining cells by the use of an Annexin V-FITC/PI Apoptosis Detection kit (BioVision Inc.). Viable cells were defined by Annexin V-negative, PI-negative cells. Apogossypol was approximately 3-fold more potent than gossypol against cultured CLL B-cells in vitro. There was significant difference in apoptosis induction between apogossypol group and gossypol group ($p<0.025$) by two-way ANOVA analysis.

Figure 11A:
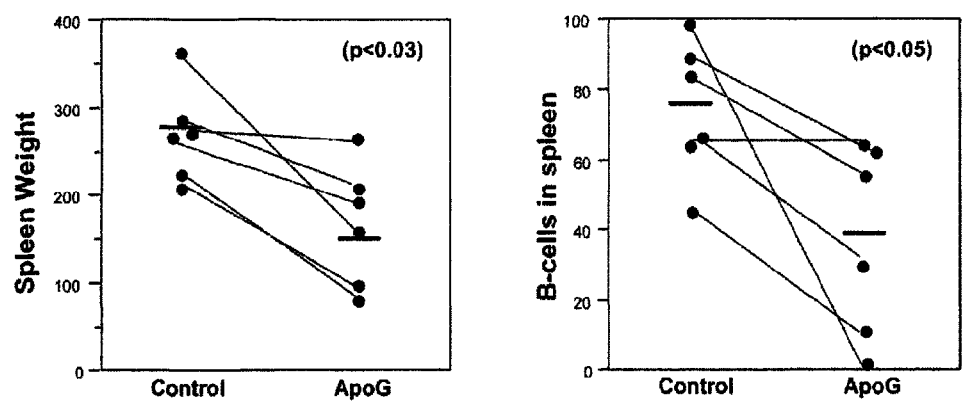
FIGS. 11A and 11B depict apogossypol activity in BCL-2 transgenic mice.
Figure 11B:
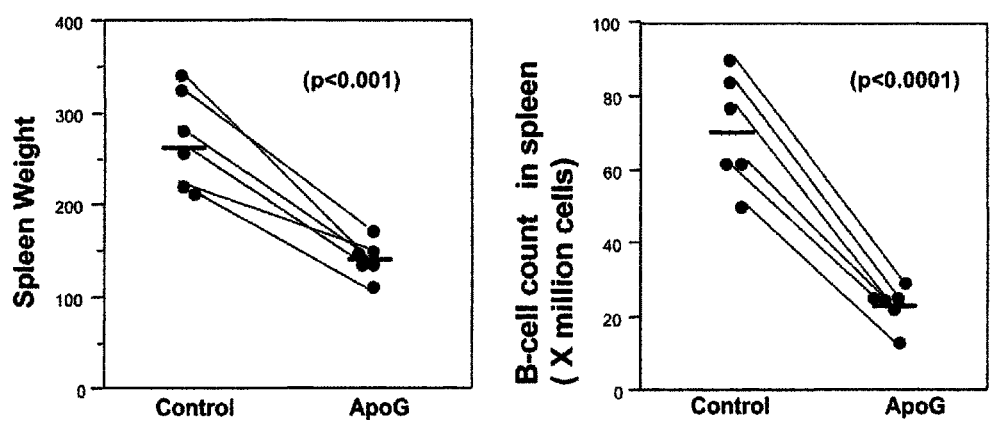

FIGS. 11A and 11B provide the experimental data illustrating apogossypol activity in Bcl-2 transgenic mice. FIG. 11A shows the results of a low dose study (at 0.06 mmol/kg) and FIG. 11B—a high dose study (at 0.12 mmol/kg). Age-matched and sex-matched BCL-2 transgenic mice were used for efficacy studies. BCL-2 transgenic mice spontaneously developed low grade B-cell lymphoma as characterized by splenomegaly, as a function of time. In BCL-2 transgenic mice, the disease progression can be divided into two stages; at the first stage, the disease is characterized by splenomegaly as a result of expansion of B-cells in spleen due to overexpressed BCL-2 in B6 mice, and at the second stage, another genetic hit(s) may strike, resulting in disseminated lymphoma as characterized by bulky lymphadenopathy as well as splenomegaly.

In this study, BCL-2 transgenic mice at the first stage were used for this efficacy study. In a separate study with untreated BCL-2 transgenic mice, wet weight of spleen ranged from 195-mg to 335-mg, and wet weight of spleen was found to be nearly comparable in age-matched, sex-matched BCL-2 transgenic mice. Apogossypol stabilized with ascorbic acid at 1:1 molar ratio, gossypol stabilized with acetic acid at 1:1 molar ratio and vehicle-control (ascorbic acid in 100% sesame oil) were orally administered to BCL-2 transgenic mice once daily (QD×5) for 3 weeks, consecutively. At conclusion of treatment, BCL-2 transgenic mice were sacrificed via intraperitoneal injection of 0.7 ml of avertin (anesthetic solution) and spleen was removed and weighed. Splenocytes were isolated by the use of mouse erythrocyte lysing kit (RD Systems). Total splenocyte count was determined by trypane blue exclusion assays. % B-cell count was determined by FACS analysis after staining cells with CD-5, a B-cell marker. Reactive data are shown by FIGS. 11A and 11B.

As can be seen from FIG. 11A, at a low dose of 0.06 mmol/kg, both gossypol and apogossypol were well tolerated and induced shrinkage of splenomegaly, as evidenced by reductions in wet weight of spleen as well as B-cell count in spleen. Apogossypol induced shrinkage of spleen to a significant extent ($p<0.03$ for wet weight of spleen, $P<0.05$ for splenic B-cell counts), whereas gossypol induced shrinkage of spleen to a considerable extent but not significantly.

As can be seen from FIG. 11B, at a high dose of 0.12 mmol/kg, gossypol was not tolerated in BCL-2 transgenic mice, whereas apogossypol was well tolerated in Bcl-2 transgenic mice at a high dose of 0.12 mmol/kg. Apogossypol induced shrinkage of splenomegaly to a significant extent ($p<0.001$ for wet weight of spleen, $P<0.0001$ for splenic B-cell counts). Age-matched, sex-matched BCL-2 transgenic mice were evaluated for shrinkage of spleen after conclusion of apogossypol therapy and spleen size was reduced roughly by half at a daily dose of 0.12 mmol/kg.

Example 19

Evaluation of the Cytotoxic Activity of the Compounds on Human Tumors Cells

This example illustrates the efficacy of gossypol on human tumor cells. To evaluate the cytotoxic activity of the compounds on human tumors cells, their biological activities were tested using XTT dye reduction assays using two breast cancer cell lines: MCF7 (high expressor of BCL-2/BCL-$X_L$) and ZR75-1 (low expressor of BCL-2/BCL-$X_L$). Gossypol is a cytotoxic agent for MCF7 and ZR75-1 cells, reducing cell viability in a dose-dependent manner, with $IC_{50}$ values of 13.2 µM and 8.4 µM, respectively. Purpurogallin, however, did not show appreciable activity in these assays, potentially due to its hydrophilic character (ClogP-0.7).

Consistent with this observation, a purpurogallin derivative 5D1 that is predicted to have better cell-membrane permeability properties (based on its ClogP of ~2.5) reduced cell viability in a dose-dependent manner, with $IC_{50}$ value of ~50 µM the ZR75-1 cell line (not shown). Therefore, the cellular activities of the compounds were evaluated in HeLa cells, which are known to be less selective for compounds uptake. The inhibition data obtained with HeLa cells viability assays parallel the in vitro binding data with BCL-$X_L$, with a correlation coefficient of r=0.9 (p=0.001).

Docking studies with FlexX software (Kramer et al., *Proteins*, 37:228 (1999)) implemented in Sybyl (TRIPOS) using the BCL-$X_L$ conformation found in the complex with Bak-peptide showed an optimal location for gossypol in the deep hydrophobic cleft normally occupied by the Bak helical BH3 peptide in the complex. Both the (+) and the (−) stereoisomers of gossypol were docked, as these exhibited different activity in previous cell-based assays which showed that (−) gossypol is ten times more effective than (+) gossypol as a cytotoxic agent. The goodness of the fit as measured by a scoring function, and the intermolecular energy after minimization with the DOCK routine of Sybyl, was considerably better for (−) gossypol (−32.7 Kcal/mol) versus (+) gossypol (−25 Kcal/mol), in agreement with these observations. The overall positioning of both stereoisomers of Gossypol is very similar.

Fluorescence Polarization Assays (FP A)

FP A assays were conducted with a fluorescein-labeled Bad peptide (NL W AAQRYGRELRRMSD-K(FITC)-FVD)

(Synpep Corporation, Dublin, Calif.) using a LJL Analyst HT (Molecular Devices Co., Sunnyvale, Calif.). Dilution buffer for all stocks and samples was 50 µM Tris-Bis pH 7.4, 0.01% bovine gamma globulin. A series of two-fold dilutions of Gossypol were prepared, i.e., 100 µM, 50 µM, down to 0.1 µM in dilution buffer. To each tube was added a solution containing 30 nM of BCL-$X_L$ and 4 nM fluoresceinated peptide. The tubes were incubated for 5 minutes at room temperature and 20 µl each of reaction mixture was transferred to 96-well black PS, HE Microplate (LJL Biosystems Co). All assays were performed in quadruplicate, with blank wells receiving no Gossypol. Then, the plate was read for total intensity and polarization (in mP units) was measured. Controls included dose-responses measurements in absence of the proteins, to assess any interactions between the compounds and the FITC-BH3 peptide. Eventual effects were taken into account by subtraction.

NMR Spectroscopy

2D [$^{15}$N, $^{1}$H]-TROSY spectra for BCL-$X_L$ were measured with 0.5 mM samples of $^{15}$N-labeled BCL-$X_L$. $^{15}$N-labeled and unlabeled BCL-$X_L$ were prepared and purified according to known methods. For chemical-shift mapping and docking studies the three-dimensional structure of BCL-$X_L$ in complex with Bak peptide (PDB code 1BXL) was used. In addition to chemical-shift mapping with labeled proteins, $T_{1p}$ measurements and saturation transfer experiments such as WaterLOGSY experiments were also performed to further validate the binding of the studied compounds to BCL-$X_L$.

All experiments were performed with a 500 MHz Varian Unity+ spectrometer or a 600 MHz Bruker Avance600 spectrometer, both equipped with four rf channels and z-axis pulse-field gradients. Selective water saturation was performed with a train of selective IBURP2 pulses of 7 ms durations spaced by a 10 ms delay. Total saturation time used was 2.5s $T_{1p}$ series were measured with a spin-lock pulse of variable length. Measurements were then performed with 1 ms, 10 ms, 50 ms, 150 ms, 200 ms, 250 ms and 300 ms spin-lock time with 100 µM compounds in the absence and presence of 10 µM protein. In all experiments, de-phasing of residual water signals was obtained with a WATERGATE sequence.

Molecular Modeling

Molecular modeling studies were conducted on several R12000 SGI Octane workstations with the software package Sybyl version 6.9 (TRIPOS). The docked structure of Gossypol was initially obtained by FlexX as implemented in Sybyl. Two calculations were performed. In the first, all binding-site torsion angles were kept fixed, while in the second side-chain torsion angles were free to change. The average scoring function for the 30 best solutions was slightly lower when the side-chains were free to rotate. The position of the side-chains in the model did not change substantially from the initial values. The scoring function for (+) gossypol was inferior to (−) gossypol, but the overall positioning of both stereoisomers was very similar.

The resulting best scoring structures were subsequently energy minimized by using the routine DOCK of SYBYL keeping the site rigid. The energy of the ligands after the DOCK minimization was within 5 Kcal/mol from their global minimum of energy. Superposition of compounds was obtained by the routine MULTIFIT of SYBYL. Color figures showing three-dimensional structures were prepped with the programs SYBYL and MOLMOL.

Inhibitory Effect of Compounds on Cancer Cell Survival

The effects of the compounds on viability of tumor cells in culture were monitored by using XTT assays with MCF7 and ZR75-1 cell lines. MCF7 cells were grown in DMEM containing 10% fetal bovine serum, penicillin/streptomycin, supplemented with $10^{-10}$ M insulin, 1 mM sodium pyruvate and glutamine. ZR75-1 cells were grown n RPMI containing 10% fetal bovine serum, penicillin/streptomycin, supplemented with HEPES buffer, 1 mM sodium pyruvate and glutamine. Cells were regularly tested for mycoplasma contamination. Cells were seeded triplicates at an initial cell density of 1,000 cells per well. Blank wells received no cells.

Gossypol, purpurogallin and 5D1 were added at final concentrations of 0, 1, 10 and 100 µM and incubated for three days. Relative numbers of viable cells was determined by XTT assay. Briefly, in a 96-well plate, we added 50 µl of a mixture of 1 mg/ml of XTT (2,3-bis(2-methoxy-4-nitro-5-sulfophenyl)-5-[(phenylamino)carbonyl]-2H-tetrazolium hydroxide) (Polysciences, Washington, Pa.) containing 0.025 mM PMS (phenazine methosulfate) to each well. The 96-well plates were reincubated for an additional 4 hours to allow for XTT formazan production. Then, the contents of each plate were mixed and optical densities were determined at a wavelength of 450 nm ($OD_{450}$). Net $OD_{450}$ was determined after subtracting $OD_{450}$ of blank wells. Low-passage HeLa cells (between passage number 10 and 20) were transfected with pcDNA3-BCL-$X_L$ or control pcDNA3 plasmids using Lipofectamine Plus reagent (Invitrogen) and selected in medium containing 800 µg/ml of G418. Immunoblot analysis of BCL-$X_L$ was accomplished as previously described. HeLa-transfectants were treated with various doses of gossypol, purpurogallin, and its derivatives (0,1,3,10 and 100 µM).

Chemicals

Pure polyphenols were obtained from SIGMA (gossypol and purpurogallin) and/or from Microsource Discovery Systems (Purpurogallin derivatives). Reference compounds were obtained from Chembridge Corp. (San Diego). Gossypol was tested as a racemic mixture of (+) and (−) isomers. Compounds were dissolved in DMSO at 100 mM concentration and stored at −20 DC. NMR analysis was periodically performed on the compounds as a quality control, prior to further dilution for binding and displacement assays. Reactivity of Gossypol was tested with a 15N-labeled test protein (BIR3 domain of XIAP). A solution containing 1 mM gossypol and 200 µM N-labeled BIR3 was incubated for two hours and the [$^{15}$N,$^{1}$H]-correlation spectrum was recorded and compared with the spectrum of the apo-Bir3. No appreciable differences in the spectra were observed. Results are summarized in Table 12.

TABLE 12

STRUCTURE ACTIVITY RELATIONSHIPS (SAR) OF PURPUROGALLIN DERIVATIVES

| CMPD | $R_1$ | $R_2$ | $R_3$ | $R_4$ | $R_5$ | $IC_{50}$ (µM) (BCL-$X_L$) | $IC_{50}$ (µM) (HeLa) |
|---|---|---|---|---|---|---|---|
| Purpurogallin | —OH | —OH | —OH | —OH | —H | 2.2 | 6.5 |
| 5D1 | —H | —OH | —OH | —OH | —COOC$_2$H$_5$ | 73 | 51.5 |
| 1163 | —H | —OH | —OH | —OH | —COOCH$_3$ | 2.6 | ~30 |
| 1142 | —H | —OH | —OH | —OH | —COOH | 7.4 | 22.9 |
| 6A1 | —OCH$_3$ | —OCH$_3$ | —OCH$_3$ | —OCH$_3$ | —H | >100 | >100 |
| 6A7 | —OCH$_3$ | —OCH$_3$ | —OCH$_3$ | —OCH$_3$ | —H | >100 | >100 |

Example 20

Maximum Tolerated Dose (MTD)

Young female Balb/c mice (7-weeks-old) were injected with 100 mg/kg, 75 mg/kg, 50 mg/kg, 25 mg/kg, 12.5 mg/kg and 6.25 mg/kg of compound 8r intraperitoneally (one mouse per dose) and observed for survival, vital signs, weight loss, etc. for 14 days, in compliance with MTD general protocol proposed by DTP (Developmental Therapeutics Program) at NCI. Compound 8r was first dissolved in 100% ethanol, supplemented by Cremophore EL and saline, just before injection, with a ratio of Ethanol:Cremophore EL:Saline=10:10:80. Upon conclusion of the study, mice were euthanized by CO2, and vital organs were harvested and fixed with z-FIX solution for 3 days at room temperature, rinsed in PBS three times, for further histological evaluation.

References

Vaux, D. L.; Korsmeyer, S. J. Cell death in development. *Cell* 1999, 96, 245-54.

Reed, J. C. Dysregulation of apoptosis in cancer. *J Clin Oncol* 1999, 17, 2941-53.

Johnstone, R. W.; Ruefli, A. A.; Lowe, S. W. Apoptosis: a link between cancer genetics and chemotherapy. *Cell* 2002, 108, 153-64.

Reed, J. C. Apoptosis-based therapies. *Nature reviews Drug discovery* 2002, 1, 111-21.

Reed, J. C. Molecular biology of chronic lymphocytic leukemia: implications for therapy. *Seminars in hematology* 1998, 35, 3-13.

Adams, J. M.; Cory, S. The Bcl-2 protein family: arbiters of cell survival. *Science* (New York, N.Y.) 1998, 281, 1322-6.

Gross, A.; McDonnell, J. M.; Korsmeyer, S. J. BCL-2 family members and the mitochondria in apoptosis. *Genes & development* 1999, 13, 1899-911.

Wang, J. L.; Liu, D.; Zhang, Z. J.; Shan, S.; Han, X.; Srinivasula, S. M.; Croce, C. M.; Alnemri, E. S.; Huang, Z. Structure-based discovery of an organic compound that binds Bcl-2 protein and induces apoptosis of tumor cells. *Proceedings of the National Academy of Sciences of the United States of America* 2000, 97, 7124-9.

Degterev, A.; Lugovskoy, A.; Cardone, M.; Mulley, B.; Wagner, G.; Mitchison, T.; Yuan, J. Identification of small-molecule inhibitors of interaction between the BH3 domain and Bcl-xL. *Nat Cell Biol* 2001, 3, 173-82.

Reed, J. C. Bcl-2 family proteins. *Oncogene* 1998, 17, 3225-36.

Reed, J. C. Bcl-2 family proteins: strategies for overcoming chemoresistance in cancer. *Advances in pharmacology* (San Diego, Calif.) 1997, 41, 501-32.

Kitada, S.; Leone, M.; Sareth, S.; Zhai, D.; Reed, J. C.; Pellecchia, M. Discovery, characterization, and structure-activity relationships studies of proapoptotic polyphenols targeting B-cell lymphocyte/leukemia-2 proteins. *Journal of medicinal chemistry* 2003, 46, 4259-64.

Zhang, M.; Liu, H.; Guo, R.; Ling, Y.; Wu, X.; Li, B.; Roller, P. P.; Wang, S.; Yang, D. Molecular mechanism of gossypol-induced cell growth inhibition and cell death of HT-29 human colon carcinoma cells. *Biochemical pharmacology* 2003, 66, 93-103.

Wang, G.; Nikolovska-Coleska, Z.; Yang, C.-Y.; Wang, R.; Tang, G.; Guo, J.; Shangary, S.; Qiu, S.; Gao, W.; Yang, D.; Meagher, J.; Stuckey, J.; Krajewski, K.; Jiang, S.; Roller, P. P.; Abaan, H. O.; Tomita, Y.; Wang, S. Structure-based design of potent small-molecule inhibitors of anti-apoptotic Bcl-2 proteins. *Journal of medicinal chemistry* 2006, 49, 6139-42.

Oliver, C. L.; Miranda, M. B.; Shangary, S.; Land, S.; Wang, S.; Johnson, D. E. (−)-Gossypol acts directly on the mitochondria to overcome Bcl-2- and Bcl-X(L)-mediated apoptosis resistance. *Mol Cancer Ther* 2005, 4, 23-31.

Mohammad, R. M.; Wang, S.; Aboukameel, A.; Chen, B.; Wu, X.; Chen, J.; Al-Katib, A. Preclinical studies of a non-peptidic small-molecule inhibitor of Bcl-2 and Bcl-X(L) [(−)-gossypol] against diffuse large cell lymphoma. *Mol Cancer Ther* 2005, 4, 13-21.

Wang, S. Y., D. Small Molecular Antagonists of Bcl-2 family proteins. US patent applications series no. 2003008924. May 30, 2002

Meng, Y.; Tang, W.; Dai, Y.; Wu, X.; Liu, M.; Ji, Q.; Ji, M.; Pienta, K.; Lawrence, T.; Xu, L. Natural BH3 mimetic (−)-gossypol chemosensitizes human prostate cancer via Bcl-xL inhibition accompanied by increase of Puma and Noxa. *Mol Cancer Ther* 2008, 7, 2192-202.

Becattini, B.; Kitada, S.; Leone, M.; Monosov, E.; Chandler, S.; Zhai, D.; Kipps, T. J.; Reed, J. C.; Pellecchia, M. Rational design and real time, in-cell detection of the proapoptotic activity of a novel compound targeting Bcl-X(L). *Chemistry & biology* 2004, 11, 389-95.

Kitada, S.; Kress, C. L.; Krajewska, M.; Jia, L.; Pellecchia, M.; Reed, J. C. Bcl-2 antagonist apogossypol (NSC736630) displays single-agent activity in Bcl-2-transgenic mice and has superior efficacy with less toxicity compared with gossypol (NSC19048). *Blood* 2008, 111, 3211-9.

Coward, L.; Gorman, G.; Noker, P.; Kerstner-Wood, C.; Pellecchia, M.; Reed, J. C.; Jia, L. Quantitative determination of apogossypol, a pro-apoptotic analog of gossypol, in mouse plasma using LC/MS/MS. *Journal of pharmaceutical and biomedical analysis* 2006, 42, 581-6.

Wei, J.; Rega, M. F.; Kitada, S.; Yuan, H.; Zhai, D.; Risbood, P.; Seltzman, H. H.; Twine, C. E.; Reed, J. C.; Pellecchia, M. Synthesis and evaluation of Apogossypol atropisomers as potential Bcl-xL antagonists. *Cancer Lett* 2009, 273, 107-13.

Jun Wei, S. K., Michele F. Rega, Aras Emdadi, Hongbin Yuan, Jason Cellitti, John L. Stebbins, Dayong Zhai, Jiazhi Sun, Li Yang, Russell Dahl, Ziming Zhang, Bainan Wu, Si Wang, Tyler A. Reed, Nicholas Lawrence, Said Sebti,; Pellecchia, J. C. R. a. M. Apogossypol Derivatives as Antagonists of Anti-apoptotic Bcl-2 Family Proteins. *Mol Cancer Ther* 2009, in press.

Oltersdorf, T.; Elmore, S. W.; Shoemaker, A. R.; Armstrong, R. C.; Augeri, D. J.; Belli, B. A.; Bruncko, M.; Deckwerth, T. L.; Dinges, J.; Hajduk, P. J.; Joseph, M. K.; Kitada, S.; Korsmeyer, S. J.; Kunzer, A. R.; Letai, A.; Li, C.; Mitten, M. J.; Nettesheim, D. G.; Ng, S.; Nimmer, P. M.; O'Connor, J. M.; Oleksijew, A.; Petros, A. M.; Reed, J. C.; Shen, W.; Tahir, S. K.; Thompson, C. B.; Tomaselli, K. J.; Wang, B.; Wendt, M. D.; Zhang, H.; Fesik, S. W.; Rosenberg, S. H. An inhibitor of Bcl-2 family proteins induces regression of solid tumours. *Nature* 2005, 435, 677-81.

Bruncko, M.; Oost, T. K.; Belli, B. A.; Ding, H.; Joseph, M. K.; Kunzer, A.; Martineau, D.; McClellan, W. J.; Mitten, M.; Ng, S.C.; Nimmer, P. M.; Oltersdorf, T.; Park, C. M.; Petros, A. M.; Shoemaker, A. R.; Song, X.; Wang, X.; Wendt, M. D.; Zhang, H.; Fesik, S. W.; Rosenberg, S. H.; Elmore, S. W. Studies leading to potent, dual inhibitors of Bcl-2 and Bcl-xL. *J Med Chem* 2007, 50, 641-62.

Meltzer, P. C.; Bickford, H. P.; Lambert, G. J. A Regioselective Route to Gossypol Analogues: The Synthesis of Gossypol and 5,5'-Didesisopropyl-5,5'-diethylgossypol. *J. Org. Chem.* 1985, 50, 3121-3124.

Royer, R. E.; Deck, L. M.; Vander Jagt, T. J.; Martinez, F. J.; Mills, R. G.; Young, S. A.; Vander Jagt, D. L. Synthesis and anti-HIV activity of 1,1'-dideoxygossypol and related compounds. *J Med Chem* 1995, 38, 2427-32.

Yamanoi, Y.; Nishihara, H. Direct and selective arylation of tertiary silanes with rhodium catalyst. *J Org Chem* 2008, 73, 6671-8.

Tang, G.; Ding, K.; Nikolovska-Coleska, Z.; Yang, C. Y.; Qiu, S.; Shangary, S.; Wang, R.; Guo, J.; Gao, W.; Meagher, J.; Stuckey, J.; Krajewski, K.; Jiang, S.; Roller, P. P.; Wang, S. Structure-based design of flavonoid compounds as a new class of small-molecule inhibitors of the anti-apoptotic Bcl-2 proteins. *J Med Chem* 2007, 50, 3163-6.

Rega, M. F.; Leone, M.; Jung, D.; Cotton, N.J.; Stebbins, J. L.; Pellecchia, M. Structure-based discovery of a new class of Bcl-xL antagonists. *Bioorg Chem* 2007, 35, 344-53.

Wesarg, E.; Hoffarth, S.; Wiewrodt, R.; Kroll, M.; Biesterfeld, S.; Huber, C.; Schuler, M. Targeting BCL-2 family proteins to overcome drug resistance in non-small cell lung cancer. *Int J Cancer* 2007, 121, 2387-94.

Brien, G.; Trescol-Biemont, M. C.; Bonnefoy-Berard, N. Downregulation of Bfl-1 protein expression sensitizes malignant B cells to apoptosis. *Oncogene* 2007, 26, 5828-32.

Li, J.; Viallet, J.; Haura, E. B. A small molecule pan-Bcl-2 family inhibitor, GX15-070, induces apoptosis and enhances cisplatin-induced apoptosis in non-small cell lung cancer cells. *Cancer Chemother Pharmacol* 2008, 61, 525-34.

Voortman, J.; Checinska, A.; Giaccone, G.; Rodriguez, J. A.; Kruyt, F. A. Bortezomib, but not cisplatin, induces mitochondria-dependent apoptosis accompanied by up-regulation of noxa in the non-small cell lung cancer cell line NCI-H460. *Mol Cancer Ther* 2007, 6, 1046-53.

Ferreira, C. G.; Span, S. W.; Peters, G. J.; Kruyt, F. A.; Giaccone, G. Chemotherapy triggers apoptosis in a caspase-8-dependent and mitochondria-controlled manner in the non-small cell lung cancer cell line NCI-H460. *Cancer Res* 2000, 60, 7133-41.

Cory, S.; Adams, J. M. Killing cancer cells by flipping the Bcl-2/Bax switch. *Cancer cell* 2005, 8, 5-6.

Wei, M. C.; Zong, W. X.; Cheng, E. H.; Lindsten, T.; Panoutsakopoulou, V.; Ross, A. J.; Roth, K. A.; MacGregor, G. R.; Thompson, C. B.; Korsmeyer, S. J. Proapoptotic BAX and BAK: a requisite gateway to mitochondrial dysfunction and death. *Science* (New York, N.Y.) 2001, 292, 727-30.

Zhai, D.; Jin, C.; Shiau, C. W.; Kitada, S.; Satterthwait, A. C.; Reed, J. C. Gambogic acid is an antagonist of antiapoptotic Bcl-2 family proteins. *Mol Cancer Ther* 2008, 7, 1639-46.

Oltersdorf, T.; Elmore, S. W.; Shoemaker, A. R.; Armstrong, R. C.; Augeri, D. J.; Belli, B. A.; Bruncko, M.; Deckwerth, T. L.; Dinges, J.; Hajduk, P. J.; Joseph, M. K.; Kitada, S.; Korsmeyer, S. J.; Kunzer, A. R.; Letai, A.; Li, C.; Mitten, M. J.; Nettesheim, D. G.; Ng, S.; Nimmer, P. M.; O'Connor, J. M.; Oleksijew, A.; Petros, A. M.; Reed, J. C.; Shen, W.; Tahir, S. K.; Thompson, C. B.; Tomaselli, K. J.; Wang, B.; Wendt, M. D.; Zhang, H.; Fesik, S. W.; Rosenberg, S. H. An inhibitor of Bcl-2 family proteins induces regression of solid tumours. *Nature* 2005, 435, 677-81.

Bruncko, M.; Oost, T. K.; Belli, B. A.; Ding, H.; Joseph, M. K.; Kunzer, A.; Martineau, D.; McClellan, W. J.; Mitten, M.; Ng, S.C.; Nimmer, P. M.; Oltersdorf, T.; Park, C. M.; Petros, A. M.; Shoemaker, A. R.; Song, X.; Wang, X.; Wendt, M. D.; Zhang, H.; Fesik, S. W.; Rosenberg, S. H.; Elmore, S. W. Studies leading to potent, dual inhibitors of Bcl-2 and Bcl-xL. *J Med Chem* 2007, 50, 641-62.

Jones, G.; Willett, P.; Glen, R. C.; Leach, A. R.; Taylor, R. Development and validation of a genetic algorithm for flexible docking. *Journal of molecular biology* 1997, 267, 727-48.

Eldridge, M. D.; Murray, C. W.; Auton, T. R.; Paolini, G. V.; Mee, R. P. Empirical scoring functions: I. The development of a fast empirical scoring function to estimate the binding affinity of ligands in receptor complexes. *J Comput Aided Mol Des* 1997, 11, 425-45.

Teschner, M.; Henn, C.; Vollhardt, H.; Reiling, S.; Brickmann, J. Texture mapping: a new tool for molecular graphics. *J Mol Graph* 1994, 12, 98-105.

Rega, M. F.; Leone, M.; Jung, D.; Cotton, N.J.; Stebbins, J. L.; Pellecchia, M. Structure-based discovery of a new class of Bcl-xL antagonists. *Bioorg Chem* 2007, 35, 344-53.

Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. Structure of Bcl-xL-Bak peptide complex: recognition between regulators of apoptosis. *Science* (New York, N.Y.) 1997, 275, 983-6.

Ramjaun, A. R.; Tomlinson, S.; Eddaoudi, A.; Downward, J. Upregulation of two BH3-only proteins, Bmf and Bim, during TGF beta-induced apoptosis. *Oncogene* 2007, 26, 970-81.

Katsumata, M.; Siegel, R. M.; Louie, D.C.; Miyashita, T.; Tsujimoto, Y.; Nowell, P. C.; Greene, M. I.; Reed, J. C. Differential effects of Bcl-2 on T and B cells in transgenic mice. *Proc Natl Acad Sci USA* 1992, 89, 11376-80.

Kitada, S.; Kress, C. L.; Krajewska, M.; Jia, L.; Pellecchia, M.; Reed, J. C. Bcl-2 antagonist apogossypol (NSC736630) displays single-agent activity in Bcl-2-transgenic mice and has superior efficacy with less toxicity compared with gossypol (NSC19048). *Blood* 2008, 111, 3211-9.

Although the disclosure has been described with reference to the above examples, it will be understood that modifications and variations are encompassed within the spirit and scope of the disclosure. Accordingly, the disclosure is limited only by the following claims.

What is claimed is:

1. A compound having structure A, or a pharmaceutically acceptable salt thereof:

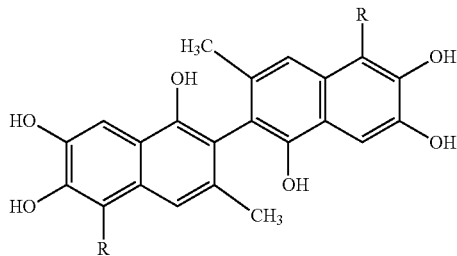

wherein:
each R is independently C(O)NHX; and
X is alkylaryl, or substituted alkylaryl.

2. The compound of claim 1, wherein X is $(C_1\text{-}C_6)$alkylaryl or substituted $(C_1\text{-}C_6)$alkylaryl, wherein each substituent is $(C_1\text{-}C_6)$alkyl, trifluoromethyl, halogen, phenyl or phenoxy.

3. The compound of claim 1, wherein each R is independently $C(O)NHCH_2CH(CH_3)C_6H_5$.

4. A compound of claim 1, or pharmaceutically acceptable salt thereof, having the structure:

(8r)

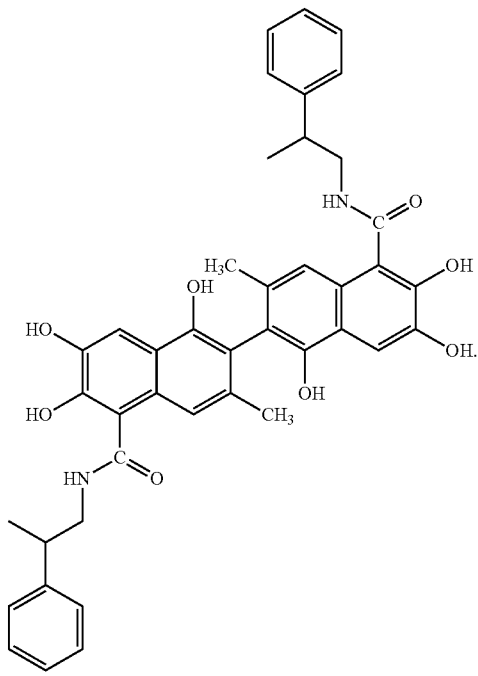

5. A pharmaceutical composition comprising a compound of claim 1, or pharmaceutically acceptable salt thereof, and a pharmaceutically acceptable carrier.

6. A pharmaceutical composition comprising a compound of claim 4, or a pharmaceutically acceptable salt thereof, and a pharmaceutically acceptable carrier.

7. A method for treating breast cancer, colon cancer, lung cancer, ovarian cancer, prostate cancer, renal cancer, leukemia, lymphoma, or melanoma, the method comprising the step of administering to a subject in need thereof a therapeutically effective amount of a compound having structure A of claim 1, or a combination thereof, or a pharmaceutically acceptable salt thereof, thereby treating the disease or the disorder.

8. A method of treating a cancer selected from breast cancer, colon cancer, lung cancer, ovarian cancer, prostate cancer, renal cancer, leukemia, lymphoma, and melanoma in a subject having at least one elevated BCL-2 family protein expression level, the method comprising the step of administering to the subject a therapeutically effective amount of a compound of claim 4, or a pharmaceutically acceptable salt thereof.

9. The method of claim 8, further comprising determining whether the subject is responsive to a therapy that utilizes the compound, comprising determining the level of at least one of the BCL-2 family protein in the subject and comparing to a normal control sample, wherein an elevated level is indicative of a subject responsive to the therapy that the compound, or a pharmaceutically acceptable salt thereof.

10. The method of claim 9, wherein the determination is made based on a sample from the subject.

11. A method of determining whether a subject is responsive to a therapy that utilizes a compound of claim 4, or a pharmaceutically acceptable salt thereof the method comprising the step of determining the level of at least one of the BCL-2 family protein in the subject and comparing to a normal control sample, wherein an elevated level is indicative of a subject responsive to the therapy that utilizes the compound, or a pharmaceutically acceptable salt thereof.

12. The method of claim 11, wherein the determination is made based on a sample from the subject.

13. The method of claim 11, wherein the sample is a biological fluid or tumor sample.

14. The method of claim 11, wherein the BCL-2 family polynucleotide or polypeptide is selected from BCL-2, BCL-XL, BCL-W, MCL-1, and BCL-A1.

15. A method of inducing apoptosis in a cancer cell having a level of at least one of the BCL-2 family protein member greater than levels in a control cell, wherein the cancer cell is a breast cancer cell, colon cancer cell, lung cancer cell, ovarian cancer cell, prostate cancer cell, renal cancer cell, leukemia cell, lymphoma cell, or melanoma cell, the method comprising the step of administering to the cell an effective amount of a of claim 4, or a pharmaceutically acceptable salt thereof, to reduce the level of BCL-2 family protein(s) and induce apoptosis in the cell.

* * * * *